(12) United States Patent
Ali et al.

(10) Patent No.: US 8,734,846 B2
(45) Date of Patent: May 27, 2014

(54) METHODS FOR THE PREPARATION OF TARGETING AGENT FUNCTIONALIZED DIBLOCK COPOLYMERS FOR USE IN FABRICATION OF THERAPEUTIC TARGETED NANOPARTICLES

(71) Applicant: Bind Biosciences, Inc., Cambridge, MA (US)

(72) Inventors: Mir M. Ali, Woburn, MA (US); Jeff Hrkach, Lexington, MA (US); Stephen E. Zale, Hopkinton, MA (US); Luis Alvarez de Cienfuegos, Granada (ES)

(73) Assignee: Bind Biosciences, Inc., Cambridge, MA (US)

( * ) Notice: Subject to any disclaimer, the term of this patent is extended or adjusted under 35 U.S.C. 154(b) by 0 days.

(21) Appl. No.: 13/667,299

(22) Filed: Nov. 2, 2012

(65) Prior Publication Data

US 2013/0115192 A1 May 9, 2013

Related U.S. Application Data

(63) Continuation of application No. 12/485,818, filed on Jun. 16, 2009, now abandoned.

(60) Provisional application No. 61/061,712, filed on Jun. 16, 2008.

(51) Int. Cl.
*A61K 9/14* (2006.01)

(52) U.S. Cl.
USPC ........................................................ 424/489

(58) Field of Classification Search
None
See application file for complete search history.

(56) References Cited

U.S. PATENT DOCUMENTS

| 7,550,441 | B2 | 6/2009 | Farokhzad et al. |
| 2002/0197261 | A1 | 12/2002 | Li et al. |
| 2005/0042298 | A1 | 2/2005 | Pardridge et al. |
| 2005/0266067 | A1 | 12/2005 | Sengupta et al. |

FOREIGN PATENT DOCUMENTS

| JP | 2002-515418 | 5/2002 |
| WO | WO 99/59546 | 11/1999 |
| WO | WO 2007/133807 | 11/2007 |

OTHER PUBLICATIONS

Written Opinion in International Application No. PCT/US2009/047554, Jan. 18, 2010, pp. 1-6.
Lupold, S. E. et al. "Identification and Characterization of Nuclease-stabilized RNA Molecules That Bind Human Prostate Cancer Cells via the Prostate-specific Membrane Antigen" *Cancer Res*, 2002, pp. 4029-4033, vol. 62.

*Primary Examiner* — Paul Dickinson
(74) *Attorney, Agent, or Firm* — Saliwanchik, Lloyd & Eisenschenk

(57) ABSTRACT

This application provides nanoparticles and methods of making nanoparticles using pre-functionalized poly(ethylene glycol)(also referred to as PEG) as a macroinitiator for the synthesis of diblock copolymers. Ring opening polymerization yields the desired poly(ester)-poly (ethylene glycol)-targeting agent polymer that is used to impart targeting capability to therapeutic nanoparticles. This "polymerization from" approach typically employs precursors of the targeting agent wherein the reactivity of functional groups of the targeting agent is masked using protecting groups. Also described is a "coupling to" that utilized the poly(ethylene glycol)-targeting agent conjugate where the targeting agent remains in its native un-protected form. This method uses "orthogonal" chemistry that exhibit no cross reactivity towards functional groups typically found within targeting agents of interest.

20 Claims, 22 Drawing Sheets

Non-Interpolated Peak Listing

| PEAK | POINT | HEIGHT | REL. HT | HZ | PPM |
|---|---|---|---|---|---|
| 1 | 16593 | 551876 | 0.06 | 2408.29 | 6.026 |
| 2 | 16618 | 1113K | 0.12 | 2402.94 | 6.013 |
| 3 | 16642 | 1149K | 0.13 | 2397.79 | 6.000 |
| 4 | 16668 | 1717K | 0.19 | 2392.22 | 5.986 |
| 5 | 16694 | 1657K | 0.18 | 2386.65 | 5.972 |
| 6 | 16723 | 1332K | 0.15 | 2380.43 | 5.957 |
| 7 | 16748 | 1411K | 0.16 | 2375.07 | 5.943 |
| 8 | 16773 | 701994 | 0.08 | 2369.72 | 5.930 |
| 9 | 17780 | 2599K | 0.29 | 2153.90 | 5.390 |
| 10 | 17861 | 2285K | 0.25 | 2136.54 | 5.346 |
| 11 | 17903 | 2723K | 0.30 | 2127.54 | 5.324 |
| 12 | 17952 | 2519K | 0.28 | 2117.04 | 5.298 |
| 13 | 17958 | 2433K | 0.27 | 2115.75 | 5.294 |
| 14 | 18911 | 72556K | 8.02 | 1911.51 | 4.783 |
| 15 | 18914 | 90267K | 9.98 | 1910.87 | 4.782 |
| 16 | 19085 | 4592K | 0.51 | 1874.22 | 4.690 |
| 17 | 19110 | 4623K | 0.51 | 1868.86 | 4.677 |
| 18 | 19156 | 2479K | 0.27 | 1859.00 | 4.652 |
| 19 | 19161 | 2628K | 0.29 | 1857.93 | 4.649 |
| 20 | 19182 | 2449K | 0.27 | 1853.43 | 4.638 |
| 21 | 19187 | 2546K | 0.28 | 1852.36 | 4.635 |
| 22 | 19707 | 732369 | 0.08 | 1740.91 | 4.356 |
| 23 | 19731 | 850033 | 0.09 | 1735.77 | 4.343 |
| 24 | 19749 | 862928 | 0.10 | 1731.91 | 4.334 |
| 25 | 19774 | 793732 | 0.09 | 1726.55 | 4.320 |
| 26 | 19813 | 999439 | 0.11 | 1718.20 | 4.300 |
| 27 | 19868 | 671323 | 0.07 | 1706.41 | 4.270 |
| 28 | 19893 | 767370 | 0.08 | 1701.05 | 4.257 |
| 29 | 19907 | 805149 | 0.09 | 1698.05 | 4.249 |
| 30 | 19932 | 666755 | 0.07 | 1692.69 | 4.236 |
| 31 | 20167 | 284016 | 0.03 | 1642.33 | 4.110 |
| 32 | 20197 | 226930 | 0.03 | 1635.90 | 4.094 |

FIG. 1C-2

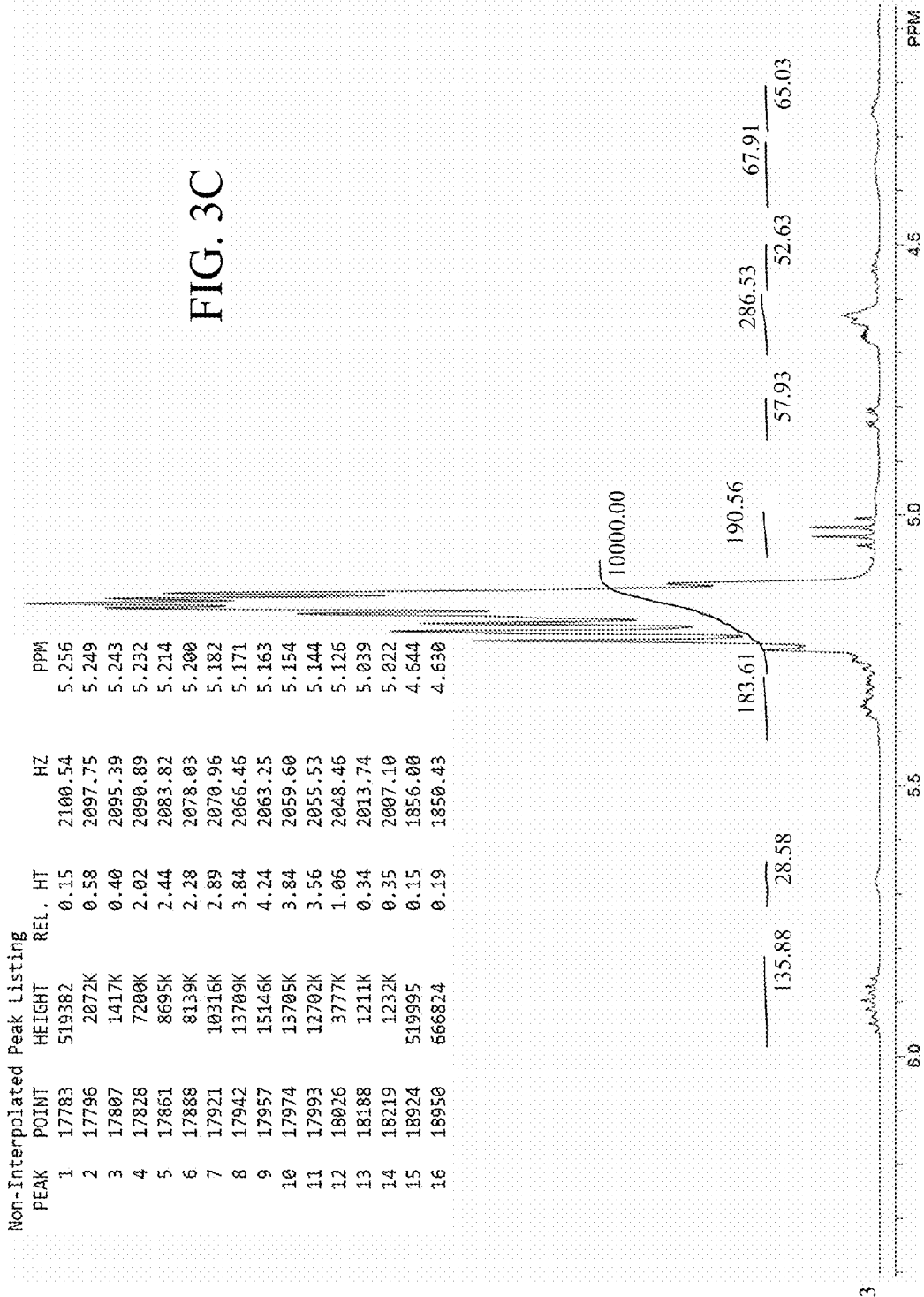

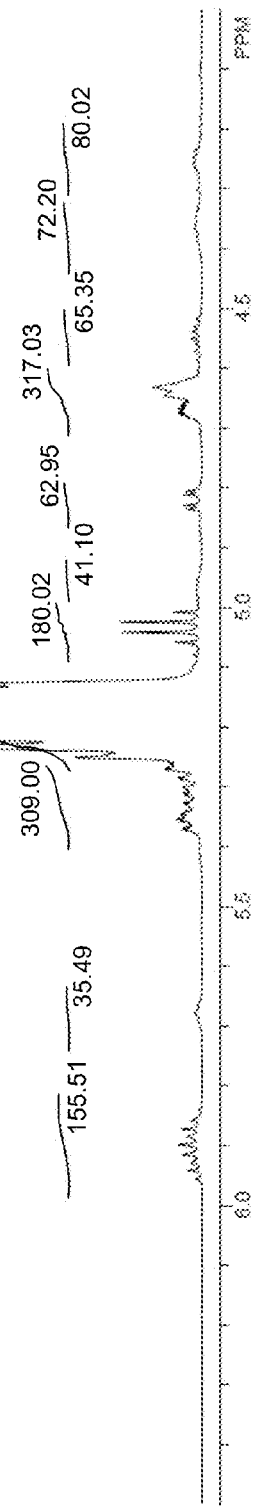

Non-Interpolated Peak Listing
| PEAK | POINT | HEIGHT | REL. HT | HZ | PPM |
|---|---|---|---|---|---|
| 1 | 17703 | 1207K | 0.93 | 2118.33 | 5.301 |
| 2 | 17794 | 763233 | 0.59 | 2098.82 | 5.252 |
| 3 | 17827 | 2867K | 2.22 | 2091.75 | 5.234 |
| 4 | 17859 | 3462K | 2.68 | 2084.89 | 5.217 |
| 5 | 17886 | 3303K | 2.55 | 2079.11 | 5.203 |
| 6 | 17919 | 4209K | 3.26 | 2072.03 | 5.185 |
| 7 | 17940 | 5627K | 4.35 | 2067.53 | 5.174 |
| 8 | 17955 | 6157K | 4.76 | 2064.32 | 5.166 |
| 9 | 17973 | 5522K | 4.27 | 2060.46 | 5.156 |
| 10 | 17991 | 5112K | 3.95 | 2056.60 | 5.146 |
| 11 | 18024 | 1486K | 1.15 | 2049.53 | 5.129 |
| 12 | 18084 | 38914 | 0.03 | 2036.67 | 5.096 |
| 13 | 18648 | 37951 | 0.03 | 1915.80 | 4.794 |
| 14 | 18660 | 40623 | 0.03 | 1913.23 | 4.788 |
| 15 | 18693 | 44943 | 0.03 | 1906.15 | 4.770 |
| 16 | 19414 | 43373 | 0.03 | 1751.63 | 4.383 |
| 17 | 19449 | 70126 | 0.05 | 1744.13 | 4.364 |
| 18 | 19482 | 68246 | 0.05 | 1737.06 | 4.347 |
| 19 | 19632 | 49638 | 0.04 | 1704.91 | 4.266 |
| 20 | 19640 | 50185 | 0.04 | 1703.20 | 4.262 |
| 21 | 19663 | 50170 | 0.04 | 1698.27 | 4.250 |

| Sample Code/Lot | Sample description | Polymer solvent in IV analysis | Polymer Conc. g/dL | Inherent Viscosity Trial 1 dL/g | Inherent Viscosity Trial 2 dL/g | Average IV dL/g | Standard Deviation |
|---|---|---|---|---|---|---|---|
| 11-196-6 | PLA-PEG-lys-urea-glu(protected) | DMSO | 0.1 | 0.229 | 0.205 | 0.217 | 0.016 |
| 44-49-1 | PLA-PEG-lys-urea-glu | DMSO | 0.1 | 0.198 | 0.198 | 0.198 | 0 |
| 44-49-1 | PLA-PEG-lys-urea-glu | Chloroform | 0.1 | 0.303 | 0.314 | 0.309 | 0.008 |

FIG. 7

| SAMPLE ID | LAB ID | ANALYSIS | RESULT(S) | DUPLICATE RESULT(S) |
|---|---|---|---|---|
| 11-204-1 | G-8391 | Palladium | 3780 ppm | 3880 ppm |
| 11-204-2 | G-8392 | Palladium | 3.8 ppm | 2.7 ppm |

FIG. 8

METHODS FOR THE PREPARATION OF TARGETING AGENT FUNCTIONALIZED DIBLOCK COPOLYMERS FOR USE IN FABRICATION OF THERAPEUTIC TARGETED NANOPARTICLES

This application is a continuation of U.S. Ser. No. 12/485,818, filed Jun. 16, 2009 which claims the benefit of U.S. Provisional Patent Application 61/061,712, filed Jun. 16, 2008, the disclosures of which are hereby incorporated by reference in their entirety.

This invention was made with United States Government support under Cooperative Agreement Number 70NANB7H7021 awarded by the National Institute of Standard and Technology (NIST). The United States Government has certain rights in the invention.

BACKGROUND OF THE INVENTION

The delivery of a drug to a patient with controlled-release of the active ingredient has been an active area of research for decades and has been fueled by the many recent developments in polymer science. In addition, controlled release polymer systems can be designed to provide a drug level in the optimum range over a longer period of time than other drug delivery methods, thus increasing the efficacy of the drug and minimizing problems with patient compliance.

Biodegradable particles have been developed as sustained release vehicles used in the administration of small molecule drugs, proteins and peptide drugs, and nucleic acids. The drugs are typically encapsulated in a polymer matrix which is biodegradable and biocompatible. As the polymer is degraded and/or as the drug diffuses out of the polymer, the drug is released into the body.

Targeting controlled release polymer systems (e.g., targeted to a particular tissue or cell type or targeted to a specific diseased tissue but not normal tissue) is desirable because it reduces the amount of a drug present in tissues of the body that are not targeted. This is particularly important when treating a condition such as cancer where it is desirable that a cytotoxic dose of the drug is delivered to target cells without killing the surrounding tissue. Accordingly, a need exists to develop delivery systems which can deliver therapeutic levels of drug to treat diseases such as cancer, while also reducing patient side effects.

BRIEF SUMMARY OF THE INVENTION

This application provides methods of making nanoparticles using pre-functionalized poly(ethylene glycol)(also referred to as PEG) as a macroinitiator for the synthesis of diblock copolymers. These diblock copolymers comprise a functional PEG polymer block bearing a targeting agent on one of its termini and a second biocompatible and biodegradable hydrophobic polymer block (e.g. a poly(ester)). The poly(ethylene glycol) is hetero-bifunctional with a targeting agent (TA) covalently bound to its α terminus and a polymerization initiating functional group (e.g., a hydroxyl group) present on its ω terminus. Alternatively, the poly(ethylene glycol) is functionalized with a TA on its α terminus and a functional group capable of covalent attachment to a poly (ester) that in turn is functionalized with a reactive end group. Examples include an amino-terminated PEG and a carboxylic acid terminated poly(ester) or an azide terminated PEG and an alkyne terminated poly(ester). Nanoparticles produced according to the disclosed methods and their use in the treatment of various diseases and disorders is also provided.

BRIEF DESCRIPTION OF THE FIGURES

FIGS. 1A-C: Proton NMR spectra of HO-PEG-lys-urea-glu(protected), lot numbers 11-189-1 and 11-176-1. FIG. 1A—HO-PEG-lys-urea-glu(protected) Lot#11-176-1. 1H NMR spectrum expansion #1 used for lys-urea-glu(protected) content calculation (% lys-urea-glu(protected) end functionalization=[Int.δ1.95-2.1]*2/[Int. δ2.15-2.3]*100%=[2*10847/25777]*100=84%). FIG. 1B—HO-PEG-lys-urea-glu(protected) Lot#11-176-1; 1H NMR spectrum expansion #2. FIGS. 1C-1 and 1C-2—HO-PEG-lys-urea-glu(protected) Lot#11-176-1; 1H NMR spectrum expansion #3.

SEC Conditions:
Detector: Refractive Index detection (RI); RI Detector temperature=35° C.
Columns: Water Styragel (HR1, 100-5000 Da; HR3, 500-30000 Da; HR4, 5000-600,000 Da in series).
Column Temperature=30° C.;
Mobile phase: Chloroform; Flow rate: 1 mL/min
Sample concentration=10 mg/mL, Injection volume=50 uL (11-176-1) and 100 uL (11-189-1 coded 44-44-6 in chromatogram legends below);
Number and Weight Average Molecular Weight ($M_n$ and $M_w$) and Polydispersity ($M_w/M_n$) were obtained relative to narrow disperse Poly(ethylene glycol) Standards (Polymer Standards Service USA, Warwick, R.I.). A fourth order polynomial fit ($R^2$=0.99957; Standard Error=0.02) was used for calibration. 11-176-1 (FIG. 2A) and 11-189-1 (FIG. 2B) SEC Chromatograms FIGS. 3A-F: Proton NMR spectra of PLA-PEG-lys-urea-glu(protected), lot numbers 11-187-1, 11-188-1 and 11-198-1.
NMR Instrument: Bruker 400 MHz
NMR Experiment Parameters:
Solvent: $CDCl_3$; Pulse Width: 7.5 usec; Pulse Delay: 5 sec; Number of scans: 128

FIG. 3A—PLA-PEG-lys-urea-glu(protected), Lot #11-187-1; 1H NMR Spectrum Expansion #1 showing lactide methine and allyl end group peak used in the determination the determination of the absolute number average molar mass (Mn) of PLA-PEG-lys-urea-glu(protected). Method for determination of absolute number average molar mass ($M_n$) of PLA-PEG-lys-urea-glu(protected): $M_n$(PLA-PEG-lys-urea-glu(protected)=$M_n$(PEG-lys-urea-glu(protected)+(Molar mass of lactide repeat unit*((Int. δ5.1-5.3 ppm)*3)/(Int.δ5.85 ppm-5.95 ppm)=5000+((72*10,000)*3)/143)=20,105 Da. FIG. 3B—PLA-PEG-lys-urea-glu(protected), Lot#11-187-1; 1H NMR Spectrum Expansion #2 showing PEG peak and lactide methyl peaks of PLA-PEG-lys-urea-glu(protected). FIG. 3C—PLA-PEG-lys-urea-glu(protected), Lot#11-188-1; 1H NMR Spectrum Expansion #1 showing lactide methine and allyl end group peak used in the determination the determination of the absolute number average molar mass (Mn) of PLA-PEG-lys-urea-glu(protected). Method for determination of absolute number average molar mass ($M_n$) of PLA-PEG-lys-urea-glu(protected): $M_n$(PLA-PEG-lys-urea-glu(protected)=$M_n$(PEG-lys-urea-glu(protected)+(Molar mass of lactide repeat unit*((Int. δ5.1-5.3 ppm)*3)/(Int.δ5.85 ppm-5.95 ppm)=5000+((72*10,000)*3)/137)=20,766 Da. FIG. 3D—PLA-PEG-lys-urea-glu(protected), Lot#11-188-1; 1H NMR Spectrum Expansion #2 showing PEG peak and lactide methyl peaks of PLA-PEG-lys-urea-glu(protected). FIG. 3E—PLA-PEG-lys-urea-glu(protected), Lot#11-198-1; 1H NMR Spectrum Expansion #1 showing lactide methine and allyl end group peak used in the determination the determination of the absolute number average molar mass (Mn) of PLA-PEG-lys-urea-glu(protected). Method for determination of absolute number average molar mass ($M_n$) of PLA-PEG-lys-urea-glu(protected): $M_n$(PLA-PEG-lys-urea-glu(protected)=$M_n$(PEG-lys-urea-glu(protected)+(Molar mass of lactide repeat unit* ((Int. δ5.1 ppm-5.3 ppm)*3)/(Int.δ5.85 ppm-5.95 ppm)= 5000+((72*10,000)*3)/156)=18,846 Da. FIG. 3F—PLA-PEG-lys-urea-glu(protected), Lot#11-198-1; 1H NMR Spectrum Expansion #2 showing PEG peak and lactide methyl peaks of PLA-PEG-lys-urea-glu(protected).

FIG. 5B—Crude PLA-PEG-lys-urea-glu Lot#11-190-1; 1H NMR Spectrum Expansion #2 showing the PEG and lactide methyl peaks.
FIG. 5C—Crude PLA-PEG-lys-urea-glu Lot#11-191-1; 1H NMR Spectrum Expansion #1 showing: a) lactide methine peak, b) peaks of aromatic protons of tetrakis(triphenyl-phosphine)palladium (0), and c)<3% (relative to the PLA-PEG-lys-urea-glu(protected) precursor) residual allyl peaks (δ 5.85-5.95) indicating >96% removal of protecting groups.
FIG. 5D—Crude PLA-PEG-lys-urea-glu Lot#11-191-1; 1H NMR Spectrum Expansion #2 showing PEG and lactide methyl peaks.
FIG. 5E—Crude PLA-PEG-lys-urea-glu Lot#11-199-1; 1H NMR Spectrum Expansion #1 showing: a) lactide methine peak, b) absence of residual allyl peaks (δ 5.85-5.95) indicating quantitative removal of protecting groups.

FIG. 6B—Purified PLA-PEG-lys-urea-glu Lot#44-49-1; 1H NMR Spectrum Expansion #2 showing PEG and lactide methyl peaks.

FIG. 7: Molecular weight of PLA-PEG-lys-urea-glu and the protected precursor PLA-PEG-lys-urea-glu(protected) by Inherent Viscosity measurements.

FIG. 8: Palladium Content in crude (prior to palladium removal) PLA-PEG-lys-urea-glu lot number 44-48-1 (sample code 11-204-1) and purified (after palladium removal) PLA-PEG-lys-urea-glu lot number 44-49-1 (sample code 11-204-2) determined by ICP Spectrometry.

DETAILED DISCLOSURE OF THE INVENTION

Figure 1A:
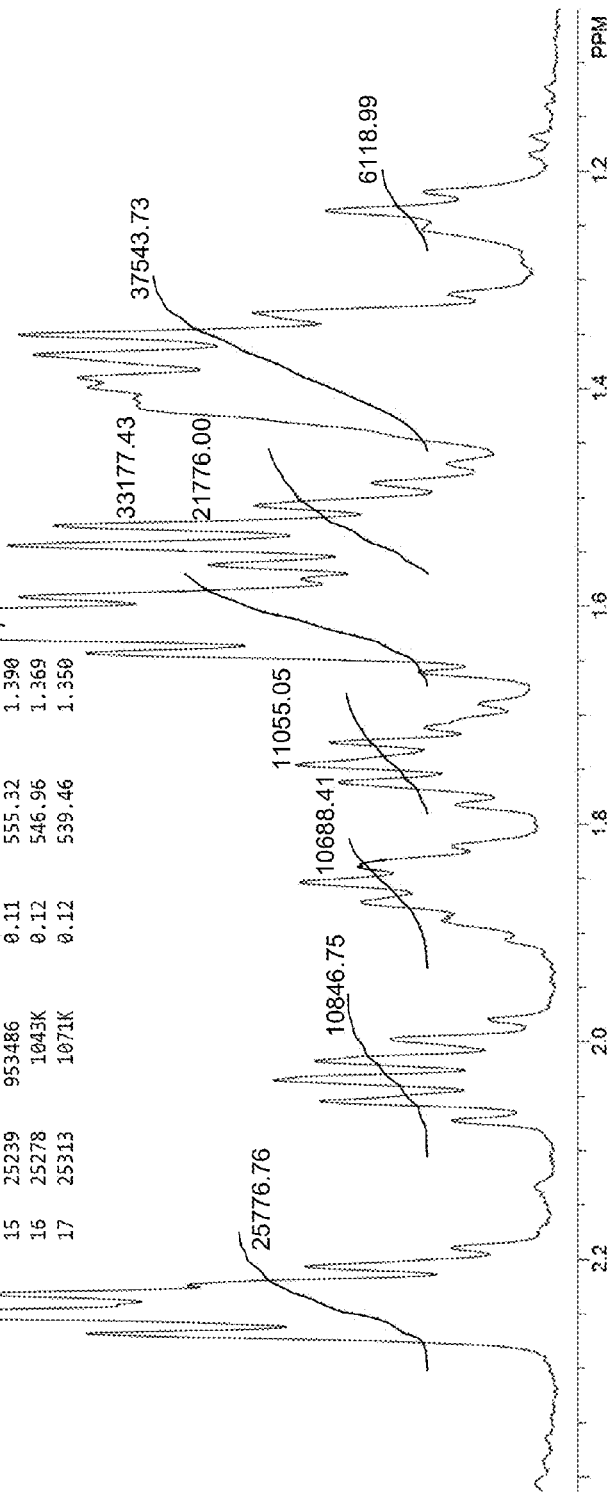
Figure 1B:
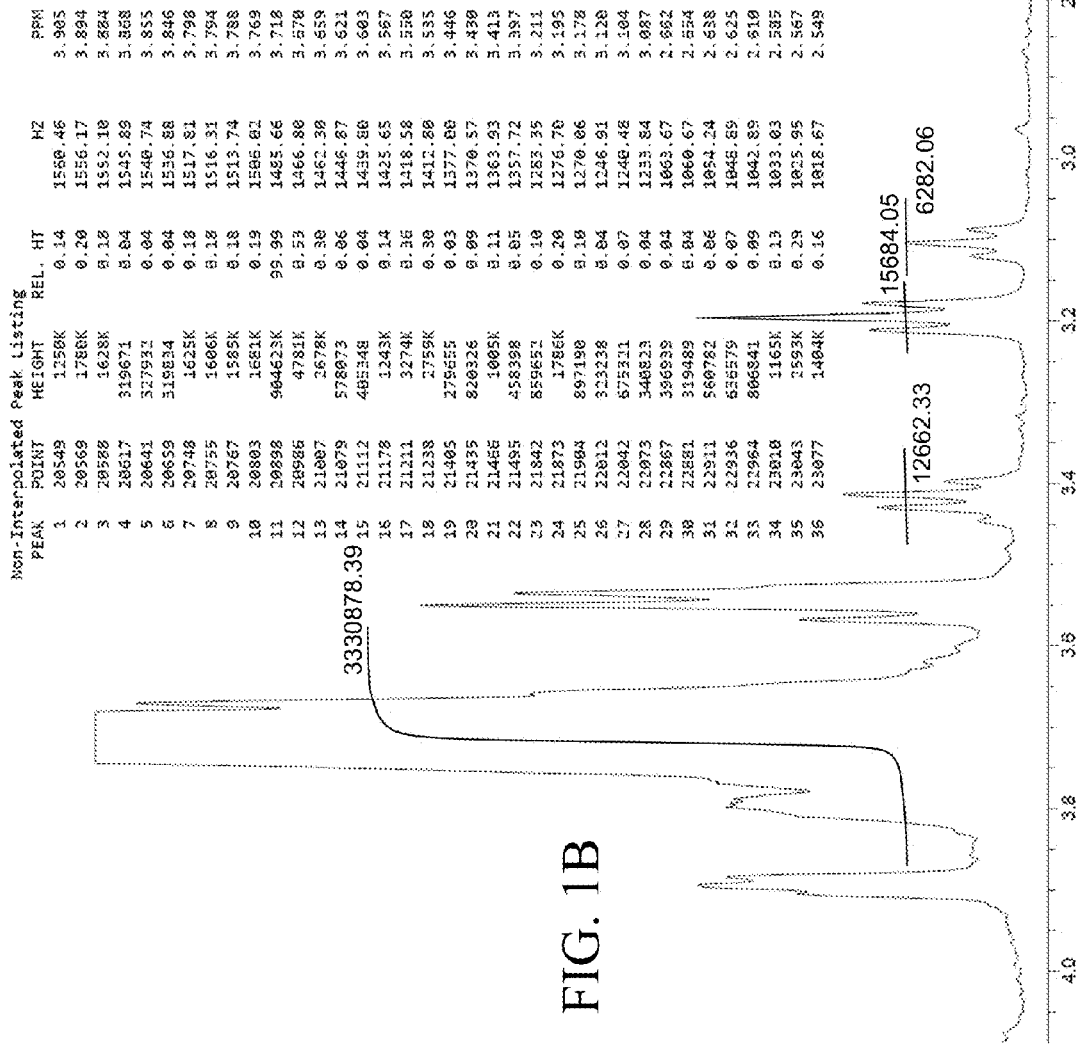

This application provides methods of making nanoparticles using pre-functionalized poly(ethylene glycol)(also referred to as PEG) as a macroinitiator for the synthesis of diblock copolymers. These diblock copolymers comprise a bio-active poly(ethylene glycol) block and a second biocompatible and biodegradable hydrophobic polymer block (e.g. a poly(ester)). The poly(ethylene glycol) is hetero-bifunctional with a targeting moiety (agent) covalently bound to its α terminus and a polymerization initiating functional group (e.g., a hydroxyl group) present on its ω terminus.

The subject application also provides for the use of derivatives of targeting agents (TA's) (e.g., analogs where functional groups, such as carboxylic acids or other functional groups, are protected) in the synthesis of the poly(ethylene glycol) polymer to which TA's are attached that improve its solubility and avoid potential side reactions. After a protected targeting agent (PRO-TA) is coupled to the PEG polymer at the α terminus, the functionalized PEG (HO-PEG-TA-PRO) is utilized as a macroinitiator to synthesize a poly(ester) block. For example, HO-PEG-TA-PRO is added to a mixture of cyclic lactone monomers such as lactide, glycolide or caprolactone and the mixture is heated to melt conditions. A polymerization catalyst, such as tin (II) 2-ethylhexanoate is then added to the monomer/initiator melt. The resulting polymer is purified from un-reacted monomer and polymerization catalyst by precipitation into a non-solvent mixture such as ether/hexane (70/30) and recovered by decantation followed by vacuum drying. Subsequent deprotection of the protected functional groups can be performed to regain the original chemically active functional group (e.g., a carboxylic acid). This approach enables the desired polymerization reaction to proceed efficiently and avoids side reactions between the polymerization catalyst and the functional groups on the targeting moiety in its native unprotected form. Such side reactions result in the formation of cross-linked insoluble gels rather than the desired linear poly(ester) polymer. In addition, the composition and molecular weight of the poly(ester) can be tuned as desired by controlling the composition of the monomer melt and the molar ratio of the HO-PEG-TA(PRO) to the monomers. Furthermore, the protected targeting moiety is freely soluble in a wide range of organic solvents relative to the un-protected analogues. This enables the coupling of the targeting moiety to poly(ethylene glycol) with a high degree of polymer end group functionalization. Non-limiting examples of protecting groups for various targeting agent functional groups, as disclosed herein, are:

| Functional group | Protecting group |
| --- | --- |
| Alcohol | Alkyl allyl carbonate, Alloc-OR |
| Alcohol | Methyl ether |
| Alcohol | Methyl ether |
| Alcohol | Methyl ether |

-continued

| Functional group | Protecting group |
|---|---|
| Alcohol | Allyl benzylcarbonate, ROCO$_2$Bn |
| Phenol | Allyl carbonate |
| Phenol | Methyl ether |
| Phenol | Benzyloxymethyl ether—BOM |
| Phenol | Methoxyethoxymethyl Ether—MEM ether |
| Thiol | S-p-Methoxybenzyl thioether |
| Thiol | S-Triphenylmethyl thioether (Tr-SR) |
| Thiol | 4-methoxytrityl (Mtt-SR) |
| Thiol | S-t-butyl thioether |
| Thiol | S-[Tricarbonyl[1,2,3,4,5,$\eta$)]-2,4-dicyclohexadiene-1-yl]-iron(1+) thioether |
| Amine | N-allylamine |
| Amine | N-benzylamine |
| Amine | Allyl carbamate (Alloc-NR2) |
| Amine | Benzyl carbamate—benzyloxycarbonyl (CBz) |
| Amine | p-methoxybenzyl carbamate—Moz |
| Amine | p-nitrobenzyl carbamate—PNZ |
| Carboxylic acid | Allyl ester |
| Carboxylic acid | Propargyl ester |
| Carboxylic acid | Benzyl ester—RCO$_2$Bn |

Additionally, this application provides a method for efficient coupling of the un-protected targeting moiety to poly(ethylene glycol) under aqueous conditions. In this approach, the pH of the reaction medium is used to maximize yield of the desired product. Advantages to this aspect of the invention relate to the utilization of the high water solubility of the targeting agent (TA). For example, the acid end group of a $\alpha$-azide-$\omega$-carboxylic acid poly(ethylene glycol) (N$_3$-PEG-CO$_2$H) is first activated by conversion to the succinimide ester N$_3$-PEG-COSu) by reaction with N-hydroxysuccinimide (NHS) and ethyl dimethylaminopropylcarbodiimide hydrochloride (EDC) or dicyclohexylcarbodiimide (DCC) under anhydrous organic solvent conditions such as in dichloromethane. The activated poly(ethylene glycol) (N$_3$-PEG-COSu) is subsequently purified from small molecule reagents precipitation into an anhydrous non-solvent such as ether-hexane (70/30). The un-protected form of the amine-functional targeting agent (H$_2$N-TA) is dissolved in bicarbonate buffer (pH=9.7) and pH then lowered to 7.4 using aqueous sodium hydroxide. The activated acid (N$_3$-PEG-COSu) is dissolved in DI water is added dropwise to a large molar excess of the H$_2$N-TA solution. The succinimide ester of N$_3$-PEG-COSu is stable at pH=5.5-6, while the amide bond forming reaction with H$_2$N-TA is efficient under pH=7.4 conditions. This strategy exposes the N$_3$-PEG-COSu to pH=7.4 only when a large excess of amine-functional targeting moiety is also present. Thus, conversion to the desired PEG-targeting agent conjugate (N$_3$-PEG-TA) while minimizing exposure of the N$_3$-PEG-COSu to basic conditions, thereby avoiding hydrolysis of the succinimide ester. The N$_3$-PEG-TA is subsequently coupled to an alkyne terminal poly(ester) using copper catalyst under conventional click chemistry conditions in an organic solvent such as dimethylformamide (DMF) or dimethylsulfoxide (DMSO). Alkyne terminal poly(ester) is prepared by ring opening polymerization of lactide and glycolide monomers using for example propargyl alcohol as polymerization initiator and tin (II) 2-ethyl hexanoate as polymerization catalyst.

As an example, a targeting moiety/agent may target or cause the particle to become localized at specific locations within a subject and the bioactive agent/therapeutic agent is thus delivered to a target site. In one embodiment, a drug or therapeutic agent can be released in a controlled release manner from the particle and allowed to interact locally with the particular targeted site (e.g., a tumor). The term "controlled release" (and variations of that phrase (e.g., in the context of "controlled-release system")) is generally meant to encompass release of a therapeutic agent (e.g., a drug) at a selected site in a controllable rate, interval, and/or amount. "Controlled release" encompasses, but is not necessarily limited to, substantially continuous delivery, patterned delivery (e.g., intermittent delivery over a period of time that is interrupted by regular or irregular time intervals) or delivery of a bolus of a selected therapeutic agent (or various combinations thereof) as a predetermined, discrete amount over a relatively short period of time (e.g., a few seconds or minutes).

Examples of second biocompatible and biodegradable hydrophobic polymer blocks that can be used in the manufacture of the claimed nanoparticles can be polyesters. Exemplary polyesters suitable for use in the manufacture of the disclosed nanoparticles include copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof. In some embodiments, polyesters include, for example, polyanhydrides, poly(ortho ester) PEGylated poly(ortho ester), poly(caprolactone), PEGylated poly(caprolactone), poly(L-lactide-co-L-lysine), poly(serine ester), poly(4-hydroxy-L-proline ester), poly[a-(4-aminobutyl)-L-glycolic acid], and derivatives thereof.

Second biocompatible and biodegradable hydrophobic polymer block (e.g., polyesters) utilized in the manufacture of the disclosed nanoparticles can contain functional groups that react with the $\omega$ terminus of the poly(ethylene glycol). Non-limiting examples of such functional groups include, and are not limited to, amines, hydroxyl groups, carboxylic acid groups, NHS groups, alkyne groups or azide groups. Groups with which the second biocompatible and biodegradable hydrophobic polymer block functional groups react at the $\omega$ terminus of the poly(ethylene glycol) polymer are provided in the following table.

| Polyester functional group | Reactive group at the $\omega$ terminus of poly(ethylene glycol) |
|---|---|
| N-hydroxysuccinimide (NHS) | Amine |
| Amine | Hydroxyl, Carboxylic acid |
| Hydroxyl | Amine |
| Carboxylic acid | Amine |
| Alkyne | Azide |

Targeting agents disclosed herein can contain, or be modified to contain, a functional group that can be reacted with the $\alpha$ terminus of a polymer (e.g., PEG) in order to produce a polymer conjugated to a targeting moiety. The functional groups include any moiety that can be used to create a covalent bond with a polymer (e.g., PEG), such as amino, hydroxy, azide, alkyne and thio. For example, targeting agents can be can be substituted with NH$_2$, SH or OH, which are either bound directly to the targeting agent or via an additional group, e.g., alkyl or phenyl. In a non-limiting example, aniline, alkyl-NH$_2$ (e.g., (CH$_2$)$_{1-6}$NH$_2$), or alkyl-SH (e.g., $(CH_2)_{1-6}NH_2$) can be used to link the targeting agent to a polymer via the free $NH_2$ and SH groups to form a covalent bond.

The conjugation of a functionalized PEG polymer (a PEG polymer comprising one or more targeting agents at its α terminus and reactive functional groups at the ω terminus) and a second biocompatible and biodegradable hydrophobic polymer can be performed according to methods known in the art via functional groups at the ω terminus of a functionalized PEG polymer and reactive groups present in the second biocompatible and biodegradable hydrophobic polymer. For example, EDC-NHS chemistry (1-ethyl-3-(3-dimethylaminopropyl) carbodiimide hydrochloride and N-hydroxysuccinimide) or a reaction involving a maleimide or a carboxylic acid can be used. The conjugation of a poly(ester) and a poly(ether) to form a poly(ester-ether), can be performed in an organic solvent, such as, but not limited to, dichloromethane, acetonitrile, chloroform, dimethylformamide, tetrahydrofuran, acetone, or the like. Specific reaction conditions can be determined by those of ordinary skill in the art using no more than routine experimentation.

The conjugation of a functionalized PEG polymer (a PEG polymer comprising one or more targeting agents (TA) at its α terminus and reactive functional groups at the ω terminus) and a second biocompatible and biodegradable hydrophobic polymer can also be performed using chemistries that are orthogonal to the amide bond forming EDC-NHS chemistry. Such methods include "click" chemistry techniques. For example, an alkyne terminated poly(ester) may be reacted with a heterobifunctional poly(ethylene glycol) bearing a TA at its α-terminus and an alkyne reactive azide moiety at its ω-terminus. The conjugation of a poly(ester) and a poly (ether) to form a poly(ester-ether), can be performed in an organic solvent, such as, but not limited to, dichloromethane, acetonitrile, chloroform, dimethylformamide, tetrahydrofuran, acetone, or the like. Conventional "click" chemistry catalysts such as copper sulfate may be employed.

In another set of embodiments, a conjugation reaction may be performed by reacting a polymer that comprises a carboxylic acid functional group (e.g., a poly(ester-ether) compound) with a polymer or other moiety (such as a targeting moiety) comprising an amine. For instance, a targeting moiety, such as a low-molecular weight PSMA ligand, may be reacted with an amine to form an amine-containing moiety, which can then be conjugated to the carboxylic acid of the polymer. Such a reaction may occur as a single-step reaction, i.e., the conjugation is performed without using intermediates such as N-hydroxysuccinimide or a maleimide. The conjugation reaction between the amine-containing moiety and the carboxylic acid-terminated polymer (such as a poly(ester-ether) compound) may be achieved, in one set of embodiments, by adding the amine-containing moiety, solubilized in an organic solvent such as (but not limited to) dichloromethane, acetonitrile, chloroform, tetrahydrofuran, acetone, formamide, dimethylformamide, pyridines, dioxane, or dimethysulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously, in some cases. Unconjugated reactants may be washed away after such reactions, and the polymer may be precipitated in solvents such as, for instance, ethyl ether, hexane, methanol, or ethanol.

Another aspect of the invention is directed to particles that include polymer conjugates such as the ones described above. The particles may have a substantially spherical (i.e., the particles generally appear to be spherical), or non-spherical configuration. For instance, the particles, upon swelling or shrinkage, may adopt a non-spherical configuration. In some cases, the particles may include polymeric blends. For instance, a polymer blend may be formed that includes a first PEG polymer comprising a targeting moiety (i.e., a low-molecular weight PSMA ligand) and a second polymer comprising a biocompatible polymer (e.g., lacking a targeting moiety). By controlling the ratio of the first and second polymers in the final polymer, the concentration and location of targeting moiety in the final polymer may be readily controlled to any suitable degree.

As discussed above, the polymer may be PLGA in some embodiments. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In particular embodiments, by optimizing the ratio of lactic acid to glycolic acid monomers in the polymer of the nanoparticle (e.g., the PLGA block copolymer or PLGA-PEG block copolymer), nanoparticle parameters such as water uptake, therapeutic agent release (e.g., "controlled release") and polymer degradation kinetics can be optimized. Yet other embodiments provide polymers that may be one or more acrylic polymers. In certain embodiments, acrylic polymers include, for example, copolymers, methyl methacrylate copolymers, ethoxyethyl methacrylates, cyanoethyl methacrylate, aminoalkyl methacrylate copolymer, methacrylic acid alkylamide copolymer, poly(methyl methacrylate), aminoalkyl methacrylate copolymer, glycidyl methacrylate copolymers, polycyanoacrylates, and combinations comprising one or more of the foregoing polymers.

In some other embodiments, polymers can be cationic polymers. In general, cationic polymers are able to condense and/or protect negatively charged strands of nucleic acids (e.g. DNA, RNA, or derivatives thereof). Amine-containing polymers such as poly(lysine) (Zauner et al., 1998, *Adv. Drug Del. Rev.*, 30:97; and Kabanov et al., 1995, *Bioconjugate Chem.*, 6:7), poly(ethylene imine) (PEI; Boussif et al, 1995, *Proc. Natl. Acad. Sci., USA*, 1995, 92:7297), and poly(amidoamine) dendrimers (Kukowska-Latallo et al., 1996, *Proc. Natl. Acad. Sci., USA*, 93:4897; Tang et al., 1996, *Bioconjugate Chem.*, 7:703; and Haensler et al., 1993, *Bioconjugate Chem.*, 4:372) are positively-charged at physiological pH, form ion pairs with nucleic acids, and mediate transfection in a variety of cell lines.

In yet other embodiments, polymers can be degradable polyesters bearing cationic side chains (Putnam et al., 1999, *Macromolecules*, 32:3658; Barrera et al., 1993, *J. Am. Chem. Soc.*, 115:11010; Urn et al., 1999, *J. Am. Chem. Soc.*, 121: 5633; and Zhou et al, 1990, *Macromolecules*, 23:3399). Incorporation of hydrophobic comonomers (e.g., lactide, glycolide, caprolactone, or hydrophobic amino acids such as alanine, valine, leucine, isoleucine or phenylalanine) into the polymer backbone to an extent that will impart hydrophobic character to the copolymer enables formation of nanoparticles with a degree of cationic character within the particle core. This in turn enables encapsulation of drugs such as siRNA into the nanoparticle core. Examples of these polyesters include poly(L-lactide-co-L-lysine) (Barrera et al, 1993, *J. Am. Chem. Soc.*, 115:11010), poly(serine ester) (Zhou et al, 1990, *Macromolecules*, 23:3399), poly(4-hydroxy-L-proline ester) (Putnam et al, 1999, *Macromolecules*, 32:3658; and Lim et al, 1999, *J. Am. Chem. Soc.*, 121:5633). Poly(4-hydroxy-L-proline ester) was demonstrated to condense plasmid DNA through electrostatic interactions, and to mediate gene transfer (Putnam et al, 1999, *Macromolecules*, 32:3658; and Lim et al, 1999, *J. Am. Chem. Soc.*, 121:5633). These new polymers are less toxic than poly(lysine) and PEI, and they degrade into non-toxic metabolites.

In a particular embodiment, the molecular weight of the polymers of the nanoparticles of the invention are optimized for effective treatment of cancer, e.g., prostate cancer. For example, the molecular weight of the polymer influences nanoparticle degradation rate (particularly when the molecular weight of a biodegradable polymer is adjusted), solubility, water uptake, and drug release kinetics (e.g. "controlled release"). As a further example, the molecular weight of the polymer can be adjusted such that the nanoparticle biodegrades in the subject being treated within a reasonable period of time (ranging from a few hours to 1-2 weeks, 3-4 weeks, 5-6 weeks, 7-8 weeks, etc.). In particular embodiments of a nanoparticle comprising a copolymer of PEG and PLGA, the PEG has a molecular weight of 1,000-20,000 Da (e.g., 5,000-20,000, e.g., 10,000-20,000) and, in some embodiments, 5000 Da, and the PLGA has a molecular weight of 5,000-100,000 Da (e.g., 20,000-70,000, e.g., 20,000-50,000), or in some embodiments, 15,000-30,000 Da.

The nanoparticles disclosed herein can be used for the treatment of various diseases and disorders within a subject. A subject may be a human or non-human animal. Examples of subjects include, but are not limited to, a mammal such as a dog, a cat, a horse, a donkey, a rabbit, a cow, a pig, a sheep, a goat, a rat, a mouse, a guinea pig, a hamster, a primate, a human or the like.

The subject invention provides a number of methods of making nanoparticles comprising one or more targeting agent and/or one or more bioactive moiety/therapeutic agent. In various aspects of the invention, a functionalized targeting agent conjugated diblock copolymer is synthesized by initiating the polymerization of biocompatible and biodegradable hydrophobic polymer (such as poly(ester)) from the ω terminus of the poly(ethylene glycol). Scheme 1 illustrates this process as exemplified by a poly(ethylene glycol) bearing a hydroxyl functional group on its α-terminus and targeting agent (TA) on its ω-terminus. Polymerization of a poly(ester) block from this hydroxyl terminus yields the desired diblock copolymer bearing a TA covalently bound to its PEG terminus.

Scheme 1. Method for synthesis of Poly(ester)-block-poly(ethylene glycol) bearing a targeting agent (TA) at its PEG terminus

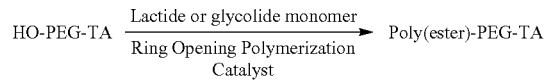

PEG = poly(ethylene glycol)
TA = Targeting agent
Poly(ester) includes poly(D, L-lactide), poly(L-lactide), poly(D, L-lactide-co-glycolide)

Alternatively, a diblock copolymer bearing a targeting agent (TA) on its poly(ethylene glycol) terminus may be prepared by conjugation of a suitably protected form of the targeting agent (TA-PRO) to the poly(ethylene glycol) polymer (yielding HO-PEG-TA(PRO)), and subsequently using this macroinitiator in the ring opening polymerization of a cyclic lactone monomer such as lactide, glycolide or a mixture thereof. Removal of the protecting groups of the targeting agent using standard deprotection methodology provides the desired Poly(ester)-block-PEG-TA (see scheme 2).

Alternatively, a functional diblock copolymer (Poly(ester)-PEG-TA) may be prepared by the covalent coupling of the targeting PEG-TA to a pre-formed poly(ester). For example, a carboxylic acid terminated poly(lactide-co-glycolide) (Poly(ester)-CO$_2$H) and poly(ethylene glycol) bearing the targeting agent on its α-terminus and an acid reactive amino functional group on its ω-terminus (H$_2$N-PEG-TA) may be reacted under organic solvent conditions.

Scheme 2. Method for synthesis of Poly(ester)-block-poly(etheylene glycol) bearing a targeting agent (TA) at its PEG terminus using the protected form of the targeting agent (HO-PEG-TA(PRO)) as a macroinitiator in the ring opening polymerization of a cyclic lactone monomer

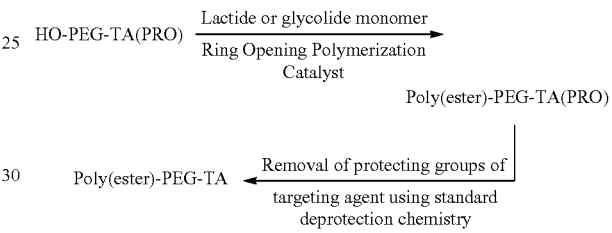

PEG = poly(ethylene glycol)
TA = Targeting agent
TA(PRO) = Protected form of the targeting agent
Poly(ester) includes poly(D, L-lactide), poly(L-lactide), poly(D, L-lactide-co-glycolide)

Targeting agents (TA's) may be comprised of individual natural or non-natural amino acids, or a combination of two or more amino acid residues covalently bound either by a amide or a urea linkage. TA's may also be comprised of nucleic acids. As such, TA's may contain side chain moieties bearing functional groups including carboxylic acids, amines, thiols, alcohols, phenols, guanidine, purines (such as adenine, guanine), pyrimidines (such as cytosine, uracil, thymine). The method of scheme 2 is preferred over the method of scheme 1 when TA's contain functional groups that may either initiate a ring opening polymerization (such as an alcohol, a phenol, an amine, or a thiol) or react with and structurally alter the polymerization catalyst (such as guanidine, 1,5-pentandioic acid moieties as found when a dipeptide or polypeptide TA has a glutamic acid residue on its C-terminus, or a urea linkage capable of binding to the polymerization catalyst).

This invention also describes methods for the synthesis of covalent conjugates of heterobifunctional poly(ethylene glycol) and targeting agents (TA's). Poly(ethyleneglycol) (PEG) bearing a hydroxyl group at its α-terminus and a reactive functional group on its ω-terminus such as a carboxylic acid, an aldehyde, an azide, an alkyne, a maleimido group, are described herein. Such heterobifunctional PEG's may be reacted with a TA bearing an amine, a thiol, an alkyne or an azide moiety to yield a covalent conjugate of PEG and TA (HO-PEG-TA). Preferred reactive moieties include amine and carboxylic acid and amine and aldehyde that yield naturally occurring linkages such as amides or secondary amines. Scheme 3 provides chemical synthetic methodologies to enable such covalent conjugation.

Scheme 3. Methodologies for synthesis of covalent conjugates of poly(ethylene glycol) and targeting agent (TA) or its protected analogue (TA-PRO)

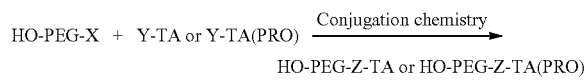

HO-PEG-Z-TA or HO-PEG-Z-TA(PRO)

PEG = poly(ethylene glycol)
TA = Targeting agent
TA(PRO) = Protected form of the targeting agent
X = carboxylic acid, aldehyde, maleimide, azide or alkyne
Y = amine, thiol, azide or alkyne
Y-TA is used when the targeting agent is free of functional groups capable of undesirable side reactions with X and/or initiating ring opening polymerization or capable of undesirable side reactions with polymerization catalysts Y-TA(PRO) is used with the targeting agent does not meet the chemical structural requirements outlined above for the use of Y-TA Conjugation chemistries include acid activation to succinimidyl ester using for example ethyl dimethylaminopropyl carbodiimide (EDC) and/or N-hydroxysuccinimide (NHS) followed by amidation reaction; reductive alkylation involving an aldehyde and amine and subsequent reduction using for example sodium cyanoborohydride; click chemistry involving and azido and alkyne moieties using for example a copper catalyst; thiol-maleimide chemistry to yield a stable secondary mercaptan This invention also describes methods for the synthesis of HO-PEG-TA(PRO) conjugates under anhydrous organic solvent condition using the preferred amidation reaction of an amine moiety of the TA(PRO) and an acid terminus of PEG. Scheme 4 illustrates the method used for covalent conjugation of HO-PEG-CO$_2$H to a allyl protected lysine-urea-glutamic acid (lys-urea-glu) targeting agent. Use of the allyl protected analog of the lys-urea-glu targeting agent improves its solubility in organic solvents most suitable (such as dichloromethane) for EDC/NHS acid activation chemistry. Amidation reaction under anhydrous organic solvent conditions enables a high degree of conjugation efficiency and yields over 80% end group functionalization in HO-PEG-lys-urea-glu(allyl protected). Furthermore, the allyl protected lys-urea-glu (TA(PRO)) enables the ring opening polymerization of lactone monomers without undesirable side reaction with the preferred polymerization catalyst (tin (II) 2-ethylhexanoate).

Scheme 4. Synthesis of HO-PEG-lys-urea-glu (allyl protected) conjugate under anhydrous organic solvent conditions using EDC/NHS activation of the acid terminus of PEG followed by amidation by reaction with the amine moiety of TA(PRO)

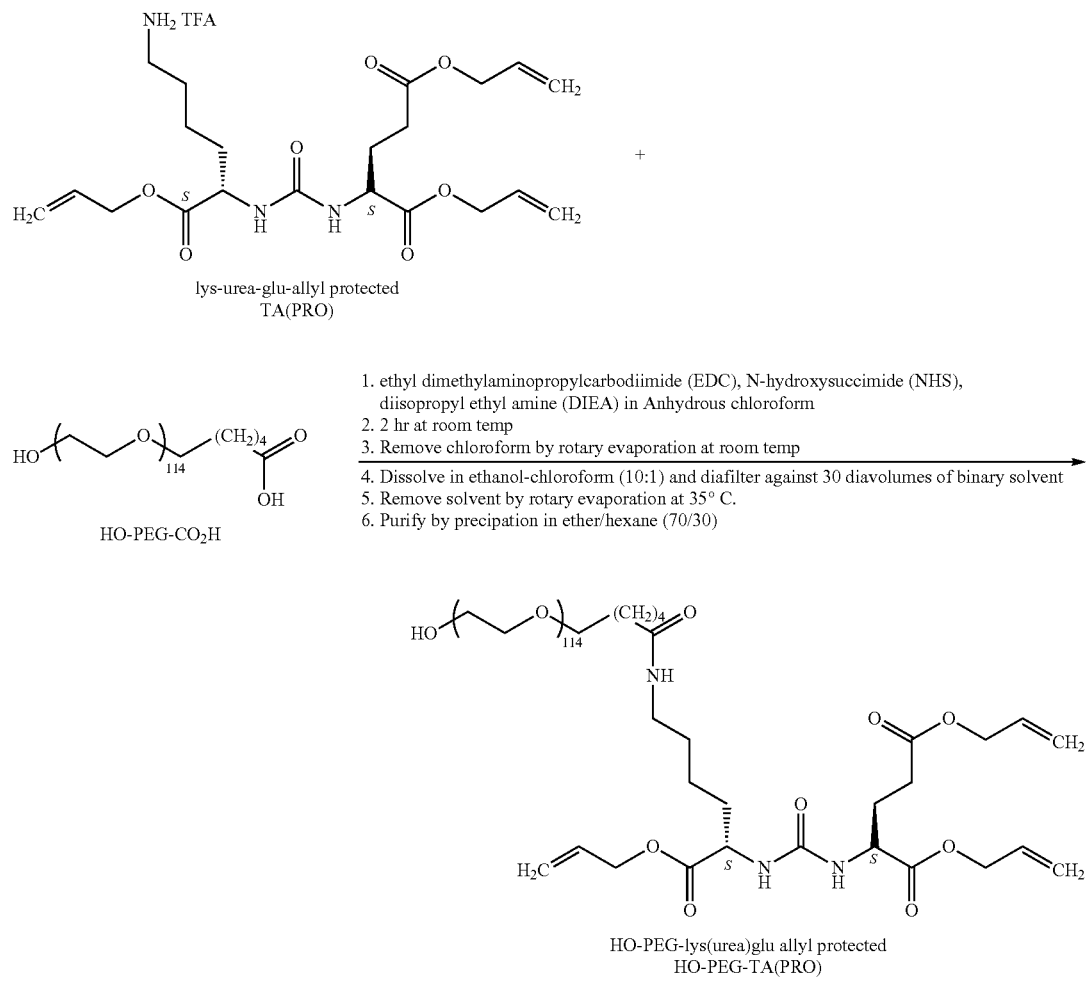

This invention also describes methods for the synthesis of HO-PEG-TA(PRO) conjugates under organic solvent conditions using reductive alkylation reaction of an amine moiety of the TA(PRO) and an aldehyde terminus of PEG. Scheme 5 illustrates the method used for covalent conjugation of HO-PEG-CHO to allyl protected lysine-urea-glutamic acid (TA(PRO)). Use of the allyl protected analog of the lys-urea-glu targeting moiety improves its solubility in organic solvents (such as dichloromethane, dimethylformamide) suitable for reductive alkylation chemistry. Reductive alkylation under organic solvent conditions enables a high degree of conjugation efficiency and yields over 80% end group functionalization in HO-PEG-lys-urea-glu(allyl protected).

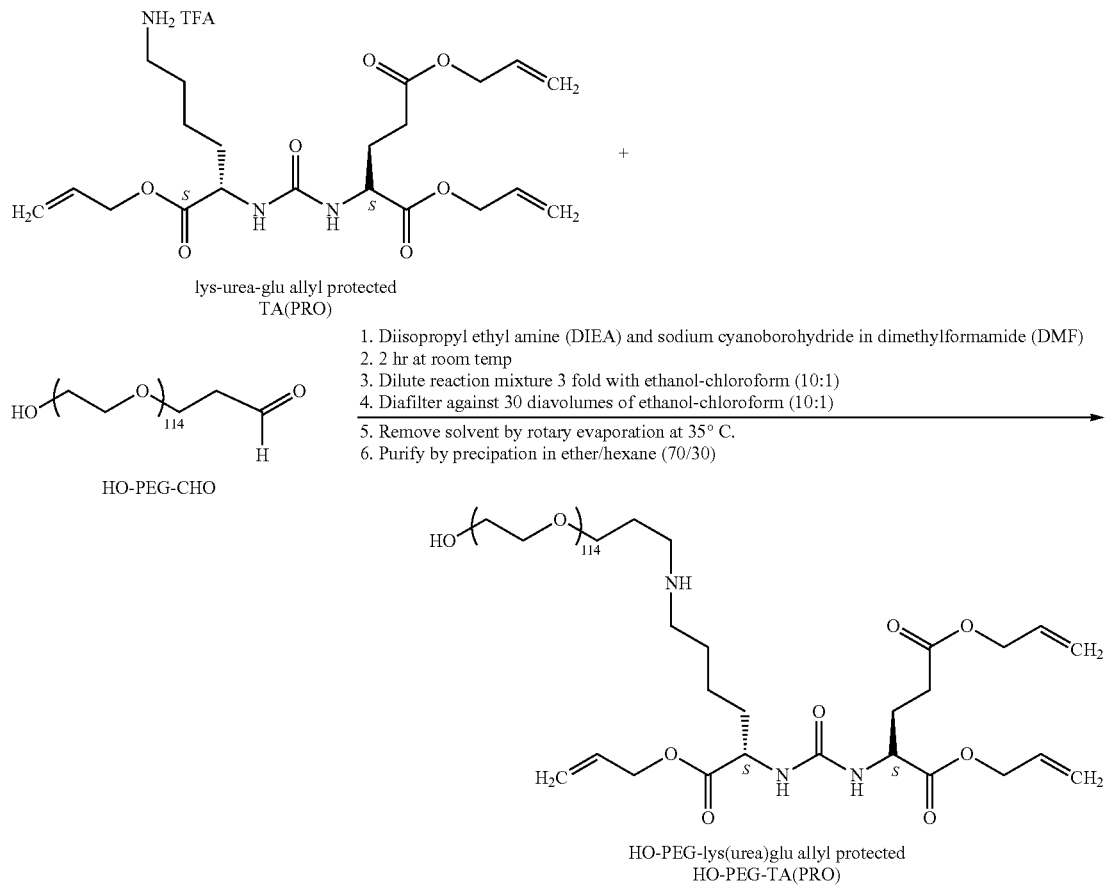

Scheme 5. Synthesis of HO-PEG-lys-urea-glu (allyl protected) conjugate under organic solvent conditions using reductive animation involving the amine moiety of the protected targeting agent (TA(PRO)) and aldehyde terminus of PEG This invention also describes the ring opening polymerization of cyclic lactone monomers using the HO-PEG-lys(urea)glu(allyl protected) (HO-PEG-TA(PRO)) conjugate as a macroinitiator and tin(II) 2-ethyl hexanoate as polymerization catalyst under monomer melt conditions at 130° C. (scheme 6), this method is also referred to as the "polymerization from" approach. For example, poly(D,L-lactide)-block-poly(ethylene glycol)-lys-urea-glu(allyl protected) obtained by such polymerization is then converted to poly(D,L-lactide)-block-poly(ethylene glycol)-lys-urea-glu by removal of the allyl protecting groups using organic base (morpholine) and tetrakis(triphenylphosphine) palladium (0) as catalyst (scheme 7). The deprotection reaction conditions are optimized with regards to molar equivalents of morpholine, palladium catalyst and reaction time to enable quantitative removal of allyl protecting groups (>98%, determined by NMR spectroscopy), without any measurable reduction in the molar mass (as determined by size exclusion chromatography and dilute solution viscometry) of the block copolymer.

Scheme 6. Synthesis of Poly (D,L-lactide)-b-PEG-lys-urea-glu(allyl protected) conjugate by ring opening polymerization of D,L-lactide under monomer melt conditions at 130° C. using HO-PEG-PEG-lys-urea-glu(allyl protected) as macroinitiator and tin (II) 2-ethylhexanoate as polymerization catalyst.

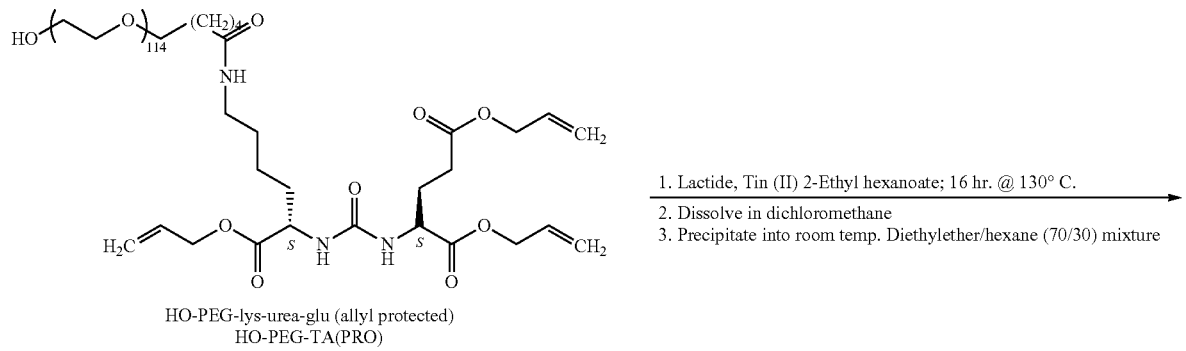

1. Lactide, Tin (II) 2-Ethyl hexanoate; 16 hr. @ 130° C.
2. Dissolve in dichloromethane
3. Precipitate into room temp. Diethylether/hexane (70/30) mixture HO-PEG-lys-urea-glu (allyl protected)
HO-PEG-TA(PRO)

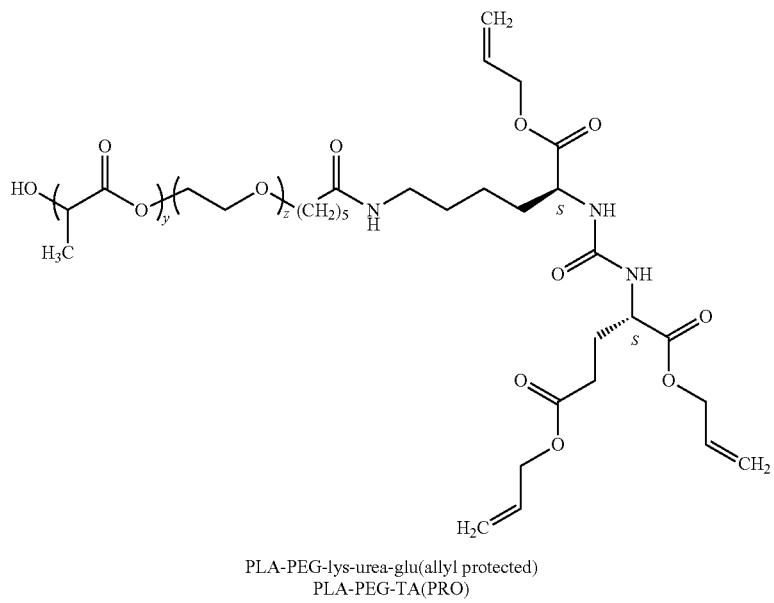

PLA-PEG-lys-urea-glu(allyl protected)
PLA-PEG-TA(PRO)

y = 222; z = 114

This application also describes the removal of residual palladium from the functionalized diblock copolymer PLA-PEG-lys-urea-glu (PLA-PEG-TA). Scheme 8 shows the chemical structures of several commercially available resins used for scavenging palladium contaminants. Trimercaptotriazine (TMT) functional resin is preferred for the removal of palladium from PLA-PEG-lys-urea-glu samples with minimal loss of polymer yield in the palladium removal step. Yield loss is observed when resins functionalized with palladium binding moieties other than TMT are used. This is due to interaction between the resin bound palladium binding moieties and the TA in PLA-PEG-TA.

Scheme 7. Conversion of Poly(D, L-lactide)-b-PEG-lys-urea-glu (allyl protected) (PLA-PEG-TA(PRO)) to PLA-PEG-PEG-lys-urea-glu (PLA-PEG-TA) using tetrakis (triphenylphosphine) palladium (0) catalyst in morpholine/dicholoromethane solution

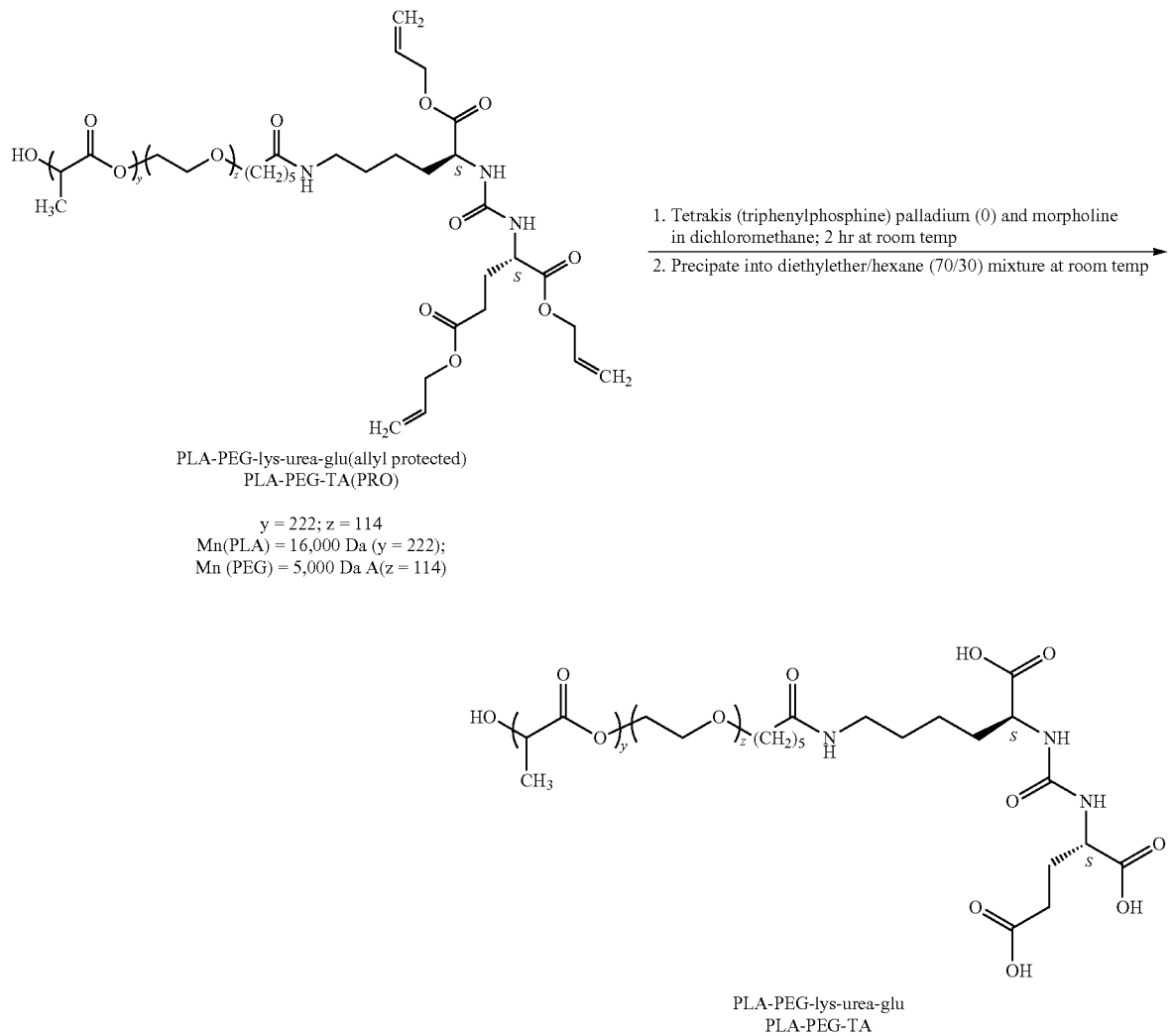

This application also describes the covalent conjugation of targeting agents (TA's) in their native unprotected form under aqueous solution conditions to heterobifunctional poly(ethylene glycol). This method utilizes the high water solubility of the targeting moiety such as lys-urea-glu or other peptide based targeting ligands. The solubility properties of the PEG-lys-urea-glu conjugate are dominated by the poly(ethylene glycol) polymer. Thus, unlike lys-urea-glu, PEG-lys-urea-glu is soluble in common organic solvents including but not limited to dichloromethane, dimethyl formamide, tetrahydrofuran, chloroform, or dimethylsulfoxide. This enables covalent coupling of the PEG-lys-urea-glu conjugate to end functional poly(ester) to yield the desired Poly(ester)-PEG-lys-urea-glu (Poly(ester)-PEG-TA) under organic solvent conditions where lys-urea-glu prior to the PEG conjugation is insoluble or sparingly soluble. This approach is referred to as the "coupling to" approach. Complete dissolution of the end functional poly(ester) and the PEG-lys-urea-glu in a common solvent is critical to obtaining a high yield of the desired Poly(ester)-PEG-TA functional block copolymer.

Scheme 8. Chemical structures of commercially available palladium scavenging resins; preferred functionally for palladium removal from PLA-PEG-lys-urea-glu is trimercaptotriazine (TMT)

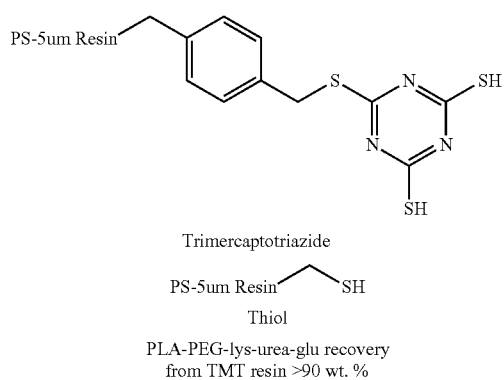

-continued

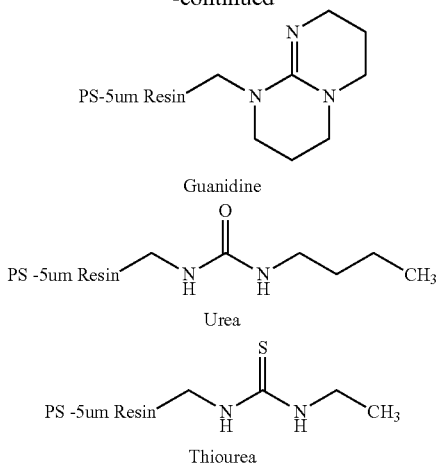

Guanidine

Urea

Thiourea

The PEG-lys-urea-glu is covalently coupled to an end functional poly(ester) using chemistries that proceed without side reactions with the carboxylic acid moieties of lys-urea-glu. For example, an α-azido-ω-carboxylic acid may be conjugated to the amino moiety of the lys-urea-glu by its reaction with the carboxy terminus of such PEG.

The targeting agent functional PEG, α-azido-ω-(lys-urea-glu)polyethylene glycol may be prepared by synthesis of a heterobifunctional precursor such as α-azido-ω-carboxy polyethylene glycol ($N_3$-PEG-$CO_2$H) from commercially available starting materials such as α-amino-ω-carboxy-poly(ethylene glycol) and for example 4-azidophenyl isothiocyanate, O-(2-azidoethyl)-O-[2-diglycolyl-amino)ethyl]heptaethylene glycol or azide-PEG4-NHS using standard conjugation methodologies (scheme 9). The heterobifunctional polymer, $N_3$-PEG-$CO_2$H is subsequently reacted with the amine functionality of lys-urea-glu under aqueous conditions using methods illustrated in scheme 10.

Scheme 9. Synthesis of $N_3$-PEG-$CO_2$H from commercially available starting materials using conventional chemistry techniques

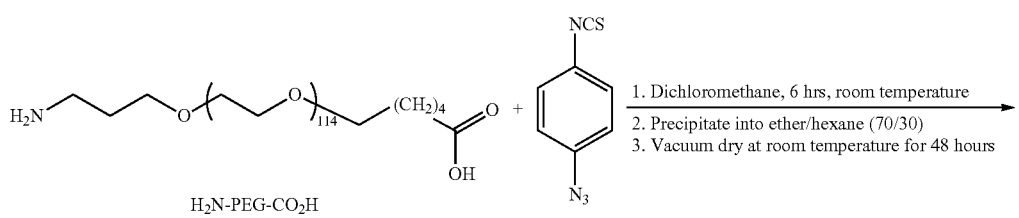

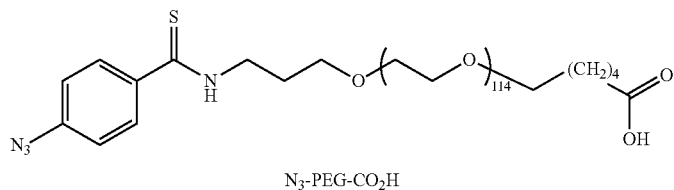

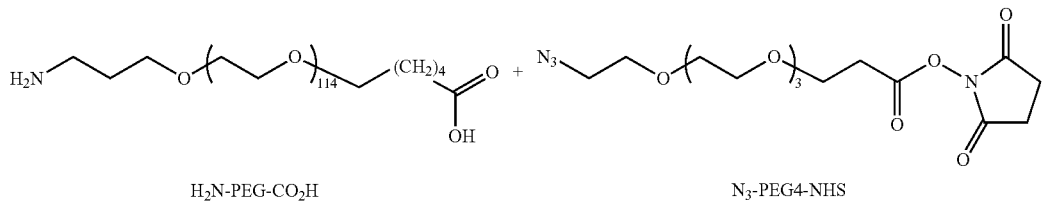

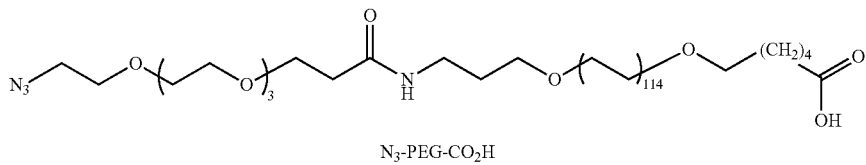

Alternatively, $N_3$-PEG-NHS may be prepared by activation of the carboxy terminus of $N_3$-PEG-$CO_2H$ under anhydrous organic solvent conditions such as in dichloromethane using organic soluble ethyldimethyl aminopropylcarbodiimide (EDC), N-hydroxysuccinimide (NHS) and diisopropyl ethylamine (DIEA) and subsequently purified by precipitation into anhydrous ether/hexane (70/30). The activated polymer ($N_3$-PEG-NHS) is then recovered by filtration and vacuum drying and stored in a dry environment under dry nitrogen (1 ppm water dry glove box for 48 hours) prior to storage at −20° C. $N_3$-PEG-NHS prepared by this method is then used to prepare $N_3$-PEG-lys-urea-glu as outlined in steps 6 through 10 of scheme 10.

1. MES buffer, pH=4.7, 20 equivalents EDC.HCl/sulfo-NHs
2. 1 hour at room temperature under stirring
3. 2-mercaptoethanol, 1 equivalent with respect to EDC.HCl
4. 5-10 minutes at room temperature under stirring
5. Purify from small molecule impurities:
   a) concentrated 50× by centrifugal filtration at 4° C.; 4000×g; 60 minutes
   b) reconstitute into DI water
   c) use this solution (A) of $N_3$-PEG-NHS (4° C.) in step 8 within 30 minutes of preparation
   $N_3$-PEG-$CO_2H$ $N_3$-PEG-lys-urea-glu
6. Dissolve lys-urea-glu (10 equivalents versus $N_3$-PEG-NHS) in bicarbonate buffer, pH=9.7
7. Adjust pH to 7.4 using 0.1N sodium hydroxide (solution B)
8. Add solution A to solution B dropwise and allow to stir at room temperature for 6 hours
9. Purify from excess lys-urea-glu as in step 5(a) (solution C)
10. Lyophilize solution C to recover $N_3$-PEG-lys-urea-glu Scheme 10. Synthesis of $N_3$-PEG-lys-urea-glu under aqueous conditions from $N_3$-PEG-$CO_2H$ using pH adjustment to maximize the yield of desired product As stated above, this application also describes the covalent coupling of $N_3$-PEG-lys-urea-glu to an end functional poly(ester) bearing a alkyne moiety at its α-terminus and a hydroxy terminus at its ω-terminus using well established "click" chemistry techniques such as using a copper sulfate catalyst under organic solvent conditions, for example in dimethylformamide (DMF) (scheme 11). This "click" chemistry methodology is particularly useful since the carboxylic acid functionalities of lys-urea-glu are not reactive towards the alkyne functionality of the poly(ester). Such orthogonal chemistry rules out possible side reactions and permits the use long reaction times between the poly(ester)-alkyne and $N_3$-PEG-lys-urea-glu. Furthermore, unlike amidation chemistry using for example Poly(ester)-NHS, "click" chemistry is not moisture sensitive, thus need for anhydrous conditions is not critical to ensure an acceptable degree of covalent conjugation that provides >80% end functionalization.

Scheme 11. Synthesis of PLA-PEG-lys-urea-glu by covalent conjugation of $N_3$-PEG-lys-urea-glu to alkyne-PLA in dimethylformamide using copper(I)bromide catalyst at 60° C.

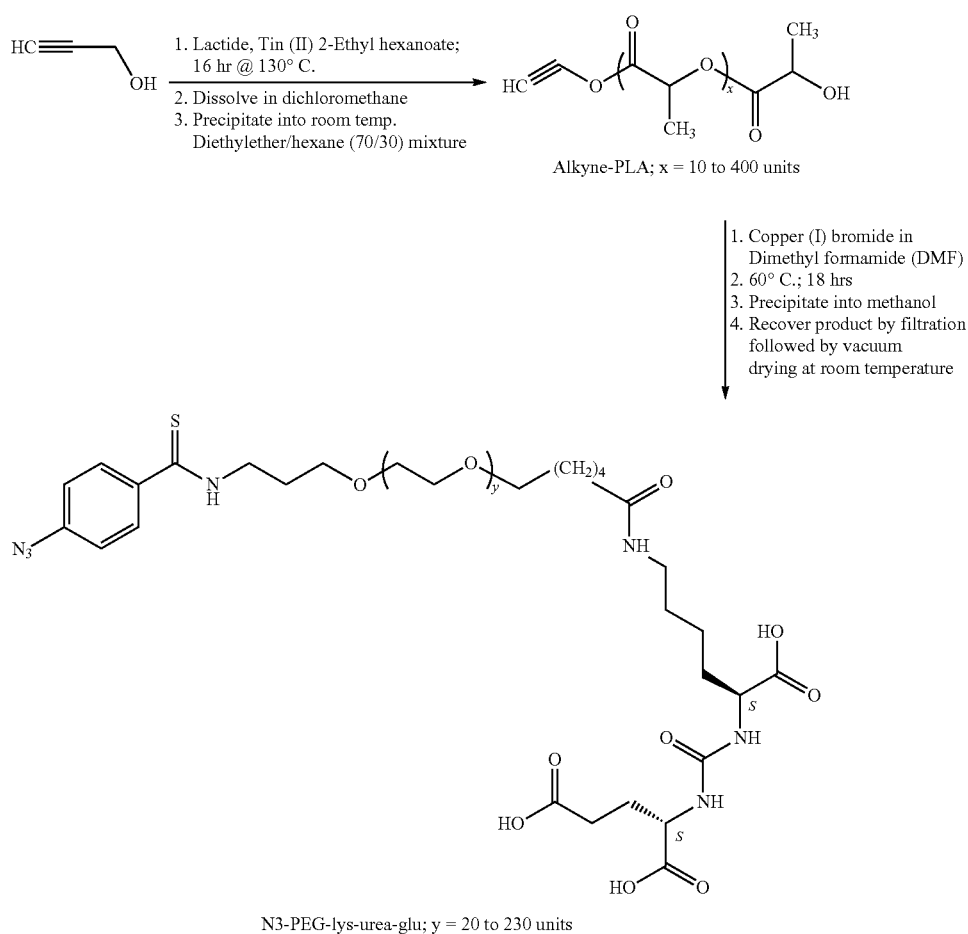

N3-PEG-lys-urea-glu; y = 20 to 230 units

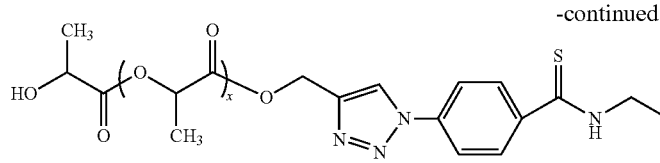
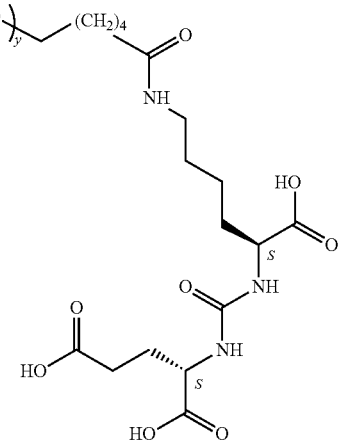

PLA-PEG-lys-urea-glu;
x = 10 to 400 units
y = 20 to 230 units

The "polymerization from" approach of scheme 6 and 7 has the following advantages:
1. Use of HO-PEG-TA(PRO) in the ring opening polymerization ensures no cross-reactivity between the functional groups of TA polymerization catalyst or monomer thereby avoiding loss of control over the polymerization and contaminating byproducts.
2. Absence of side reactions allows excellent control of the molecular weight and composition of the Poly(ester)-PEG-TA(PRO)
3. Adjustment of the composition of the monomer feed and the molar ratio of the initiator to monomer enables synthesis of the poly(ester) block of a wide range of desired compositions and molecular weights. The ratio or the PEG to the poly(ester) may also be varied at with ease.
4. The PLA-PEG-TA(PRO) is soluble in common dueterated organic solvents used for NMR spectroscopy such as chloroform-d, DMSO-d6, DMF-d7, or THF-d4. This enables NMR analysis of Poly(ester)-PEG-TA(PRO) providing quantitative information regarding critical polymer characteristics such as extent of TA(PRO) end group on Poly(ester)-PEG-TA(PRO) as well as absolute number average molecular weight ($M_n$). Provided relative molar mass (determined by for example size exclusion chromatography or inherent viscosity) of Poly(ester)-PEG-TA is equivalent to that of its protected precursor (Poly(ester)-PEG-TA(PRO)), the absolute $M_n$ of Poly(ester)-PEG-TA(PRO) (determined by NMR spectroscopy) may be considered equal to that of its precursor. This enables precise determination of polymer characteristic.
5. Precise determination of Poly(ester)-PEG-TA characteristic such as its absolute $M_n$ and the extent of TA end group functionalization are critical for controlling the targeting properties of the nanoparticles made from Poly(ester)-PEG-TA. Such nanoparticles are prepared by blending known quantities of this functional polymer (Poly(ester)-PEG-TA) with non-functional polymer (Poly(ester)-PEG) to control the degree of targeting agent within the therapeutic nanoparticle.

The "polymerization from" approach of scheme 6 and 7 has the following shortcomings:
1. It requires the functional groups of the TA to be protected. This may require use of expensive and/or difficult to obtain starting materials when TA is based on 2 or more amino acid residues or nucleic acids containing side chain moieties that may interfere with the ring opening polymerization.
2. It necessitates removal of the protecting groups of TA(PRO) to yield the desired Poly(ester)-PEG-TA. The deprotection reaction may require use of a heavy metal catalyst that needs to be removed from the final product. This adding a purification step to the process that may in some cases be difficult to achieve with sufficient efficiency so as to provide a polymeric material of pharmaceutically acceptable purity.

The "coupling to" approach has the following advantages:
1. It does not require potentially expensive protected analogues of the targeting agent (TA(PRO)'s)
2. It does not require the deprotection of the TA(PRO) to obtain the desired Poly(ester)-PEG-TA polymer thereby avoiding associated shortcomings as described previously.

The "coupling to" approach has the following shortcomings:
1. It relies on coupling pre-made end functional poly(ester)s to PEG-TA, hence control over the composition and molecular weight of the poly(ester) requires synthesis of poly(ester)s of various desired properties in advance of the coupling reaction.
2. Coupling of macromolecular entities such as an end functional Poly(ester) and PEG-TA is slow due to poor diffusion characteristic of polymers and requires long reaction times at high reagents concentrations to ensure acceptable coupling efficiencies (>80%).
3. The method yields Poly(ester)-PEG-TA. Diblock copolymers bearing TA's as an end group are difficult to analyze by NMR spectroscopy due to differences in solubility characteristics of the poly(ester)-PEG polymer and the TA. Thus, quantitative analysis of end group functionality and absolute $M_n$ is difficult using conventional methods such NMR spectroscopy.

In view of the advantages and shortcoming of the "polymerization from" and "coupling to" approaches, the latter is preferred over the former only when the TA(PRO) is expensive and/or difficult to obtain or the deprotection conditions are difficult or irreversibly contaminate the final polymeric product. Otherwise, the "polymerization from" approach is preferred due to ease of access to a large variety of polymer architectures and compositions as well as ease of analytical characterization of the Poly(ester)-PEG-TA(PRO) and hence the final product (Poly(ester)-PEG-TA) in cases where equivalence of polymer architecture may be established by other non-absolute yet dependable analytical methods.

The self-assembly of the poly(ester)-PEG-X diblock copolymers in aqueous medium yields nanoparticles comprising a hydrophobic core and a hydrophilic poly(ethylene glycol) corona (exterior). The hydrophobic core bears the bioactive/therapeutic agent while the hydrophilic corona presents the targeting agent on the nanoparticle surface and enables the nanoparticles to selectively bind to target sites (e.g., diseased tissue) via interaction of the targeting agent with a corresponding agent expressed at the target site.

Chemical Structures of abbreviations used:

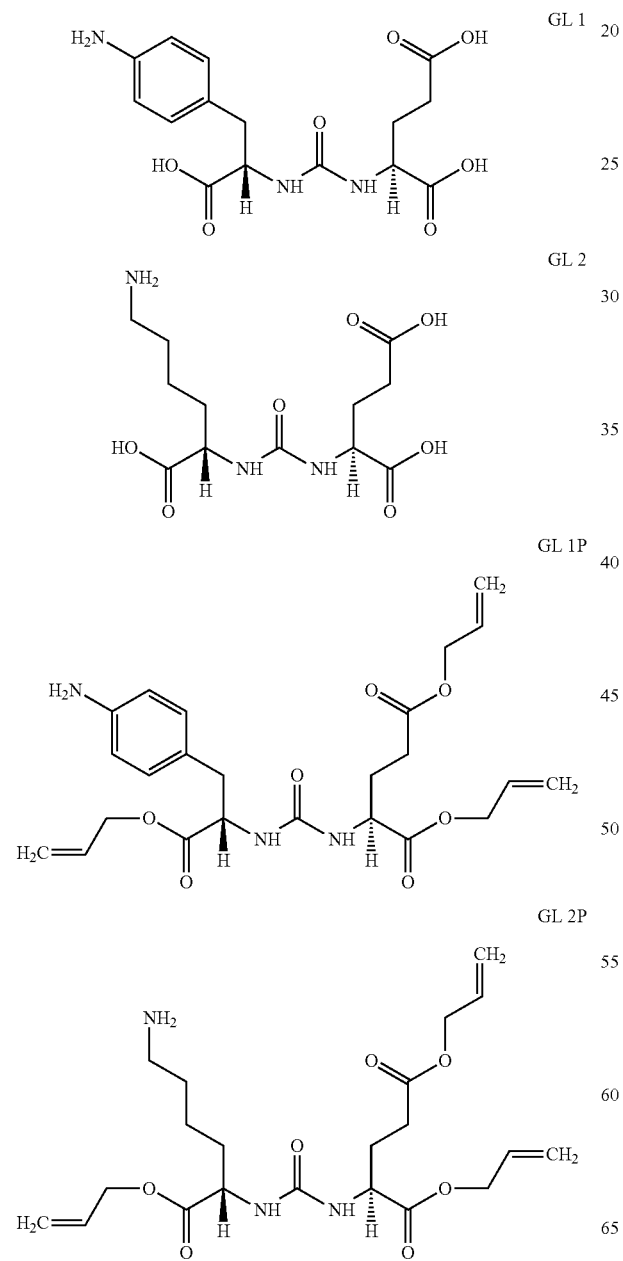

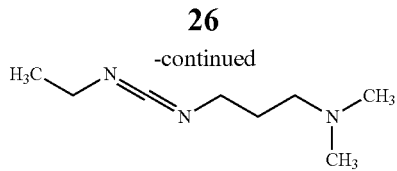

EDC

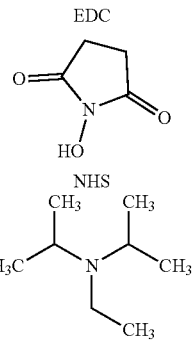

NHS

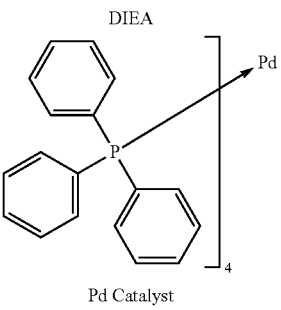

DIEA

Pd Catalyst

Bioactive Moieties/Therapeutic Agents

As discussed above, therapeutic agents (bioactive moieties) can be incorporated into the hydrophobic nanoparticle core in aqueous medium or organic solvents and the nanoparticles can be, subsequently, purified. Bioactive agents (therapeutic agents) include, and are not limited to, therapeutic agents (e.g. anti-cancer agents), diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.). As discussed herein, bioactive agents may be administered to an individual as disclosed herein. Exemplary therapeutic agents to be delivered in accordance with the present invention include, but are not limited to, small molecules (e.g. cytotoxic agents), nucleic acids (e.g., siRNA, RNAi, and microRNA agents), proteins (e.g. antibodies), peptides, lipids, carbohydrates, hormones, metals, radioactive elements and compounds, drugs, vaccines, immunological agents, etc., and/or combinations thereof. In some embodiments, the agent to be delivered is an agent useful in the treatment of cancer (e.g., prostate cancer).

Some examples of therapeutic agents that can be delivered within the nanoparticles produced in accordance with the disclosed methods include, but are not limited to agents such as penicillins, aminopenicillins, penicillins in conjunction with penicillinase inhibitor and/or anti-fungal agents), cephalosporins, cephamycins and carbapenems, fluoroquinolones, tetracyclines, macrolides and aminoglycosides. Specific examples include, but are not limited to, erythromycin, bacitracin zinc, polymyxin, polymyxin B sulfates, neomycin, gentamycin, tobramycin, gramicidin, ciprofloxacin, trimethoprim, ofloxacin, levofloxacin, gatifloxacin, moxifloxacin, norfloxacin, sodium sulfacetamide, chloramphenicol, tetracycline, azithromycin, clarithyromycin, trimethoprim sulfate and bacitracin.

Yet other examples of therapeutic agents suitable for inclusion within the disclosed nanoparticles are non-steroidal (NSAIDs) and steroidal anti-inflammatory agents (generally referred to as anti inflammatory agents (including both COX-1 and COX-2 inhibitors)). Examples include, but are not limited to, corticosteroids, medrysone, prednisolone, prednisolone acetate, prednisolone sodium phosphate, fluorometholone, dexamethasone, dexamethasone sodium phosphate, betamethasone, fluoromethasone, antazoline, fluorometholone acetate, rimexolone, loteprednol etabonate, diclofenac (diclofenac sodium), ketorolac, ketorolac tromethamine, hydrocortisone, bromfenac, flurbiprofen, antazoline and xylometazoline.

Other therapeutic agents that can be incorporated into nanoparticles as disclosed herein include anti-histamines, mast cell stabilizers and other anti-allergy agents. Examples include, but are not limited, cromolyn sodium, lodoxamide tromethamine, olopatadine HCl, nedocromil sodium, ketotifen fumarate, levocabastine HCL, azelastine HCL, pemirolast (pemirolast potassium), epinastine HCL, naphazoline HCL, emedastine, antazoline, pheniramine, sodium cromoglycate, N-acetyl-aspartyl glutamic acid and amlexanox.

Other non-limiting examples of potentially suitable therapeutic agents for incorporation into nanoparticles include anti-cancer agents such as 5-fluorouracil (5-FU), CPT-11, 10-hydroxy-7-ethylcamptothecin (SN38), S-I capecitabine, ftorafur, 5' deoxyfluorouridine, UFT, eniluracil, deoxycytidine, 5-azacytosine, 5-azadeoxycytosine, allopurinol, 2-chloroadenosine, aminopterin, methylene-10-deazaminopterin (MDAM), oxaplatin, picoplatin, tetraplatin, satraplatin, platinum-DACH, ormaplatin, [SP-4-3-(R)]-[1,1cyclobutanedicarboxylato-(2-)](2 methyl-1,4-butanediamine-N,N')platinum (CI-973), and analogs thereof, 9-aminocamptothecin, 10,11-methylenedioxycamptothecin, karenitecin, 9-nitrocamptothecin, 6-[[2-(dimethylamino) ethyl]amino]-3-hydroxy-7H-indeno[2,1-c] quinolin-7-one dihydrochloride (TAS 103), L-phenylalanine mustard, ifosphamidemefosphamide, trophosphamide carmustine, epothilones A-E, tomudex, 6-mercaptopurine, 6-thioguanine, karenitecin, acyclovir, valacyclovir, ganciclovir, amantadine, rimantadine, lamivudine, zidovudine, bevacizumab, trastuzumab, rituximab, 20-epi-1α, 25 dihydroxyvitamin D3, 4-ipomeanol, 5-ethynyluracil, 9-dihydrotaxol, abiraterone, acivicin, aclarubicin, acodazole hydrochloride, acronine, acylfiilvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizding morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisazuidinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caraceraide, carbetimer, carboplatin, carboxamide-amino-triazole, carboxyamidotriazole, methylglyoxal malemide, carmustine, earn 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflomithine, eflomithine hydrochloride, elemene, elsarnitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide, lobaplatin, lombricine, lometrexol, lometrexol sodium, lomustine, lonidamine, losoxantrone, losoxantrone hydrochloride, lovastatin, loxoribine, lurtotecan, lutetium texaphyrin lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/mycobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazorurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinarnide, RNAi, rogletimide, rohitukine, romurtide, roquinimex, rubiginone Bl, ruboxyl, safingol, safingol hydrochloride, saintopin, sarcnu, sarcophytol A, sargramostim, SDI1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosafe sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride and combinations thereof.

In one embodiment, the nanoparticles of this invention can contain siRNA as a therapeutic agent. Preferably, the siRNA molecule has a length from about 10-50 or more nucleotides. More preferably, the siRNA molecule has a length from about 15-45 nucleotides. Even more preferably, the siRNA molecule has a length from about 19-40 nucleotides. Even more preferably, the siRNA molecule has a length of from about 21-23 nucleotides. The siRNA of the invention preferably mediates RNAi against a target mRNA. The siRNA molecule can be designed such that every residue is complementary to a residue in the target molecule. Alternatively, one or more substitutions can be made within the molecule to increase stability and/or enhance processing activity of said molecule. Substitutions can be made within the strand or can be made to residues at the ends of the strand.

siRNA molecules used as therapeutic agents in the disclosed nanoparticles can be modified to improve stability either in vivo or in vitro. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference. For example, the absence of a 2' hydroxyl may significantly enhance the nuclease resistance of the siRNAs.

Commercially available design tools and kits, such as those available from Ambion, Inc. (Austin, Tex.), and the Whitehead Institute of Biomedical Research at MIT (Cambridge, Mass.) allow for the design and production of siRNA. By way of example, a desired mRNA sequence can be entered into a sequence program that will generate sense and antisense target strand sequences. These sequences can then be entered into a program that determines the sense and antisense siRNA oligonucleotide templates. The programs can also be used to add, e.g., hairpin inserts or T1 promoter primer sequences. Kits also can then be employed to build siRNA expression cassettes.

In various embodiments, siRNAs are synthesized in vivo, in situ, and in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the siRNAs. Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses siRNAs from a recombinant construct may be produced by introducing the construct into a zygote, an embryonic stem cell, or another multipotent cell derived from the appropriate organism.

In one embodiment, the siRNA molecules target mRNA encoding at least one a cellular protein (e.g., a nuclear, cytoplasmic, transmembrane, or membrane-associated protein). In another embodiment, the siRNA molecules target mRNA encoding one or more extracellular protein (e.g., an extracellular matrix protein or secreted protein). Thus, target mRNA can encode developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2. CBL, CSFIR, ERBA, ERBB, EBRB2, ERBB2, ERBB3, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor suppressor proteins (e.g., APC, BRCA1, BRCA2, MADH4, MCC, NF 1, NF2, RB 1, TP53, or WTI); and enzymes (e.g., ACC synthases and oxidases, ACP desaturases and hydroxylases, ADPglucose pyrophorylases, acetylases and deacetylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases or xylanases). Target mRNA can also encode proteins involved in tumor growth (including vascularization) or in metastatic activity or potential (e.g., cell surface receptors and their ligands). Target mRNA can also encode one or more secreted protein, cell cycle regulatory protein, gene regulatory protein, apoptosis regulatory protein, or proteins involved in the immune response, inflammation, complement cascade, or clotting systems. Additional examples of target mRNA against which siRNA constructs can designed include c-myc, c-myb, mdm2, PKA-I (protein kinase A type I), Ras, c-Raf kinase, CDC25 phosphatases, cyclins, cyclin dependent kinases (cdks), telomerase, PDGF/sis and mos. siRNA can also be used to target the mRNA encoded by a fusion gene that results from chromosomal translocation, for example, the Bcr/Abl fusion oncogene. siRNA can also be targeted against mRNA encoding proteins such as cyclin dependent kinases, proliferating cell nuclear antigen (PCNA), transforming growth factor-beta (TGF-beta), nuclear factor kappa B (NF-κB), E2F, HER-2/neu, PKA, TGF-alpha, EGFR, TGF-beta, IGFIR, P12, MDM2, VEGF, MDR, transferring, ferritin, ferritin receptor, transferring receptor, IRE, C-fos, HSP27, metallothionein.

Targeting Agents

As noted above, nanoparticles produced by the instant invention can also incorporate one or more targeting agent via the functionalized PEG moieties. Suitable targeting agents include, for example, antibodies and polypeptides that bind to polypeptides that are commonly overexpressed by tumor or cancer cells. Non-limiting examples of such polypeptides are epidermal growth factor receptor (EGFR), somatostatin receptor (SSTR), insulin-like growth factor receptor, folic acid-receptor, HER2 receptor, interleukin-13 receptor, gas-trin-releasing peptide receptor, CD30, vasoactive intestinal peptide receptor, gastrin receptor, prostate-specific antigen, and the estrogen receptor.

Another example of a targeting agents suitable for coupling to the disclosed nanoparticles via functionalized PEG are small molecule ligands. Such small molecule ligands can be used to target cancers that express particular target proteins. For example, for tumors or cancers that express prostate specific membrane antigen (PSMA) (including, but not limited to, prostate cancer, non-small cell lung cancer, colorectal carcinoma, and glioblastoma, and solid tumors expressing PSMA in the tumor neovasculature), PSMA ligands can be used. In some embodiments, the low-molecular weight PSMA ligand is of the Formulae I, II, III or IV:

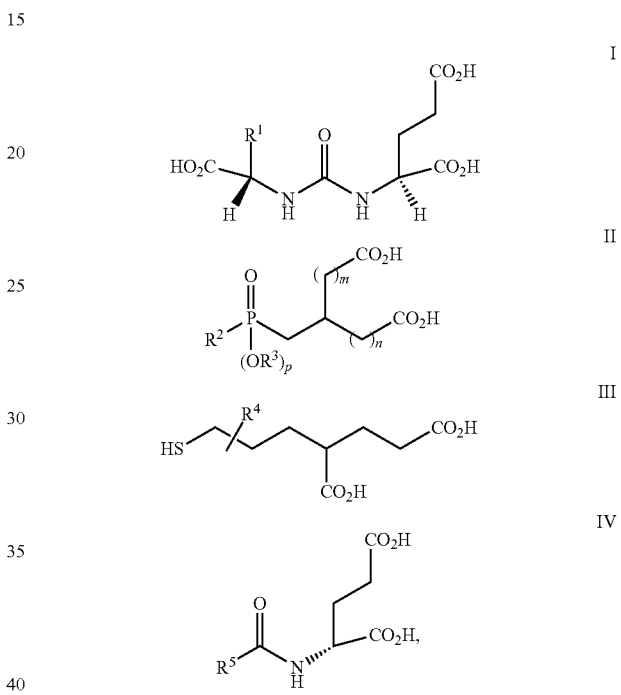

and enantiomers, stereoisomers, rotamers, tautomers, diastereomers, or racemates thereof;

wherein m and n are each, independently, 0, 1, 2 or 3;

p is 0 or 1;

$R^1$, $R^2$, $R^4$ and $R^5$ are each, independently, selected from the group consisting of substituted or unsubstituted alkyl (e.g., $C_{1-10}$-alkyl, $C_{1-6}$-alkyl, or $C_{1-4}$-alkyl), substituted or unsubstituted aryl (e.g., phenyl or pyrdinyl), and any combination thereof; and $R^3$ is H or $C_{1-6}$-alkyl (e.g., $CH_3$).

For compounds of Formulae I, II, III and IV, $R^1$, $R^2$, $R^4$ and $R^5$ comprise points of attachment to the nanoparticle within the PEG portion of the nanoparticle. The point of attachment may be formed by a covalent bond, ionic bond, hydrogen bond, a bond formed by adsorption including chemical adsorption and physical adsorption, a bond formed from van der Waals bonds, or dispersion forces. For example, if $R^1$, $R^2$, $R^4$ or $R^5$ are defined as an aniline or $C_{1-6}$-alkyl-$NH_2$ group, any hydrogen (e.g., an amino hydrogen) of these functional groups could be removed such that the low-molecular weight PSMA ligand is covalently bound to the polymeric matrix (e.g., the PEG-block of the polymeric matrix) of the nanoparticle. As used herein, the term "covalent bond" refers to a bond between two atoms formed by sharing at least one pair of electrons.

In particular embodiments of the Formulae I, II, III or IV, $R^1$, $R^2$, $R^4$ and $R^5$ are each, independently, $C_{1-6}$-alkyl or phenyl, or any combination of $C_{1-6}$-alkyl or phenyl, which are independently substituted one or more times with OH, SH, $NH_2$, or $CO_2H$, and wherein the alkyl group may be interrupted by N(H), S or O. In another embodiment, $R^1$, $R^2$, $R^4$ and $R^5$ are each, independently, $CH_2$-Ph, $(CH_2)_2$—SH, $CH_2$—SH, $(CH_2)_2C(H)(NH_2)CO_2H$, $CH_2C(H)(NH_2)CO_2H$, $CH(NH_2)CH_2CO_2H$, $(CH_2)_2C(H)(SH)CO_2H$, $CH_2$—N(H)-Ph, O—$CH_2$-Ph, or O—$(CH_2)_2$-Ph, wherein each Ph may be independently substituted one or more times with OH, $NH_2$, $CO_2H$ or SH. For these formulae, the $NH_2$, OH or SH groups serve as the point of covalent attachment to the nanoparticle (e.g., —N(H)-PEG, —O-PEG, or —S-PEG).

In still another embodiment, the low-molecular weight PSMA ligand is selected from the group consisting of:

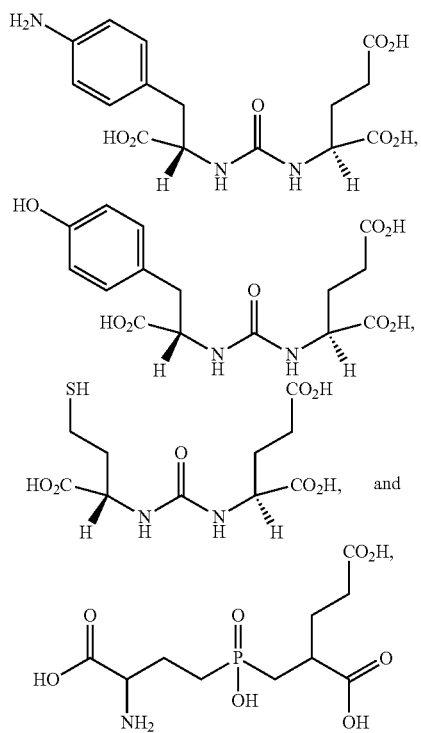

and enantiomers, stereoisomers, rotamers, tautomers, diastereomers, or racemates thereof, and wherein the $NH_2$, OH or SH groups serve as the point of covalent attachment to the nanoparticle (e.g., —N(H)-PEG, —O-PEG, or —S-PEG).

In another embodiment, the low-molecular weight PSMA ligand is selected from the group consisting of:

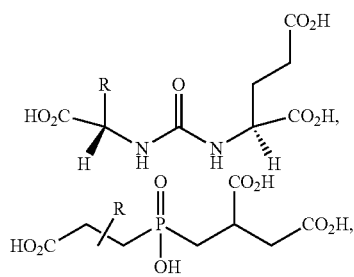

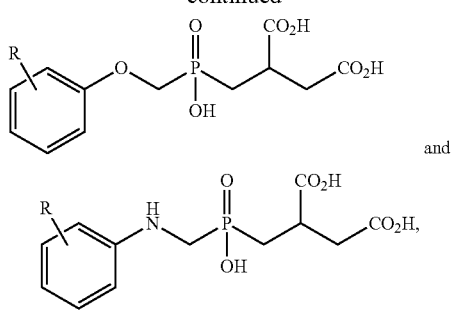

and enantiomers, stereoisomers, rotamers, tautomers, diastereomers, or racemates thereof, wherein R is independently selected from the group consisting of $NH_2$, SH, OH, $CO_2H$, $C_{1-6}$-alkyl that is substituted with $NH_2$, SH, OH or $CO_2H$, and phenyl that is substituted with $NH_2$, SH, OH or $CO_2H$, and wherein R serves as the point of covalent attachment to the nanoparticle (e.g., —N(H)-PEG, —S-PEG, —O-PEG, or $CO_2$-PEG).

In another embodiment, the low-molecular weight PSMA ligand is selected from the group consisting of:

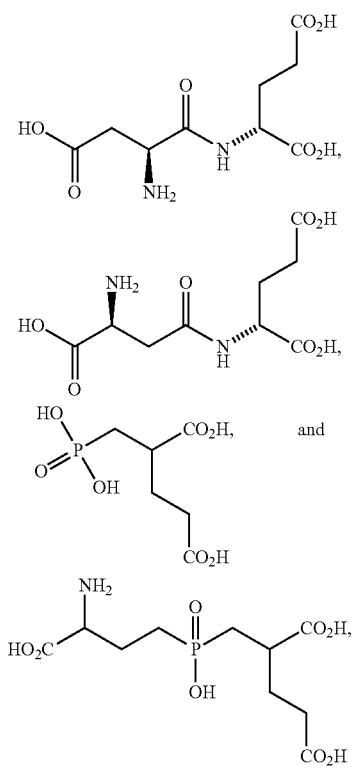

and enantiomers, stereoisomers, rotamers, tautomers, diastereomers, or racemates thereof, wherein the $NH_2$ or $CO_2H$ groups serve as the point of covalent attachment to the nanoparticle (e.g., —N(H)-PEG, or $CO_2$-PEG). These compounds may be further substituted with $NH_2$, SH, OH, $CO_2H$, $C_{1-6}$-alkyl that is substituted with $NH_2$, SH, OH or $CO_2H$, or phenyl that is substituted with $NH_2$, SH, OH or $CO_2H$, wherein these functional groups can also serve as the point of covalent attachment to the nanoparticle.

In another embodiment, the low-molecular weight PSMA ligand is

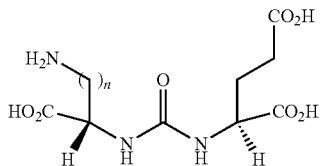

and enantiomers, stereoisomers, rotamers, tautomers, diastereomers, or racemates thereof, wherein n is 1, 2, 3, 4, 5 or 6. For this ligand, the NH$_2$ group serves as the point of covalent attachment to the nanoparticle (e.g., —N(H)-PEG).

In still another embodiment, the low-molecular weight PSMA ligand is

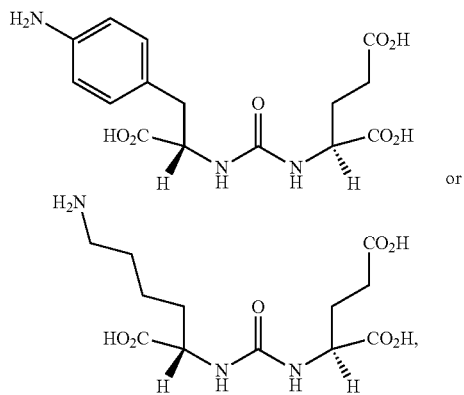

and enantiomers, stereoisomers, rotamers, tautomers, diastereomers, or racemates thereof. Particularly, the butyl-amine compound has the advantage of ease of synthesis, especially because of its lack of a benzene ring. Furthermore, without wishing to be bound by theory, the butyl-amine compound will likely break down into naturally occurring molecules (i.e., lysine and glutamic acid), thereby minimizing toxicity concerns.

For these ligands, the NH$_2$ groups serve as the point of covalent attachment to the nanoparticle (e.g., —N(H)-PEG). Accordingly, the present invention provides the low-molecular weight PSMA ligands shown above, wherein the amine substituents of the compounds are covalently bound to poly(ethylene glycol), e.g., the compounds:

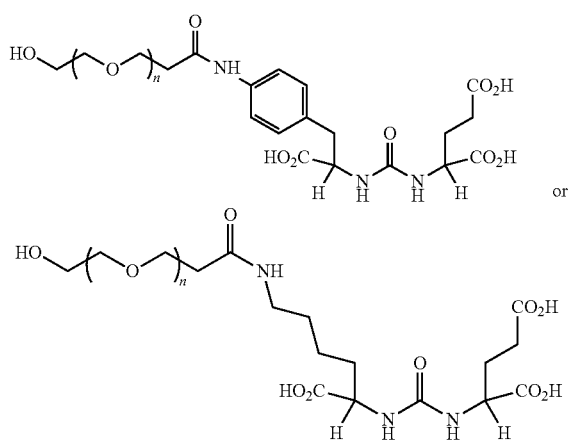

wherein n is 20 to 1720.

Another aspect of the invention provides for a PEG polymer conjugated to a targeting agents and/or bioactive moieties/therapeutic agents as disclosed herein.

Nanoparticle Compositions and Uses Thereof

The nanoparticles produced in accordance with the disclosed methods can be administered alone or in a composition. When nanoparticles are administered as a composition, the composition can be a pharmaceutical (e.g., physiologically acceptable) composition. The composition comprises a carrier (e.g., a pharmaceutically or physiologically acceptable carrier) and the nanoparticles. Any suitable carrier (e.g., water, saline, and PBS) can be used within the context of the invention, and such carriers are well known in the art. The choice of carrier will be determined, in part, by the particular site to which the composition is to be administered and the particular method used to administer the composition. Suitable carriers, as well as other components suitable for use in the composition of the invention, are known in the art (e.g., Remington's Pharmaceutical Sciences, 17th ed., (Mack Publishing Company, Philadelphia, Pa.: 1985)). Additionally, the composition can comprise additional active agents, such as anti-cancer/chemotherapeutic agents.

The nanoparticles and composition thereof can be administered to a subject to treat or prevent particular disorders and diseases. Non-limiting examples of diseases or disorders that can be treated in accordance with the subject invention include cancer, such as lung cancer, breast cancer, prostate cancer, head and neck cancer, ovarian cancer, skin cancer, testicular cancer, pancreatic cancer, esophageal cancer, colorectal cancer, kidney cancer, cervical cancer, gastrointestinal cancer, and combinations thereof. The nanoparticles or the composition thereof preferably are administered to the subject in a therapeutically effective amount.

A therapeutically effective amount refers to an amount of the nanoparticles necessary to treat or prevent the particular disease or disorder. For example nanoparticles disclosed herein can be used to inhibit tumor growth, inhibit or reduce proliferation, invasiveness, or metastasis of tumor or cancer cells, slow the growth of tumors or cancers or reduce the size of tumors.

Any route of administration can be used to deliver the nanoparticles to the subject. Suitable administration routes include intramuscular injection, transdermal administration, inhalation, topical application to tissue (e.g., tumor/cancer tissue), intratumoral administration, and parenteral administration (e.g., intravenous, peritoneal, intraarterial, subcutaneous, rectal, or vaginal, administration). An appropriate administration route easily can be determined by those skilled in the art.

As discussed above, compositions comprising nanoparticles can be useful in the treatment or prevention or amelioration of one or more symptoms of cancer, particularly cancers that express prostate specific membrane antigen (PSMA). These cancers include, but are not limited to, prostate cancer, non-small cell lung cancer, colorectal carcinoma, and glioblastoma, and solid tumors expressing PSMA in the tumor neovasculature.

Various non-limiting embodiments include:
1. A method of preparing a nanoparticle comprising:
   providing a targeting agent;
   providing a functionalized poly(ethylene glycol) (PEG) polymer;
   providing a targeting agent ligand;
   reacting the functionalized poly(ethylene glycol) polymer with the targeting agent to form a targeting agent-PEG polymer complex; and
   mixing the targeting agent-PEG polymer complex with a second polymer and a therapeutic agent to form a nanoparticle, wherein:

the PEG polymer has a molecular weight of between 1,000-20,000 Da (e.g., 5,000-20,000, e.g., 10,000-20,000) and, in some specific embodiments, 5000 Da; and the second polymer has a molecular weight of 5,000-100,000 Da (e.g., 20,000-70,000, e.g., 20,000-50,000), or in some specific embodiments, 15,000-30,000 Da;

2. The method of embodiment 1, wherein the poly(ethylene glycol) is hetero-bifunctional and said targeting agent is covalently bound to the α terminus of said poly(ethylene glycol) and at least one polymerization initiating functional group is present on the ω terminus of said poly(ethylene glycol);

3. The method of embodiment 2, wherein said at least one polymerization initiating functional group is a hydroxyl (—OH) group or an amine (—NH₂) group at the free ω terminus;

4. The method of embodiment 1, 2 or 3, wherein the second polymer comprises a blend of two or more polymers and contains at least one functional group that reacts the functional group present at the free ω terminus of said poly(ethylene glycol) and said at least one functional group of said blend of two or more polymers is a hydroxyl group, a NHS group or an amine group;

5. The method of embodiment 1, wherein the second polymer or the copolymer is a polyester copolymer that contains at least one functional group selected from a hydroxyl group, a NHS group or an amine group and that reacts the functional group present at the free ω terminus of said poly(ethylene glycol);

6. The method of embodiment 4, wherein the second polymer or the copolymer is a polyester copolymer that contains at least one functional group selected from a hydroxyl group, a NHS group or an amine group and that reacts the functional group present at the free ω terminus of said poly(ethylene glycol);

7. The method of embodiment 6, wherein said polyester copolymer comprises a heteropolymer or a homopolymer;

8. The method of embodiment 6, wherein said heteropolymer comprises lactic acid and glycolic acid units or poly (lactic acid-co-glycolic acid) and poly(lactide-co-glycolide) units (PLGA); and said homopolymer comprises glycolic acid units (PGA), lactic acid units (PLA), poly-L-lactic acid units, poly-D-lactic acid units, poly-D,L-lactic acid units, poly-L-lactide units, poly-D-lactide units or poly-D,L-lactide units;

9. The method of embodiment 6, wherein said polyester copolymer is selected from polyhydroxyacids; PEGylated polymers and copolymers of lactide units and glycolide units, PEGylated PLA, PEGylated PGA, PEGylated PLGA, polyanhydrides, poly(ortho ester) PEGylated poly(ortho ester), poly(caprolactone), PEGylated poly(caprolactone), polylysine, PEGylated polylysine, poly(ethylene inline), PEGylated poly(ethylene imine), poly(L-lactide-co-L-lysine), poly (serine ester), poly(4-hydroxy-L-proline ester), poly[a-(4-aminobutyl)-L-glycolic acid] or derivatives thereof;

10. The method of embodiment 1, wherein free carboxylic acid groups or free hydroxyl groups on said targeting agent are protected prior to reacting the functionalized poly(ethylene glycol) polymer with the targeting agent to form a targeting agent-PEG polymer complex;

11. The method of embodiment 4, wherein said functional group of said second polymer is an amine group that reacts with a hydroxyl group or carboxylic acid group on said targeting agent-PEG complex;

12. The method of embodiment 4, wherein said functional group of said second polymer is a hydroxyl group or an NHS group that reacts with an amine group on said targeting agent-PEG complex;

13. The method of embodiment 6, wherein said functional group of said second polymer or said copolymer is an amine group that reacts with a hydroxyl group or carboxylic acid group on said targeting agent-PEG complex;

14. The method of embodiment 6, wherein said functional group of said second polymer or said copolymer is a NHS or hydroxyl group that reacts with an amine group on said targeting agent-PEG complex;

15. The method of embodiments 1-14, wherein said second polymer is a blend of at least two polymers which can be the same or different polymer, wherein the first of said at least two polymers contains at least one hydroxyl group or an NHS group as a functional group and the second of said at least two polymers contains at least one amine group as said functional group;

16. The method of embodiment 1-15, wherein said therapeutic agent is an antibiotic, anti-cancer agent, antiviral agent, anti-inflammatory agent a diagnostic agent, a vaccine antigen or a nutraceutical;

17. The method of embodiment 16, wherein said therapeutic agent is/are penicillins, aminopenicillins, penicillins in conjunction with penicillinase inhibitor and/or anti-fungal agents, cephalosporins, cephamycins, carbapenems, fluoroquinolones, tetracyclines, macrolides, aminoglycosides, erythromycin, bacitracin zinc, polymyxin, polymyxin B sulfates, neomycin, gentamycin, tobramycin, gramicidin, ciprofloxacin, trimethoprim, ofloxacin, levofloxacin, gatifloxacin, moxifloxacin, norfloxacin, sodium sulfacetamide, chloramphenicol, tetracycline, azithromycin, clarithyromycin, trimethoprim sulfate, bacitracin, corticosteroids, medrysone, prednisolone, prednisolone acetate, prednisolone sodium phosphate, fluorometholone, dexamethasone, dexamethasone sodium phosphate, betamethasone, fluoromethasone, antazoline, fluorometholone acetate, rimexolone, loteprednol etabonate, diclofenac (diclofenac sodium), ketorolac, ketorolac tromethamine, hydrocortisone, bromfenac, flurbiprofen, antazoline, xylometazoline, cromolyn sodium, lodoxamide tromethamine, olopatadine HCl, nedocromil sodium, ketotifen fumurate, levocabastine HCL, azelastine HCL, pemirolast (pemirolast potassium), epinastine HCL, naphazoline HCL, emedastine, antazoline, pheniramine, sodium cromoglycate, N-acetyl-aspartyl glutamic acid, amlexanox, 5-fluorouracil (5-FU), CPT-11, 10-hydroxy-7-ethylcamptothecin (SN38), S-I capecitabine, ftorafur, 5' deoxyfluorouridine, UFT, eniluracil, deoxycytidine, 5-azacytosine, 5-azadeoxycytosine, allopurinol, 2-chloroadenosine, aminopterin, methylene-10-deazaminopterin (MDAM), oxaplatin, picoplatin, tetraplatin, satraplatin, platinum-DACH, ormaplatin, [SP-4-3-(R)]-[1,1-cyclobutanedicarboxylato-(2-)](2 methyl-1,4-butanediamine-N,N')platinum (CI-973), and analogs thereof, 9-aminocamptothecin, 10,11-methylenedioxycamptothecin, karenitecin, 9-nitrocamptothecin, 6-[[2-(dimethylamino)ethyl]amino]-3-hydroxy-7H-indeno [2,1-c] quinolin7-one dihydrochloride (TAS 103), L-phenylalanine mustard, ifosphamidemefosphamide, trophosphamide carmustine, epothilones A-E, tomudex, 6-mercaptopurine, 6-thioguanine, karenitecin, acyclovir, valacyclovir, ganciclovir, amantadine, rimantadine, lamivudine, zidovudine, bevacizumab, trastuzumab, rituximab, 20-epi-1α, 25 dihydroxyvitamin D3,4-ipomeanol, 5-ethynyluracil, 9-dihydrotaxol, abiraterone, acivicin, aclarubicin, acodazole hydrochloride, acronine, acylfiilvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisazuidinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caraceraide, carbetimer, carboplatin, carboxamide-amino-triazole, carboxyamidotriazole, methylglyoxal maleimide, carmustine, earn 700, cartilage derived inhibitor, carubicin hydrochloride, carzelesin, casein kinase inhibitors, castanosperrnine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cyclopIatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflornithine, eflornithine hydrochloride, elemene, elsarnitrucin, emitefur, enloplatin, enpromate, epipropidine, epirubicin, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide, lobaplatin, lombricine, lometrexol, lometrexol sodium, lomustine, lonidamine, losoxantrone, losoxantrone hydrochloride, lovastatin, loxoribine, lurtotecan, lutetium texaphyrin lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/mycobacterium cell wall SK, mopidamol, multiple drug resistance gene inhibitor, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazorurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinarnide, RNAi, rogletimide, rohitukine, romurtide, roquinimex, rubiginone Bl, ruboxyl, safingol, safingol hydrochloride, saintopin, sarcnu, sarcophytol A, sargramostim, SDI1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosafe sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride, siRNA or any combinations thereof;

18. The method according of embodiment 1-17, wherein said at least one targeting agent is selected from antibodies, PMSA ligands and polypeptides that bind to epidermal growth factor receptor (EGFR), somatostatin receptor (SSTR), insulin-like growth factor receptor, folic acid-receptor, HER2 receptor, interleukin-13 receptor, gastrin-releasing peptide receptor, CD30, vasoactive intestinal peptide receptor, gastrin receptor, prostate-specific antigen, and/or the estrogen receptor;

19. The method of embodiment 1-18, wherein said method is performed in an aqueous medium;

20. The method of embodiment 1-18, wherein said method is performed in an organic solvent;

21. A nanoparticle produced according to the methods of embodiments 1-20;

22. A composition comprising the nanoparticle of embodiment 21 and a pharmaceutically acceptable carrier;

23. A method of treating a disease comprising the administration of a nanoparticle according of embodiment 21 to a subject in an amount sufficient to treat said disease;

24. The method of embodiment 23, wherein said disease is selected from lung cancer, breast cancer, prostate cancer, head and neck cancer, ovarian cancer, skin cancer, testicular cancer, pancreatic cancer, esophageal cancer, colorectal cancer, kidney cancer, cervical cancer, gastrointestinal cancer, viral infections, bacterial infections or inflammation; and 25. A polymer produced according to the method of embodiments 1-19, said polymer comprising a targeting agent covalently bound to the α terminus of a poly(ethylene glycol) polymer and at least one second polymer covalently bound to said poly(ethylene glycol) polymer via a functional group present on the ω terminus of said poly(ethylene glycol).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

EXAMPLE 1

Synthesis of HO-PEG-lys-urea-glu(Protected) by Covalent Conjugation of lys-urea-glu (Protected) to HO-PEG-CO$_2$H Materials used for the synthesis and purification of HO-PEG-lys-urea-glu(protected) included α-hydroxyethyl-ω-carboxypentyl, poly(ethylene glycol) (Average Molecular Weight=5 Kg/mol, Terminal Activity=98%) (HO-PEG-CO$_2$H, NOF America Corporation, White Plains, N.Y.); Diprop-2-en-1-yl N-{[6-ammonio-1-oxo-1-(prop-2-en-1-yloxy)hexan-2-yl]carbamoyl}glutamate trifluoroacetate (lys-urea-glu(protected), Organix, Woburn, Mass.); N-(3-dimethylaminopropyl)-N'-ethyl carbodiimide (≥97.0%) (EDC, Sigma-Aldrich); N-Ethyl Di-isopropyamine (99.5%) (DIEA, Sigma-Aldrich); N-hydroxysuccinimide (98%) (NHS, Sigma-Aldrich); Chloroform (Anhydrous, ≥99%) Sigma-Aldrich); Ethanol (Absolute, ≥99.5%) (Sigma-Aldrich).

Instrumentation used for the in-process characterization and work-up of HO-PEG-lys-urea-glu(protected) included Bruker 400 MHz Nuclear Magnetic Resonance Spectrometer for Proton NMR Spectroscopic Analysis; Vacuum atmospheres dry nitrogen glove box (<1 ppm water); Edwards RV5 Vacuum Pump and a VWR Oven for Vacuum Drying; Ultrafiltration Diafiltration (UFDF) System based on a peristaltic pump (Masterson), Regenerated Cellulose Membrane filter (Millipore, Surface area=0.1 m$^2$, MWCO 3 kDa), and expanded PTFE tubing (Chem-Sure); Rotary Evaporator (Buchi); Millipore 2 L Vacuum Filtration Assembly and Millipore 0.2 um Fluoropore (PTFE) Membrane Filters; Waters Size Exclusion Chromatography system equipped with Refractive Index Detector and Waters HR1, HR3 and HR4 columns (7.8×300 mm, Molecular Weight Range 100-5000 Da, 500-30,000 Da, 5000-600,000 Da, respectively). Number and Weight Average Molar Mass was determined using Poly (ethylene glycol) calibration standards from Shodex Standards, (Kawasaki, Japan) of Peak Molar Mass (Mp=960, 1400, 4290, 7130, 12900, 20600 Da).

Experimental procedure: All reagents (HO-PEG-CO$_2$H, lys-urea-glu(protected), EDC, NHS, DIEA and anhydrous chloroform) were transferred to a dry nitrogen glove box and subsequently weighed or transferred (using volumetric pipettes or microliter syringes) in 20 mL reaction vials under argon at room temperature. NHS (230 mg, 2 mmol) was added to a solution of HO-PEG-CO$_2$H (1 g, 0.2 mmol) in anhydrous chloroform (5 mL) (solution A). GL2P (1.106 g, 2 mmol) was dissolved in anhydrous chloroform (5 mL), then EDC (354 uL, 2 mmol) and DIEA (685 uL, 4 mmol) were added to this solution (solution B). Solution B was added to solution A and the reaction vial (solution AB) closed under argon. Solution AB was then moved to a vented fume hood and magnetically stirred at room temperature for 2 hours in the dark (reaction vial was wrapped in aluminum foil). Solution AB was diluted with ethanol (100 mL) yielding solvent composition of ethanol/chloroform (10:1) (Solution C). Solution C was diafiltered against 29 dia-volumes (1.5 L) of binary solvent mixture of ethanol/chloroform (9:1 by volume) at a flow rate of 800 mL/min and a 30-40 psi back pressure applied by appropriately adjusting a ¼ turn ball valve. Under these UFDF conditions, the permeate flow rate is approximately 5 mL/min. Solvent was removed from the retentate solution (solution CR) by rotary evaporation at 35° C. and subsequently vacuum dried at room temperature of 18 hours to obtain crude product (770 mg, 70%). Crude product was dissolved in 7.7 mL of chloroform (100 mg/mL, solution D). Solution D was added drop-wise to 150 ml of ether/hexane (70/30) precipitant while stirring. The precipitated product was recovered by filtration using 0.2 micron PTFE membrane filter in a Millipore vacuum filtration apparatus. Purified product, HO-PEG-lys-urea-glu(protected) (white powder, 700 mg, 91%) was obtained by vacuum drying at room temperature for 24 hours to remove residual solvents.

EXAMPLE 2

Characterization of HO-PEG-lys-urea-glu(Protected) to Determine the Mol % End Functionalization with of PEG with lys-urea-glu Targeting Agent and its Molar Mass Identity of HO-PEG-lys-urea-glu(protected) was ascertained by 1H NMR in $D_2O$ using the following instrument parameters: NMR field strength=400 MHz; Number of scans=128; Pulse delay=5 sec; Pulse width=7 μsec. NMR peak assignments are as follows: Allyl $sp^2$ CH (3H multiplet, 5.9-6.03 ppm), allyl $sp^2$ $CH_2$ (6H, two overlapping doublets, 5.27-5.4 ppm), allyl $sp^3$ $CH_2$ (6H, two overlapping doublets, 4.6-4.7 ppm), PEG terminal $CH_2$—OH (2H triplet, 3.85-3.92 ppm), PEG ethylene oxide $CH_2$ (ca. 408H based on $M_n$=5 KDa, singlet 3.7 ppm), PEG terminal $CH_2$ epsilon to CONH-lys-urea-glu (2H triplet, 3.5-3.55 ppm), lysine $CH_2$ epsilon C (2H two triplets, 3.05-3.14 ppm and 3.15-3.22 ppm), PEG terminal $CH_2$ alpha to CONH-lys-urea-glu and PEG terminal $CH_2$ alpha to COOH of uncoupled PEG (2H multiplet, 2.15-2.3 ppm), glutamic acid $CH_2$ gamma C (two 2H overlapping triplets 2.5-2.6 ppm), glutamic acid $CH_2$ beta C (two 1H multiplets, 1.8-2.1 ppm), lysine $CH_2$ beta C (1H multiplet, 1.67-1.8 ppm). The overlapping multiplets between 1.3 and 1.67 ppm were assigned to (a) lysine $CH_2$ beta C (1H), (b) lysine $CH_2$ gamma C (2H), (c) lysine $CH_2$ delta C (2H), (d) PEG terminal $CH_2$'s beta and delta to CONH-lys-urea-glu (2H each), (e) PEG terminal $CH_2$ gamma to CONH-lys-urea-glu (2H). Lys-urea-glu incorporation into HO-PEG-lys-urea-glu(protected) product was estimated using the ratio the ligand multiplet between 1.95-2.1 ppm and PEG multiplet between 2.15-2.3 ppm yielding 82% incorporation of lys-urea-glu(protected) into HO-PEG-lys-urea-glu(protected) conjugate.

Figures 1, 1C:
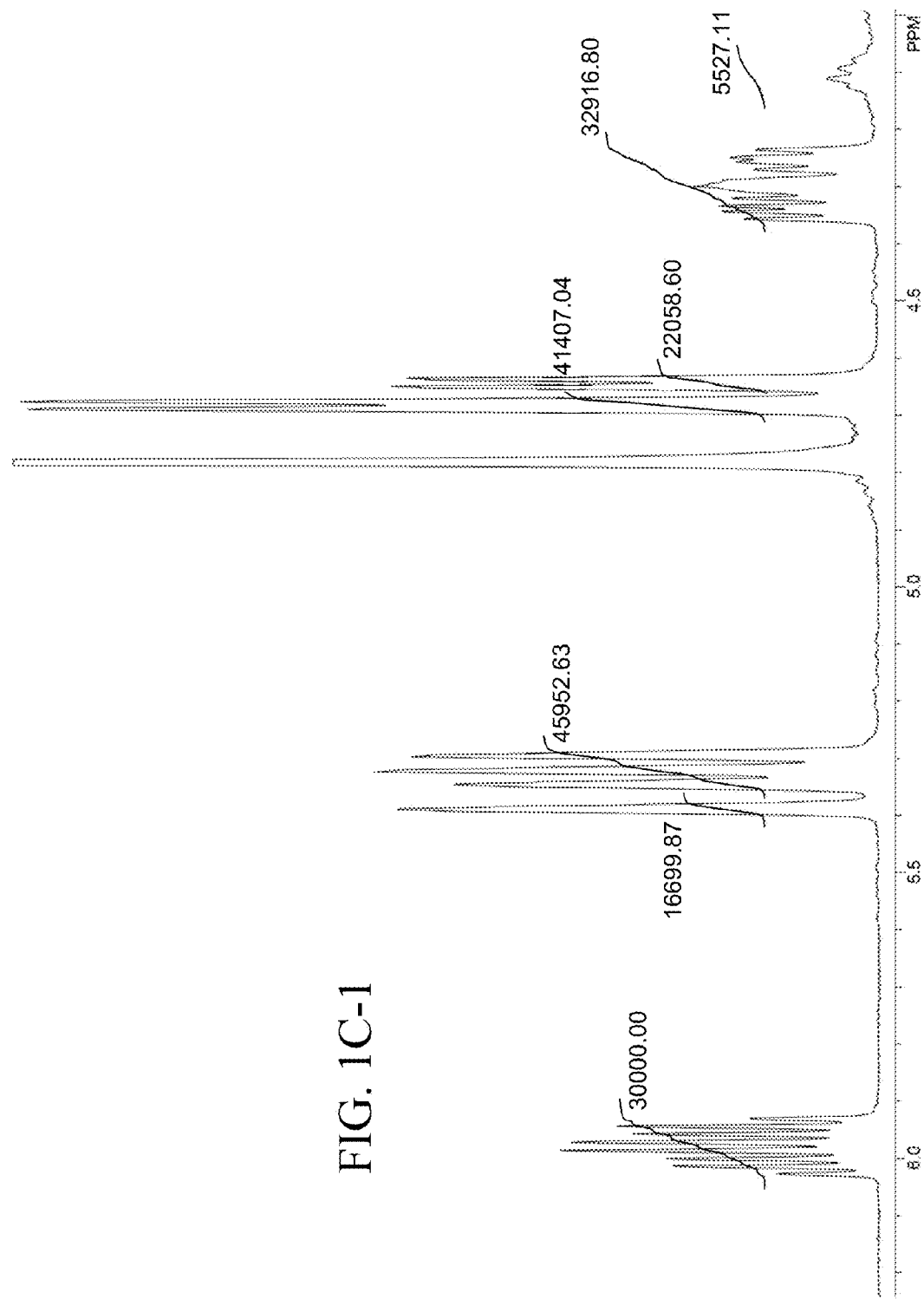

See FIG. 1 for proton NMR spectra of HO-PEG-lys-urea-glu(protected), lot numbers 11-189-1 and 11-176-1.

Molecular weight of HO-PEG-lys-urea-glu(protected) was determined by Size Exclusion Chromatography using Refractive Index detection and chloroform as elution solvent. Column Temperature=30° C., RI Detector temperature=35° C., Sample concentration=10 mg/mL, Injection volume=10 uL. Number and Weight Average Molecular Weight ($M_n$ and $M_w$) were obtained relative to narrow disperse Poly(ethylene glycol) standards from Polymer Standards Service USA (Warwick, R.I.). A fourth order polynomial fit ($R^2$=0.99957; Standard Error=0.02) yielded Mn=5200 Da; Mw=5700 Da; Mw/Mn=1.1 for HO-PEG-lys-urea-glu(protected).

Figure 2A:
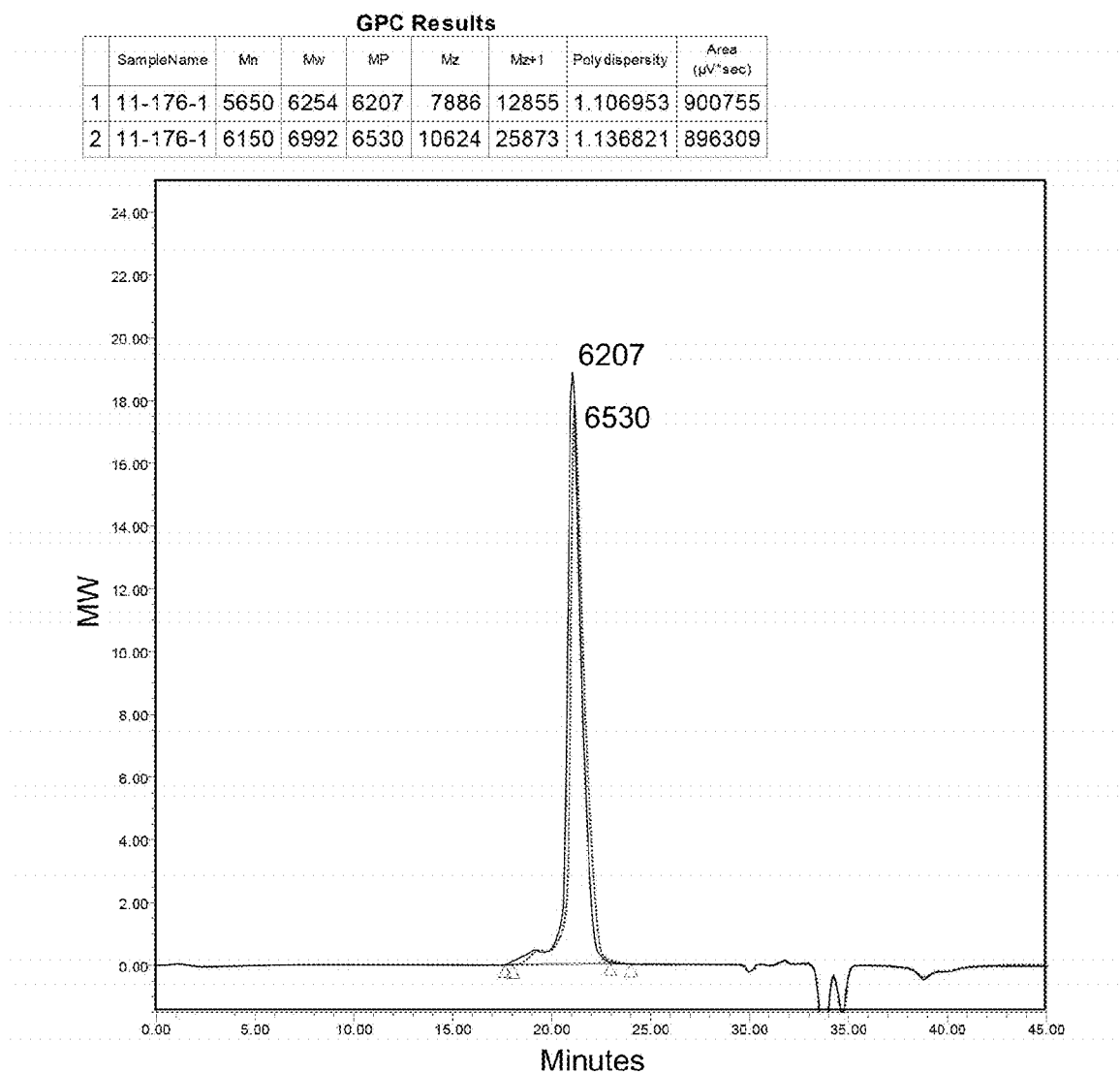
FIGS. 2A-B: Size Exclusion Chromatograms (SEC) of HO-PEG-lys-urea-glu(protected), lot numbers 11-189-1 (FIG. 2B) and 11-176-1 (FIG. 2A).
Figure 2B:
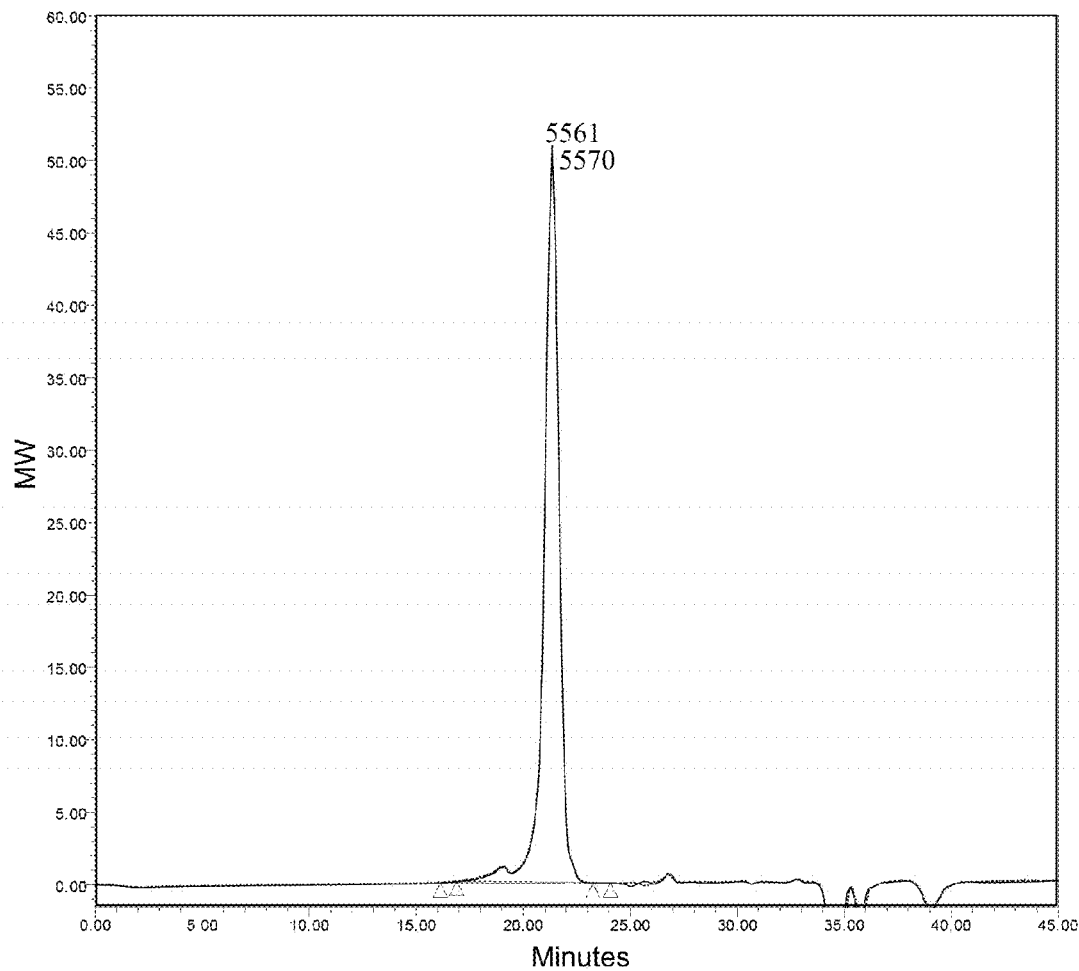
Figure 3A:
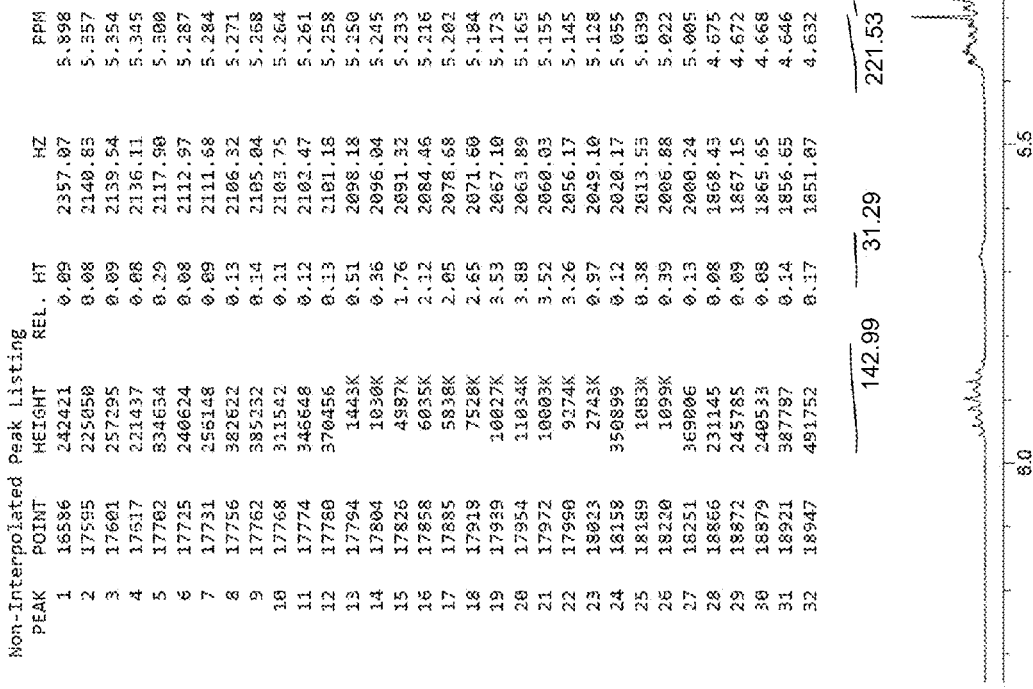
Figure 3B:
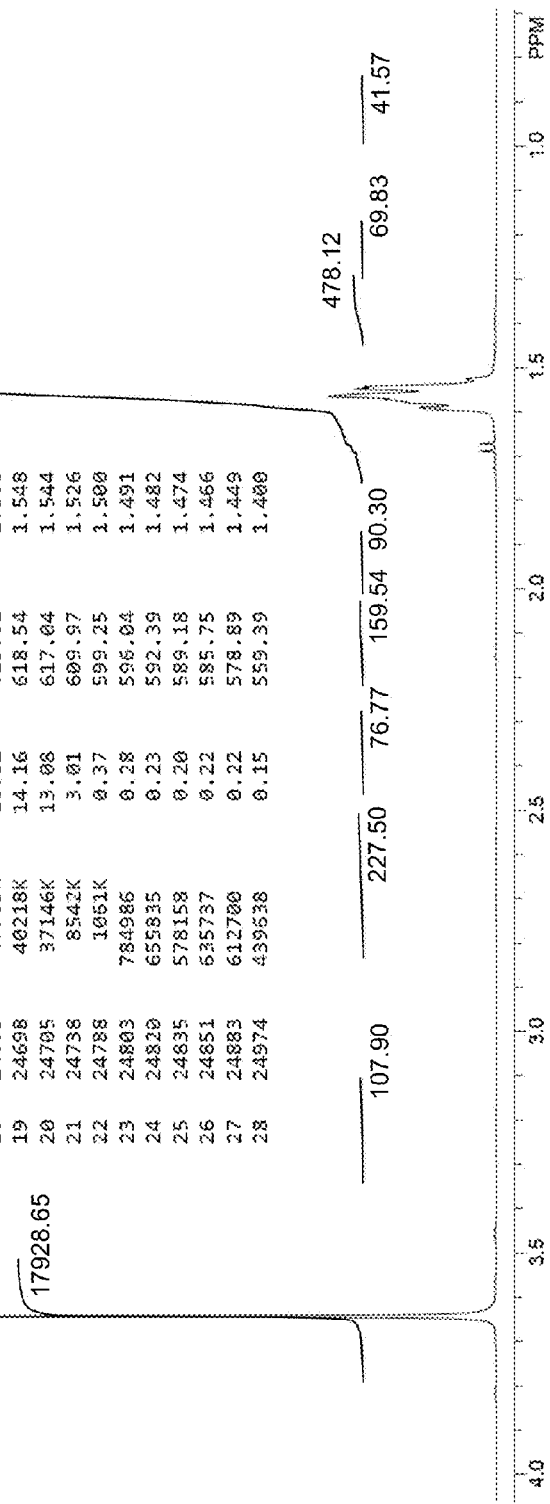
Figure 3D:
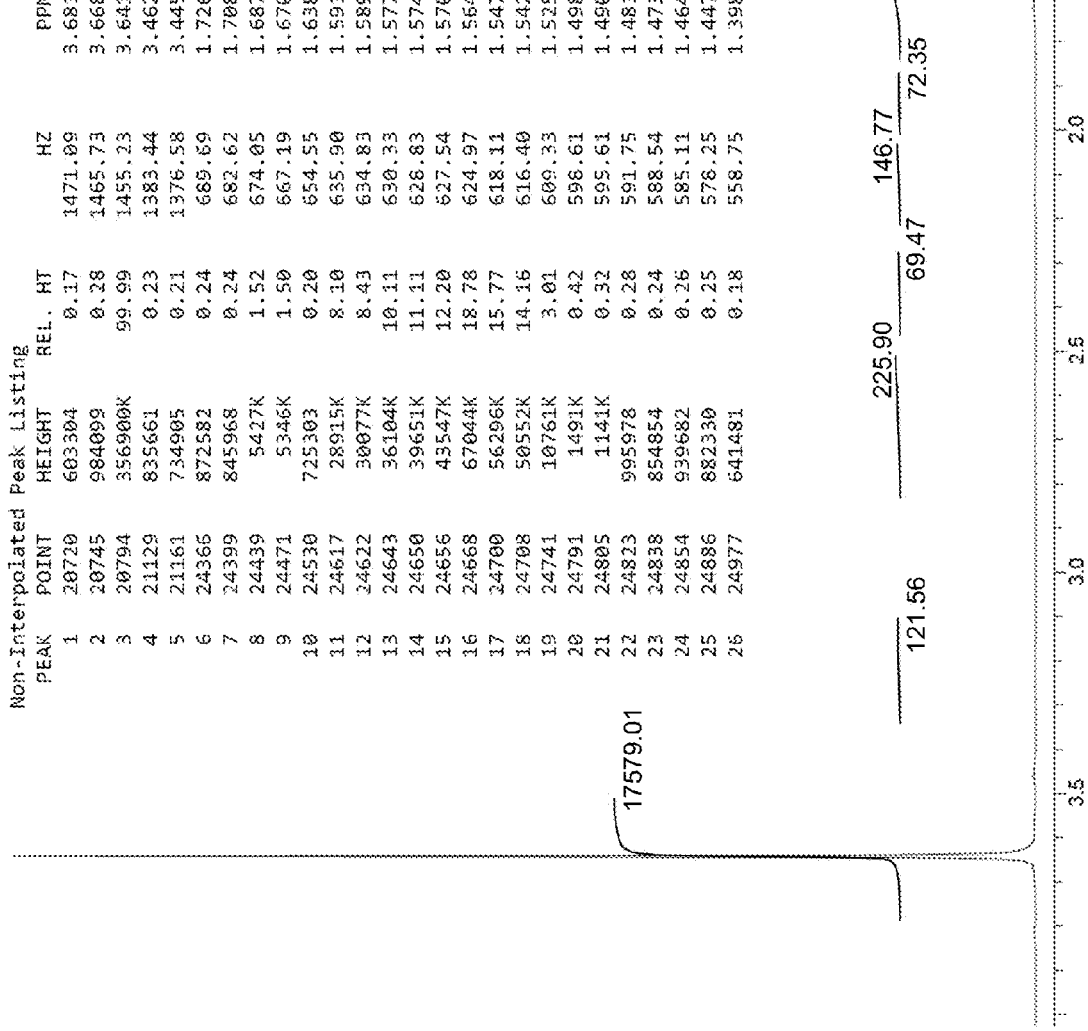
Figure 3F:
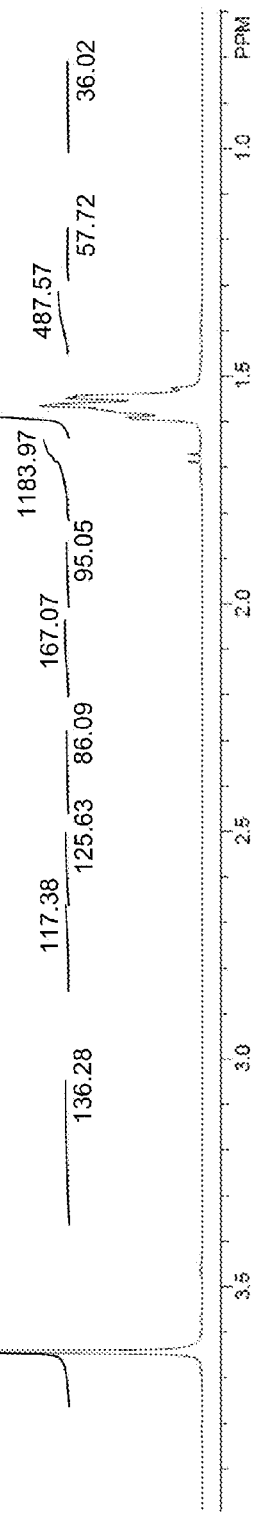

See FIG. 2 for Size Exclusion Chromatograms (SEC) of HO-PEG-lys-urea-glu(protected), lot numbers 11-189-1 (labeled 44-44-6 for SEC analysis) and 11-176-1.

EXAMPLE 3

Synthesis of PLA-PEG-lys-urea-glu(Protected) by Ring Opening Polymerization of D,L-lactide Using HO-PEG-lys-urea-glu (Protected) as Macroinitiator and tin(II) 2-ethylhexanoate as Polymerization Catalyst Materials used in the synthesis of PLA-PEG-lys-urea-glu (protected) included HO-PEG-lys-urea-glu(protected), synthesized as described in Example 1; Tin (II) 2-ethylhexanoate (95%) ($Sn(Oct)_2$, Sigma-Aldrich); D,L-lactide (≥99.5%, Altasorb, Piedmont, S.C.); Hexane, anhydrous (95% DriSolv, EMD) in polymerization reaction and Hexane (Chromasolv., ≥95%, Sigma) for work-up precipitation; Diethyl ether (≥99.0%, Sigma).

Instrumentation used for In-process characterization and reaction/work-up of PLA-PEG-lys-urea-glu(protected) included a Bruker 400 MHz Nuclear Magnetic Resonance Spectrometer for Proton NMR Spectroscopic Analysis at Spectral Data Services, Champaign, Ill.; Vacuum atmospheres dry nitrogen glove box (<1 ppm water); 12-place parallel reaction carousel (Brinkmann-Hiedolph) equipped with a multi-position stir plate and solid state temperature controller (IKA multi-stir plate and temperature controller with feed-back loop; Schlenk reaction tubes equipped with a Teflon stop cock side arm. Edwards RV5 Vacuum Pump and a VWR Oven for Vacuum Drying; Rotary Evaporator (Buchi); Waters Size Exclusion Chromatography system equipped with Refractive Index Detector and Waters HR1, HR3 and HR4 columns (7.8×300 mm, Molecular Weight Range 100-5000 Da, 500-30,000 Da, 5000-600,000 Da, respectively). Number and Weight Average Molar Mass was determined using Poly(styrene) calibration standards from Shodex Standards, (Kawasaki, Japan) of Peak Molar Mass (Mp=1200, 3900, 12800, 31,400, 55,100, and 197,000 Da).

Experimental procedure: All reagents (HO-PEG-lys-urea-glu(protected), $Sn(Oct)_2$, d,l-lactide, anhydrous hexane) were transferred to a dry argon glove box and subsequently manipulated under dry nitrogen at room temperature. HO-PEG-lys-urea-glu (200 mg, $4\times10^{-2}$ mmol) and lactide (800 mg, 5.55 mmol) were weighed into reaction tube (containing a suitably size magnetic stir bar) and septum sealed under dry argon (mixture A). $Sn(Oct)_2$ (250 mg) was weighed into a 6 mL glass vial and dissolved in anhydrous hexane (2.5 mL) to yield a 100 mg/mL solution (B) and septum sealed under dry nitrogen. Mixture A was removed to a vented fume hood and dried under a steady stream of dry argon for 1 hour at room temperature using argon gas manifold equipped with a 8 inch needles as argon gas inlets. Schlenk reaction tube side arms were connected to a silicone oil bubbler to serve as argon gas outlet. The Schlenk tubes were subsequently sealed by stopping the inlet argon flow from the argon gas manifold and the side arm gas outlet through the schlenk tube side arm using the Teflon stop cork. Sealed Schlenk tubes were placed in a 130° C. silicone oil bath and magnetically stirrer to obtain a clear colorless lactide monomer melt (about 10 minutes). Solution B (80 uL) was introduced via a 500 uL syringe via the septum seal. The reaction mixture (C) was allowed to stir at 130° C. for 16 hours. Reaction mixture C was cooled to room temperature, Schlenk tube opened in air and polymer pellet dissolved in 5 mL dichloromethane by vortexing for 1 hour at room temperature (solution D). Solution D was transferred to a 20 mL glass vial and Schlenk tube rinsed with 2×2.5 mL portion of fresh dichloromethane. The washing were combined with solution D. This slightly turbid solution was filtered using 0.45 micron PTFE syringe filters to obtain a clear colorless solution (Solution E). Solution E was added drop-wise to diethyl ether/hexane (70/30) (200 mL) while stirring at room temperature. The cloudy precipitate was allowed to stir at room temperature for 2 hours to allow polymer to coagulate and settle to the bottom of the beaker. The clear supernatant was decanted and the tacky polymer product (700 mg, 70%) was transferred to glass vial using spatula and subsequently dried under vacuum at room temperature for 18 hours.

EXAMPLE 4

Characterization of PLA-PEG-lys-urea-glu(Protected) to Determine the Mol % End Functionalization with of PEG with lys-urea-glu Targeting Agent and its Molar Mass Identity of PLA-PEG-lys-urea-glu(protected) was ascertained by 1H NMR in chloroform-d using the following instrument parameters: NMR field strength=400 MHz; Number of scans=128; Pulse delay=5 sec; Pulse width=7 μsec. NMR peak assignments are as follows: Lactide methine CH (1H multiplet, 5.1-5.3 ppm), Lactide methyl $CH_3$ (3H multiplet, 1.45-1.65), PEG ethylene oxide $CH_2$ (ca. 408H based on $M_n$=5 KDa, singlet 3.55-3.8), allyl $sp^2$ CH (3H multiplet, 5.8-6.0 ppm). The number average molar mass (Mn) of PLA-PEG-lys-urea-glu(protected) was determined by proton NMR spectroscopy using PEG to poly(d,l-lactide) ratio. Comparison of the intensities of the allyl $sp^2$ CH (3H multiplet, 5.8-6.0 ppm) peak and the lactide methine CH (1H multiplet, 5.1-5.3 ppm) peak yielded $M_n$ (PLA-PEG-lys-urea-glu(protected)=20,100 Da assuming PEG $M_n$=5 Kg/mol.

See FIG. 3 for proton NMR spectra of PLA-PEG-lys-urea-glu(protected), lot numbers 11-187-1, 11-188-1 and 11-198-1.

Molecular weight of PLA-PEG-lys-urea-glu(protected) was also determined by Size Exclusion Chromatography using Refractive Index detection and chloroform as elution solvent. Column Temperature=30° C., RI Detector temperature=35° C., Sample concentration=10 mg/mL, Injection volume=10 uL. $M_n$ and $M_w$ were obtained relative to narrow disperse Polystyrene Standards (Shodex Standards, Kawasaki, Japan). A fourth order polynomial fit ($R^2$=0.999977; Standard Error=0.009) yielded $M_n$=20700 Da; $M_w$=25400 Da; Mw/Mn=1.23 for PLA-PEG-PLA-PEG-lys-urea-glu(protected).

Figure 4:
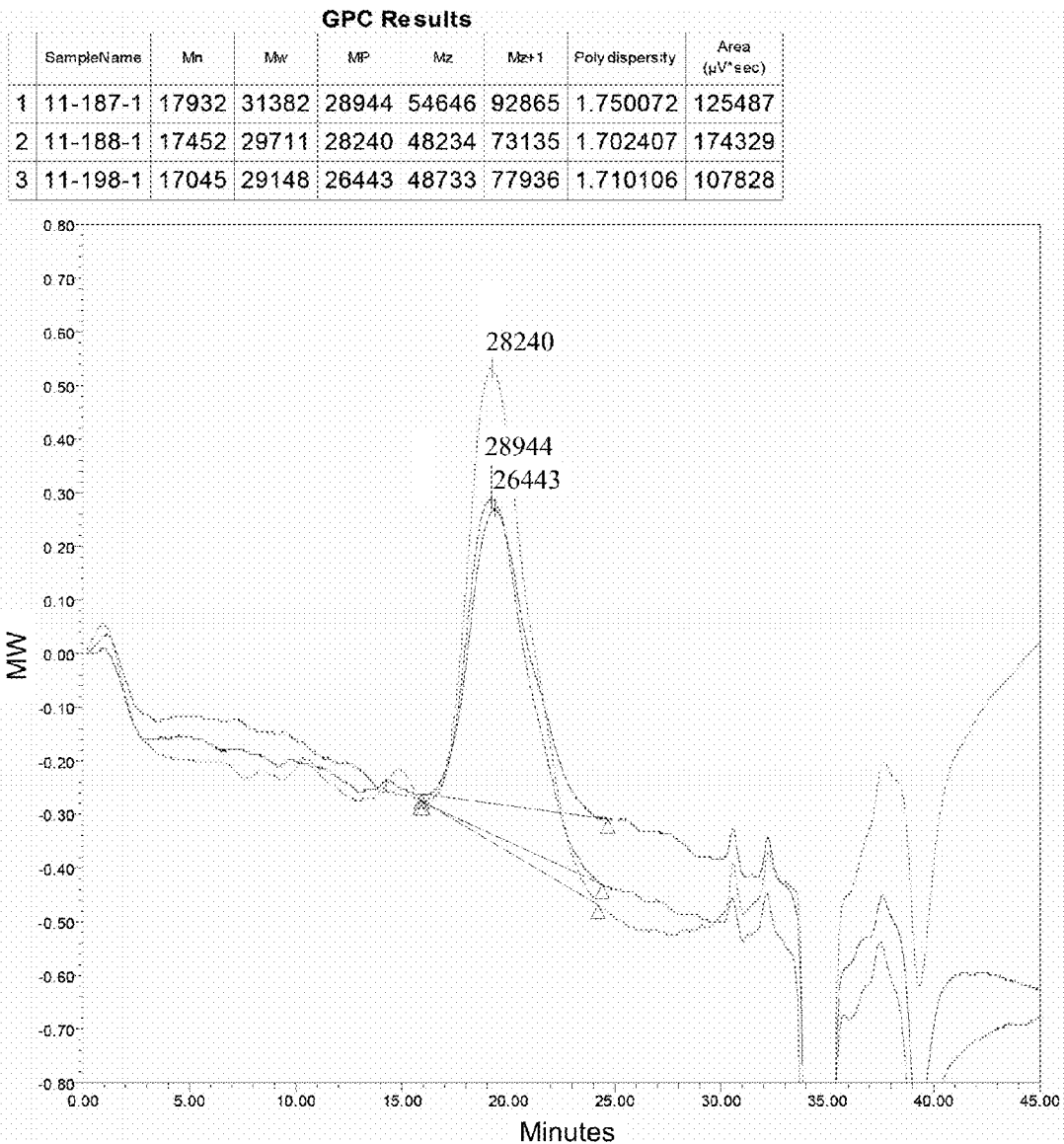
FIG. 4: Size Exclusion Chromatograms (SEC) of HO-PEG-lys-urea-glu(protected), lot numbers 11-189-1 (labeled 44-44-6 for SEC analysis) and 11-176-1.
Size Exclusion Chromatographic Conditions:
Detector: Refractive Index detection (RI); RI Detector temperature=35° C.
Columns: Water Styragel (HR1, 100-5000 Da; HR3, 500-30000 Da; HR4, 5000-600,000 Da in series). Column Temperature=30° C.; Mobile phase: Chloroform; Flow rate: 1 mL/min
Sample concentration=10 mg/mL, Injection volume=20 uL; Number and Weight Average Molecular Weight ($M_n$ and $M_w$) and polydispersity ($M_w/M_n$) were obtained relative to narrow disperse Poly(styrene) Standards (Shodex Standards, Kawasaki, Japan). A fourth order polynomial fit ($R^2$=0.999927; Standard Error=0.008) was used for calibration.
Figure 5A:
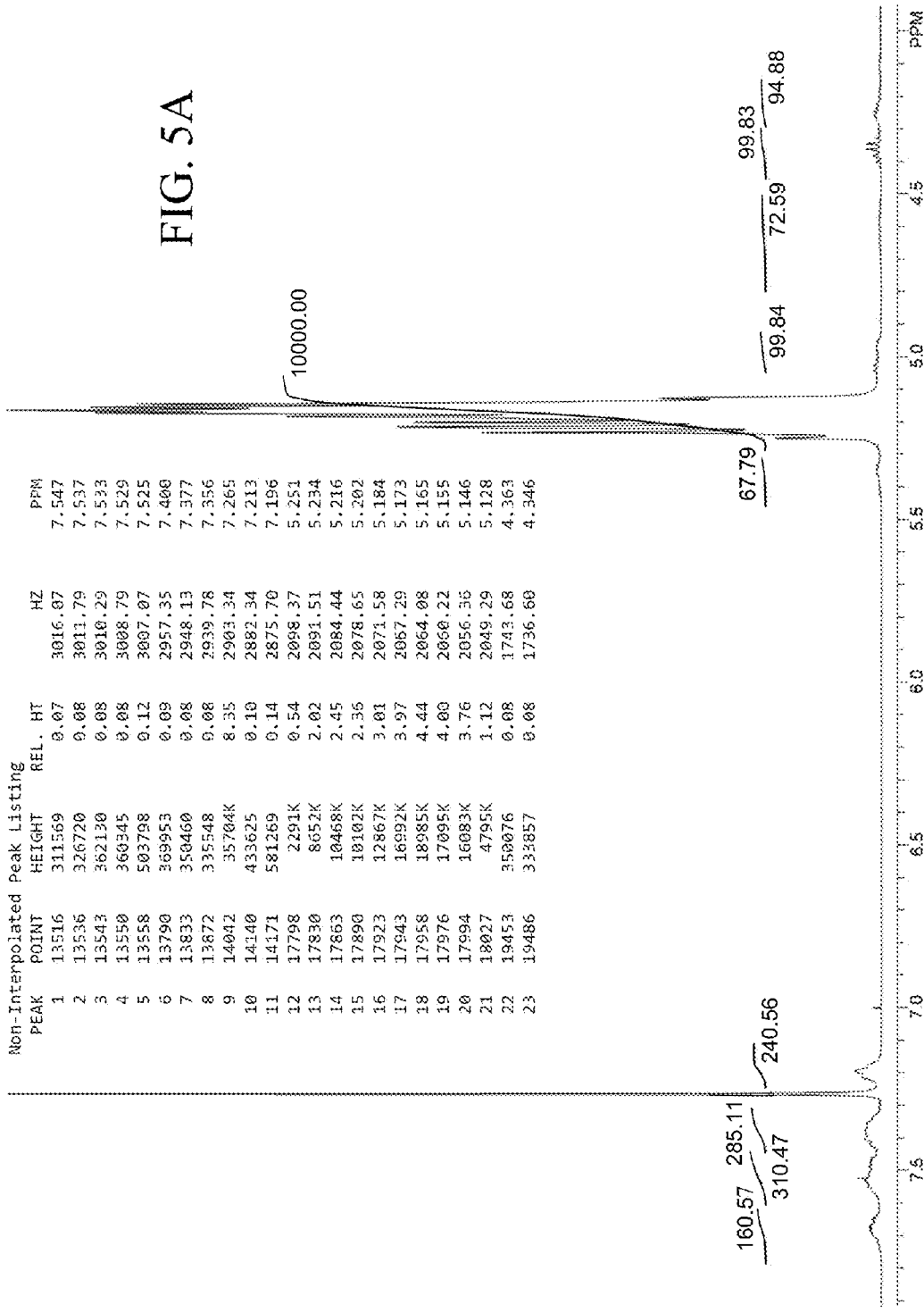
FIGS. 5A-E: Efficiency of deprotection and estimate of Molar mass of crude PLA-PEG-lys-urea-glu (prior to palladium removal) by 1H NMR Spectroscopy.
NMR Instrument: Bruker 400 MHz
NMR Experiment Parameters:
Solvent: $CDCl_3$; Pulse Width: 7.5 usec; Pulse Delay: 5 sec; Number of scans: 128
FIG. 5A—Crude PLA-PEG-lys-urea-glu Lot#11-190-1; 1H NMR Spectrum Expansion #1 showing: a) lactide methine peak, b) peaks of aromatic protons of tetrakis(triphenyl-phosphine)palladium (0), and c) absence of residual allyl peaks (δ 5.85-5.95) indicating quantitative removal of protecting groups.
Figure 5B:
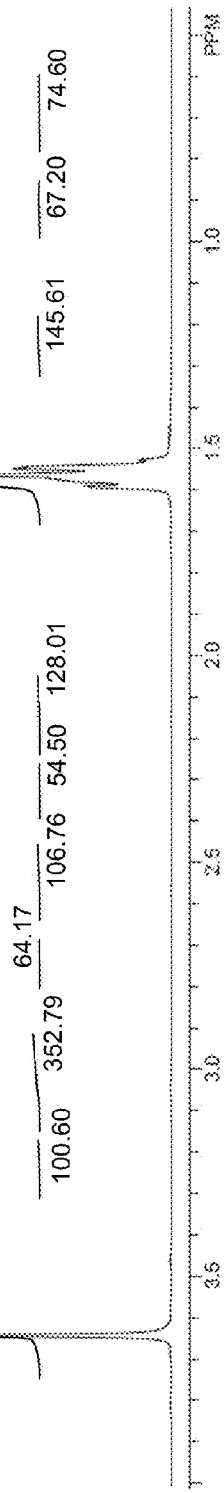
Figure 5C:
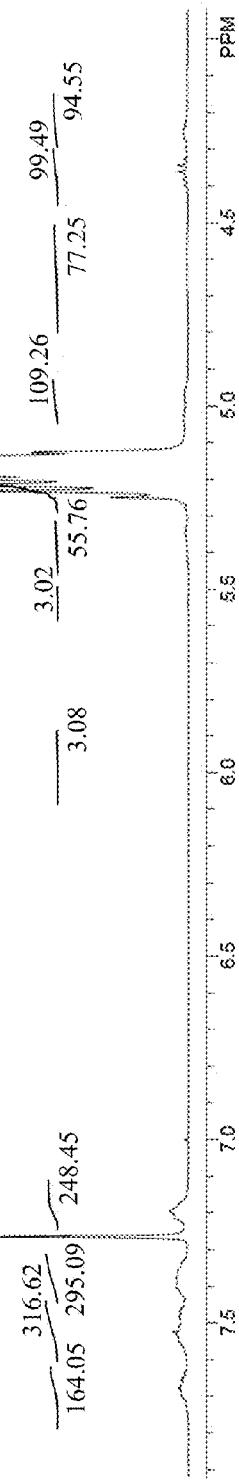
Figure 5D:
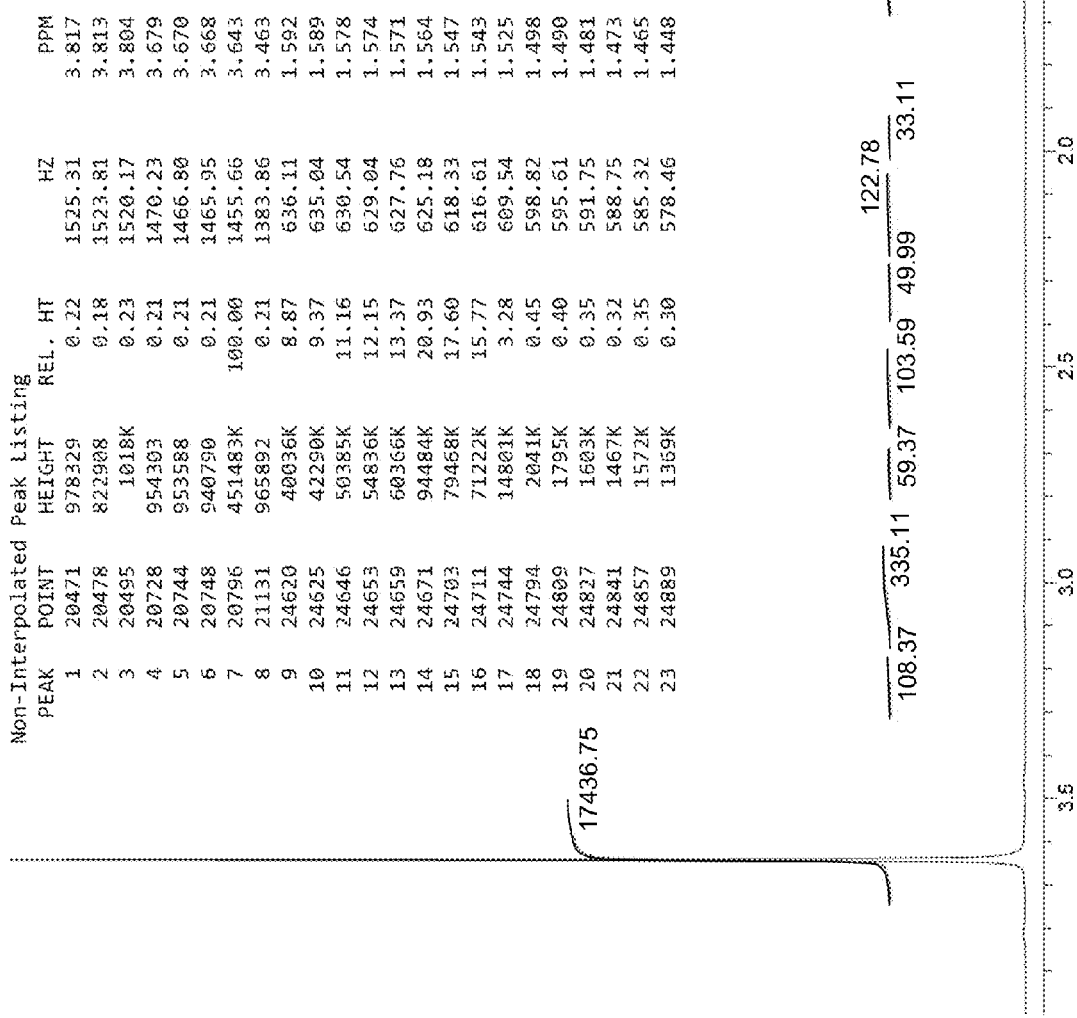
Figure 5E:
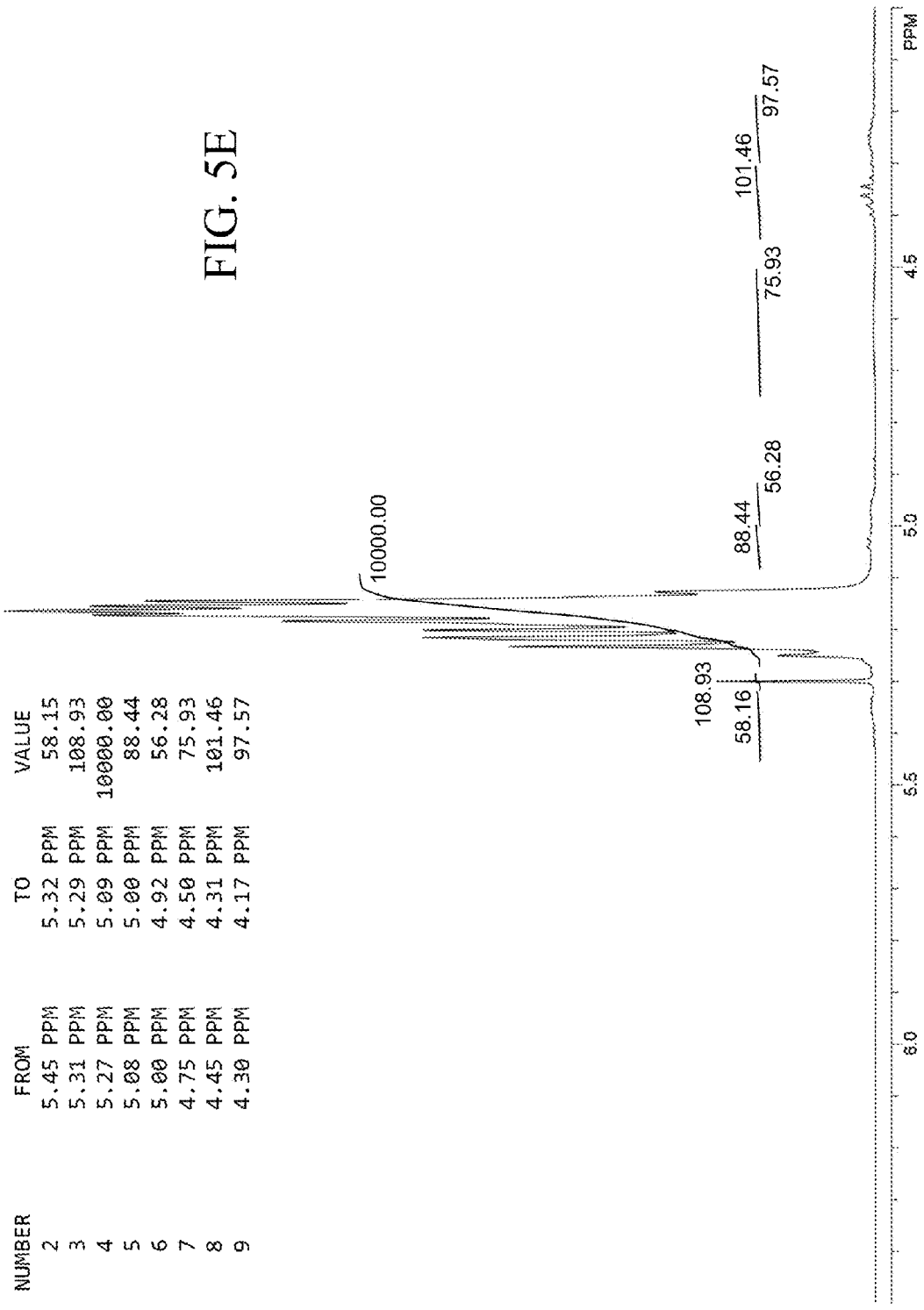
Figure 5F:
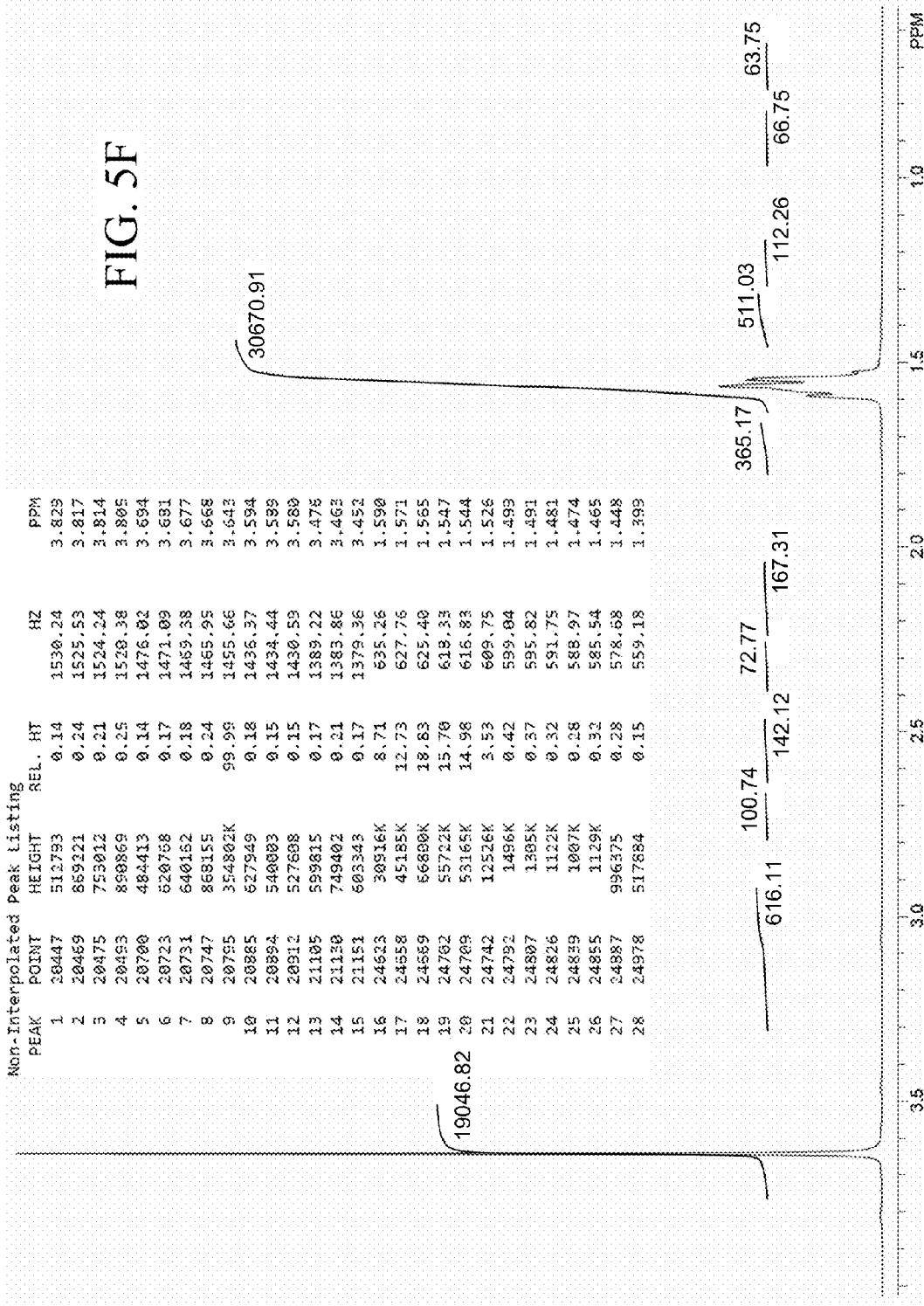
FIG. 5F—Crude PLA-PEG-lys-urea-glu Lot#11-199-1; 1H NMR Spectrum Expansion #2 showing PEG and lactide methyl peaks.

See FIG. 4 for Size Exclusion Chromatograms (SEC) of HO-PEG-lys-urea-glu(protected), lot numbers 11-189-1 (labeled 44-44-6 for SEC analysis) and 11-176-1.

EXAMPLE 5

Synthesis of PLA-PEG-lys-urea-glu by Removal of the allyl Protecting Groups of PLA-PEG-lys-urea-glu(Protected) Using tetrakis(triphenylphosphine) palladium (0)

Materials used for the synthesis of PLA-PEG-lys-urea-glu included PLA-PEG-lys-urea-glu(protected), synthesized as described in Example 3;

Tetrakis(triphenylphosphene)palladium(0)(99%) (Pd-tetrakis, Sigma); Morpholine (99.5%, Sigma); Dichloromethane (Anhydrous, ≥99.8%, Sigma); Diethyl ether (≥99.0%, Sigma); Hexane (Chromasolv., ≥95%, Sigma).

Instrumentation and equipment used for work-up procedures and in-process characterization included a Bruker 400 MHz Nuclear Magnetic Resonance Spectrometer for Proton NMR Spectroscopic Analysis; Edwards RV5 Vacuum Pump and a VWR Oven for Vacuum Drying; Rotary Evaporator (Buchi).

Experimental procedure: PLA-PEG-lys-urea-glu(protected) (1000 mg, $4.76 \times 10^{-2}$ mmol) was dissolved in anhydrous dichloromethane (4 mL) under ambient air (Solution A). Pd-tetrakis (55 mg, $4.76 \times 10^{-2}$ mmol) was dissolved in anhydrous dichloromethane (4 mL) also under ambient air (Solution B). Morpholine (41.5 mg or 45.2 uL, 0.476 mmol) was added to solution A, this was immediately followed by the addition of Solution B to Solution A. Dichloromethane (2 mL) was used to rinse the Solution B vial and this rinse solution was combined with Solution A to ensure quantitative transfer of the Pd-tetrakis to the reaction mixture (C). Mixture C was allowed to stir closed and in the dark (reaction vial was wrapped in aluminum foil) at room temperature for 2 hours. Reaction mixture C was opened in air and added dropwise into diethyl ether/hexane (70/30, (v/v)) (200 mL) at room temp while stirring. The resulting polymer suspension was allowed to stir at room temperature for 2 hours allowing it to coagulate and settle to the bottom of the beaker. The clear supernatant was decanted off and the tacky polymer was transferred using spatula to a glass vial. PLA-PEG-lys-urea-glu (800 mg, 80%) product was dried under vacuum for 18 hours at room temperature.

EXAMPLE 6

Palladium Removal from PLA-PEG-lys-urea-glu Using trimercapto triazide Functional Palladium Scavenging Resin PLA-PEG-lys-urea-glu (1050 mg) was dissolved in dichloromethane (30 mL) to yield a 35 mg/mL solution. Palladium scavenging resin (TMT, 5 g in 60 mL column) was solvated with dichloromethane (10 mL) and PLA-PEG-lys-urea-glu solution (30 mL) added. Eluant was collected under gravity and column rinsed with additional dichloromethane (40 mL). Main and rinse eluant fractions combined and solvent removed by rotary evaporation to recover polymer. Polymer was subsequently dissolved in dichloromethane (10.5 mL, 100 mg/mL solution) and added dropwise to 70/30 ether/hexane (210 mL). The resulting polymer suspension was allowed to stir at room temperature for 2 hours allowing it to coagulate and settle to the bottom of the beaker. The clear supernatant was decanted off and the tacky PLA-PEG-lys-urea-glu polymer was transferred using spatula to a glass vial (940 mg, 90%).

EXAMPLE 7

Characterization of PLA-PEG-lys-urea-glu to Determine the Efficiency of Deprotection, Molar Mass and Residual Palladium Content The identity of PLA-PEG-lys-urea-glu was ascertained by 1H NMR in chloroform-d using the following instrument parameters: NMR field strength=400 MHz; Number of scans=128; Pulse delay=5 sec; Pulse width=7 μsec. NMR peak assignments are as follows: Lactide methine CH (1H multiplet, 5.1-5.3 ppm), Lactide methyl $CH_3$ (3H multiplet, 1.45-1.7), PEG ethylene oxide $CH_2$ (ca. 408H based on $M_n$=5 KDa, singlet 3.55-3.8), residual allyl $sp^2$ CH (3H multiplet, 5.8-6.0 ppm).

The efficiency of deprotection reaction was also determined by NMR as 95% (allyl removal). This was calculated using the ratio of the intensity of the residual allyl peak in the product PLA-PEG-lys-urea-glu spectrum to that of the corresponding peak in the starting material (PLA-PEG-lys-urea-glu(protected)) spectrum.

The number average molar mass ($M_n$) of PLA-PEG-lys-urea-glu was estimated by NMR using PEG to poly(d,l-lactide) ratio. Comparison of the intensities of the PEG ethylene oxide $CH_2$ (408H, singlet 3.55-3.8) peak and the lactide methine CH (1H multiplet, 5.1-5.3 ppm) peak yielded $M_n$ (PLA-PEG-lys-urea-glu)=21,400 Da assuming PEG $M_n$=5 Kg/mol.

Palladium content in product PLA-PEG-lys-urea-glu was determined by ICP Spectrometry and found <5 ppm.

The molar mass of PLA-PEG-lys-urea-glu was estimated by measurement of inherent viscometry (IV) in dimethylsulfoxide and chloroform (0.309 dL/g and 0.198 dL/g, respectively). The I.V. of the protected precursor PLA-PEG-lys-urea-glu(protected) was determined in dimethylsulfoxide (0.217 dL/g). A minor drop in viscosity from 0.217 dL to 0.198 dL/g was observed and may be attributed to differences in polymer solvent interactions as a result of the more polar nature of lys-urea-glu relative to the allyl protected precursor.

See FIG. 5 for proton NMR spectra of crude (prior to palladium removal) PLA-PEG-lys-urea-glu, lot numbers 11-187-1, 11-188-1 and 11-198-1.

Figure 6A:
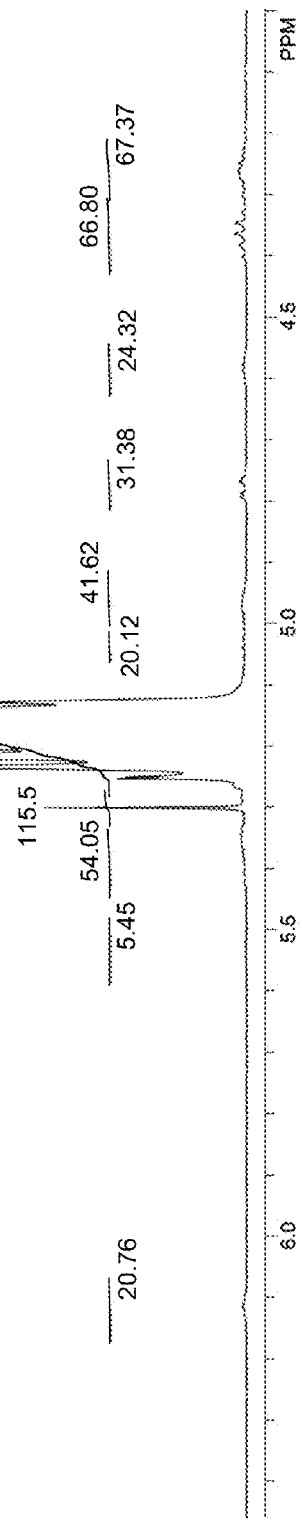
FIGS. 6A-B: Molar Mass and PEG fraction of purified PLA-PEG-lys-urea-glu by 1H NMR Spectroscopy.
NMR Instrument: Bruker 400 MHz
NMR Experiment Parameters:
Solvent: $CDCl_3$; Pulse Width: 7.5 usec; Pulse Delay: 5 sec; Number of scans: 128
FIG. 6A—PLA-PEG-lys-urea-glu Lot#44-49-1; 1H NMR Spectrum Expansion #1 showing: a) lactide methine peak, b) absence of residual allyl peaks (δ 5.85-5.95) indicating quantitative removal of protecting groups.
Figure 6B:
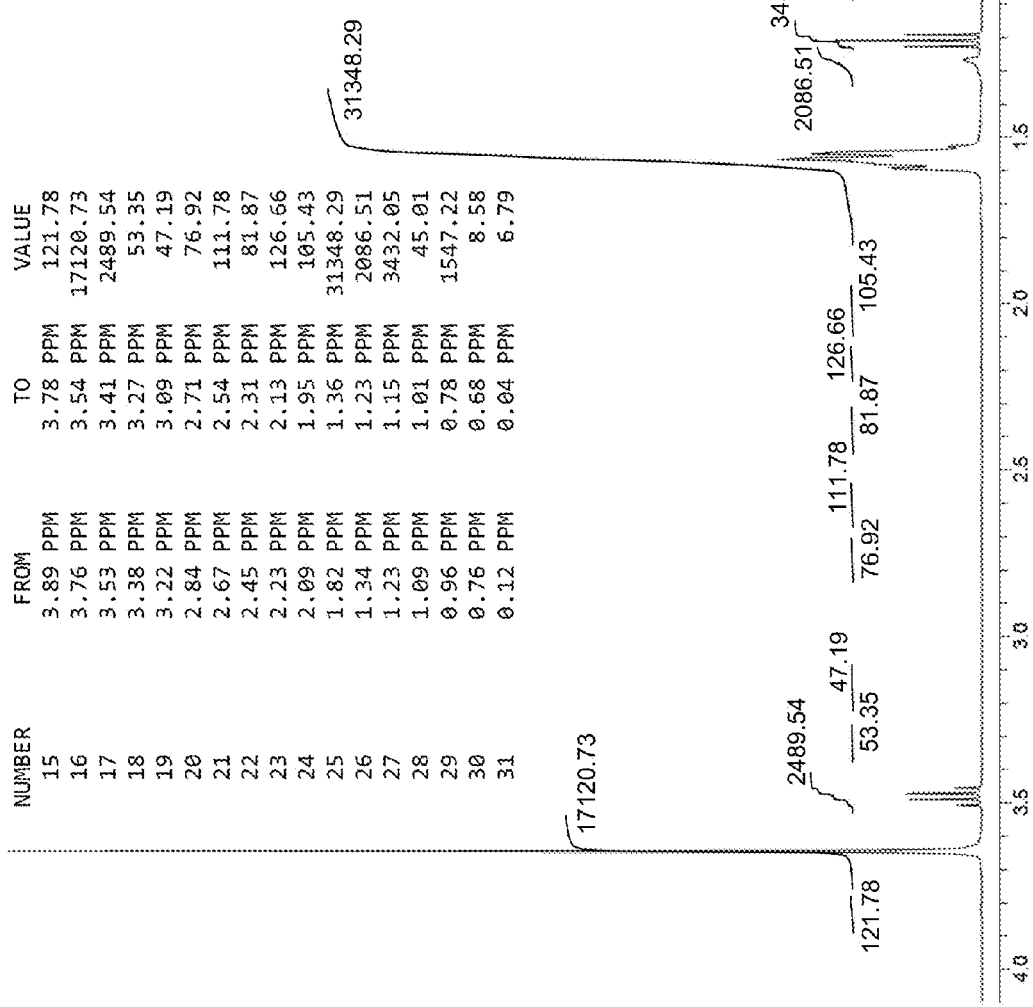

See FIG. 6 for proton NMR spectra of purified (after palladium removal) PLA-PEG-lys-urea-glu, lot number 44-49-1.

See FIG. 7 for Inherent viscosity of purified (after palladium removal) PLA-PEG-lys-urea-glu, lot number 44-49-1 and the protected precursor PLA-PEG-lys-urea-glu(protected).

See FIG. 8 for Palladium Content in crude (prior to palladium removal) PLA-PEG-lys-urea-glu lot number 44-48-1 (sample code 11-204-1) and purified (after palladium removal) PLA-PEG-lys-urea-glu lot number 44-49-1 (sample code 11-204-2) determined by ICP Spectrometry.

We claim:

1. A method of preparing a nanoparticle comprising:
   providing a targeting agent, said targeting agent having an unprotected functional group,
   protecting the unprotected functional group on said targeting agent,
   providing a functionalized poly(ethylene glycol) (PEG) polymer;
   reacting the functionalized poly(ethylene glycol) polymer with the protected targeting agent to form a targeting agent-PEG polymer complex;
   reacting the targeting agent-PEG polymer complex with a second polymer to form a targeting agent-PEG polymer-second polymer complex; and
   mixing the targeting agent-PEG polymer-second polymer complex with a third polymer and a therapeutic agent to form a nanoparticle.

2. The method of claim 1, wherein the poly(ethylene glycol) is hetero-bifunctional and said targeting agent is covalently bound to the α terminus of said poly(ethylene glycol) and at least one polymerization initiating functional group is present on the ω terminus of said poly(ethylene glycol).

3. The method of claim 2, wherein said at least one polymerization initiating functional group is a hydroxyl (—OH) group or an amine (—$NH_2$) group at the free ω terminus that reacts with a second copolymer.

4. The method of claim 3, wherein the second polymer comprises a blend of two or more polymers and contains at least one functional group that reacts the functional group present at the free ω terminus of said poly(ethylene glycol) and said at least one functional group of said blend of two or more polymers is a hydroxyl group, a NHS group or an amine group.

5. The method of claim 1, wherein the second polymer or the copolymer is a polyester copolymer that contains at least one functional group selected from a hydroxyl group, a NHS group or an amine group and that reacts the functional group present at the free ω terminus of said poly(ethylene glycol).

6. The method of claim 4, wherein the second polymer or the copolymer is a polyester copolymer that contains at least one functional group selected from a hydroxyl group, a NHS group or an amine group and that reacts the functional group present at the free ω terminus of said poly(ethylene glycol).

7. The method of claim 6, wherein said polyester copolymer comprises a heteropolymer or a homopolymer.

8. The method of claim 7, wherein said heteropolymer comprises lactic acid and glycolic acid units or poly(lactic acid-co-glycolic acid) and poly(lactide-co-glycolide) units (PLGA); and said homopolymer comprises glycolic acid units (PGA), lactic acid units (PLA), poly-L-lactic acid units, poly-D-lactic acid units, poly-D,L-lactic acid units, poly-L-lactide units, poly-D-lactide units or poly-D,L-lactide units.

9. The method of claim 6, wherein said polyester copolymer is selected from polyhydroxyacids; PEGylated polymers and copolymers of lactide units and glycolide units, PEGylated PLA, PEGylated PGA, PEGylated PLGA, polyanhydrides, poly(ortho ester) PEGylated poly(ortho ester), poly (caprolactone), PEGylated poly(caprolactone), polylysine, PEGylated polylysine, poly(ethylene inline), PEGylated poly (ethylene imine), poly(L-lactide-co-L-lysine), poly(serine ester), poly(4-hydroxy-L-proline ester), poly[a-(4-aminobutyl)-L-glycolic acid] or derivatives thereof.

10. The method of claim 1, wherein the unprotected functional group on the targeting agent is a free carboxylic acid group or a free hydroxyl group and the free carboxylic acid group or the free hydroxyl group is protected prior to reacting the functionalized poly(ethylene glycol) polymer with the targeting agent to form a targeting agent-PEG polymer complex.

11. The method of claim 4, wherein said functional group of said second polymer is an amine group that reacts with a hydroxyl group or carboxylic acid group on said targeting agent-PEG complex.

12. The method of claim 4, wherein said functional group of said second polymer is a hydroxyl group or an NHS group that reacts with an amine group on said targeting agent-PEG complex.

13. The method of claim 6, wherein said functional group of said second polymer or said copolymer is an amine group that reacts with a hydroxyl group or carboxylic acid group on said targeting agent-PEG complex.

14. The method of claim 6, wherein said functional group of said second polymer or said copolymer is a NHS or hydroxyl group that reacts with an amine group on said targeting agent-PEG complex.

15. The method of claim 1, wherein said second polymer is a blend of at least two polymers which can be the same or different polymer, wherein the first of said at least two polymers contains at least one hydroxyl group or an NHS group as a functional group and the second of said at least two polymers contains at least one amine group as said functional group.

16. The method of claim 1, wherein said therapeutic agent is an antibiotic, anti-cancer agent, antiviral agent, anti-inflammatory agent a diagnostic agent, a vaccine antigen or a nutraceutical.

17. The method of claim 16, wherein said therapeutic agent is/are penicillins, aminopenicillins, penicillins in conjunction with penicillinase inhibitor and/or anti-fungal agents, cephalosporins, cephamycins, carbapenems, fluoroquinolones, tetracyclines, macrolides, aminoglycosides, erythromycin, bacitracin zinc, polymyxin, polymyxin B sulfates, neomycin, gentamycin, tobramycin, gramicidin, ciprofloxacin, trimethoprim, ofloxacin, levofloxacin, gatifloxacin, moxifloxacin, norfloxacin, sodium sulfacetamide, chloramphenicol, tetracycline, azithromycin, clarithyromycin, trimethoprim sulfate, bacitracin, corticosteroids, medrysone, prednisolone, prednisolone acetate, prednisolone sodium phosphate, fluormetholone, dexamethasone, dexamethasone sodium phosphate, betamethasone, fluoromethasone, antazoline, fluorometholone acetate, rimexolone, loteprednol etabonate, diclofenac (diclofenac sodium), ketorolac, ketorolac tromethamine, hydrocortisone, bromfenac, flurbiprofen, antazoline, xylometazoline, cromolyn sodium, lodoxamide tromethamine, olopatadine HCl, nedocromil sodium, ketotifen fumarate, levocabastine HCL, azelastine HCL, pemirolast (pemirolast potassium), epinastine HCL, naphazoline HCL, emedastine, antazoline, pheniramine, sodium cromoglycate, N-acetyl-aspartyl glutamic acid, amlexanox, 5-fluorouracil (5-FU), CPT-11, 10-hydroxy-7-ethylcamptothecin (SN38), S-I capecitabine, ftorafur, 5'deoxyflurouridine, UFT, eniluracil, deoxycytidine, 5-azacytosine, 5-azadeoxycytosine, allopurinol, 2-chloroadenosine, aminopterin, methylene-10-deazaaminopterin (MDAM), oxaplatin, picoplatin, tetraplatin, satraplatin, platinum-DACH, ormaplatin, [SP-4-3-(R)]-[1,1-cyclobutanedicarboxylato-(2)](2 methyl-1,4-butanediamine-N,N')platinum (CI-973), and analogs thereof, 9- aminocamptothecin, 10,11-methylenedioxycamptothecin, karenitecin, 9-nitrocamptothecin, 6-[[2-(dimethylamino)ethyl]amino]-3-hydroxy-7H-indeno [2,1-c] quinolin-7-one dihydrochloride (TAS 103) L-phenylalanine mustard, ifosphamidemefosphamide, trophosphamide carmustine, epothilones A-E, tomudex, 6-mercaptopurine, 6-thioguanine, karenitecin, acyclovir, valacyclovir, ganciclovir, amantadine, rimantadine, lamivudine, zidovudine, bevacizumab, trastuzumab, rituximab, 20-epi-1α, 25dihydroxyvitamin D3, 4-ipomeanol, 5-ethynyluracil, 9-dihydrotaxol, abiraterone, acivicin, aclarubicin, acodazole hydrochloride, acronine, acylfiilvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisazuidinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caraceraide, carbetimer, carboplatin, carboxamide-amino-triazole, carboxyamidotriazole, methylglyoxal maleimide carmustine, cartilage derived inhibitor, carubicin hydrochloride, carzelesin, casein kinase inhibitors, castanospermnine, cecropin B, cedefingol, cetrorelix, chlorambucil, chlorins, chloroquinoxaline sulfonamide, cicaprost, cirolemycin, cisplatin, cisporphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflornithine, eflornithine hydrochloride, elemene, elsarnitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, flurocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide, lobaplatin, lombricine, lometrexol, lometrexol sodium, lomustine, lonidamine, losoxantrone, losoxantrone hydrochloride, lovastatin, loxoribine, lurtotecan, lutetium texaphyrin lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazorurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinarnide, RNAi, rogletimide, rohitukine, romurtide, roquinimex, rubiginone B1, ruboxyl, safingol, safingol hydrochloride, saintopin, sarcnu, sarcophytol A, sargramostim, SDI1 mimetics, semustine, senescence derived inhibitor 1, sense oligonucleotides, signal transduction inhibitors, signal transduction modulators, simtrazene, single chain antigen binding protein, sizofiran, sobuzoxane, sodium borocaptatc, sodium phenylacetate, solverol, somatomedin binding protein, sonermin, sparfosafe sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride, siRNA or any combinations thereof.

18. The method of claim 1, wherein said at least one targeting agent is selected from antibodies, prostate specific membrane antigen (PSMA) ligands and polypeptides that bind to epidermal growth factor receptor (EGFR), somatostatin receptor (SSTR), insulin-like growth factor receptor, folic acid-receptor, HER2 receptor, interleukin-13receptor, gastrin-releasing peptide receptor, CD30, vasoactive intestinal peptide receptor, gastrin receptor, prostate-specific membrane antigen, and/or the estrogen receptor.

19. The method of claim 1, wherein said method is performed in an aqueous medium.

20. The method of claim 1, wherein said method is performed in an organic solvent.

* * * * *

UNITED STATES PATENT AND TRADEMARK OFFICE
CERTIFICATE OF CORRECTION

PATENT NO. : 8,734,846 B2
APPLICATION NO. : 13/667299
DATED : May 27, 2014
INVENTOR(S) : Mir M. Ali et al.

Page 1 of 4

It is certified that error appears in the above-identified patent and that said Letters Patent is hereby corrected as shown below:

In the Specification

Column 5,
Line 15, "Allyl carbamate (Alloc-NR2)" should read --Allyl carbamate (Alloc-NR$_2$)--.

Column 10,
Lines 19-20, "Poly(ester)-block-poly(etheylene glycol)" should read
--Poly(ester)-block-poly(ethylene glycol)--.

Column 11,
Lines 21-22, "involving and azido" should read --involving an azido--.

Columns 13-14, Scheme 5,
Line 10, "reductive animation" should read --reductive amination--.

Column 20,
Lines 36-39,

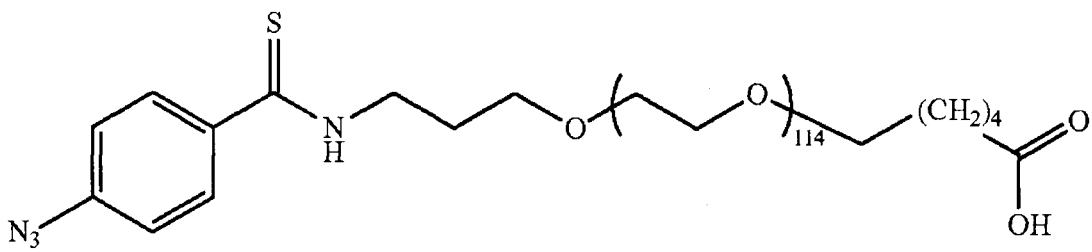

N$_3$-PEG-CO$_2$H

"                                                                                          "

should read

Signed and Sealed this
Tenth Day of February, 2015

Michelle K. Lee
*Deputy Director of the United States Patent and Trademark Office*

CERTIFICATE OF CORRECTION (continued)
U.S. Pat. No. 8,734,846 B2

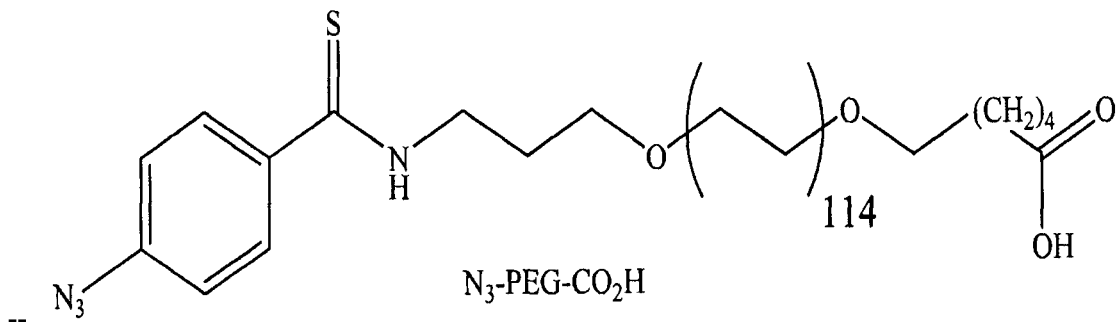

N₃-PEG-CO₂H

Column 22,
Lines 21-22, "the use long" should read --the use of long--.

Column 26,
Line 58, "agents)," should read --agents,--.

Column 27,
Lines 29-30, "methylene-10-deazaminopterin" should read
--methylene-10-deazaaminopterin--.
Line 50, "anti-dorsalizding" should read --anti-dorsalizing--.

Column 28,
Line 1, "malemide," should read --maleimide,--.

Column 31,
Line 44, "can designed" should read --can be designed--.
Line 55, "transferring," should read --transferrin,--.
Line 56, "transferring receptor," should read --transferrin receptor,--.

Column 33,
Line 65,

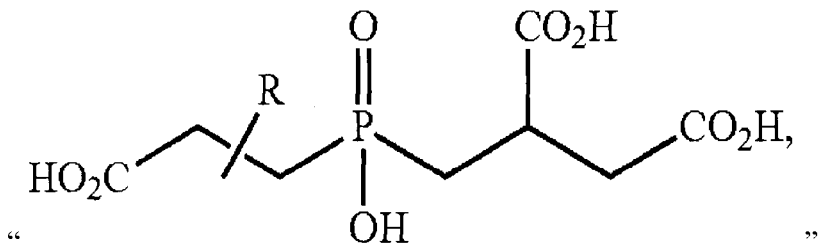

"                                                                        "

should read

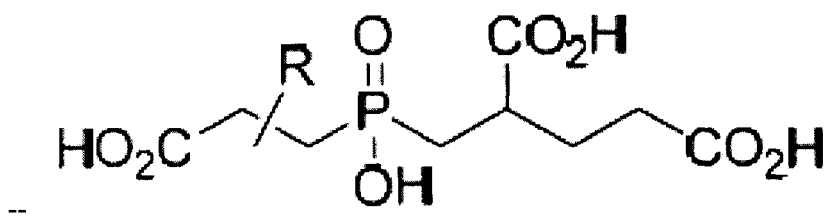

--                                                                        --.

Column 34,
Line 5,
"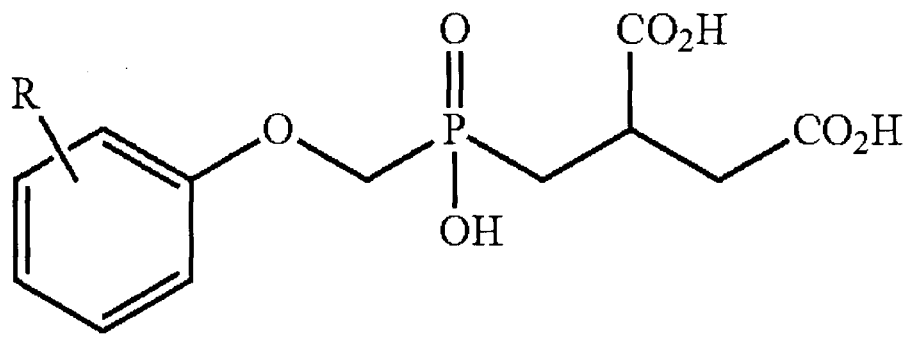"
should read
--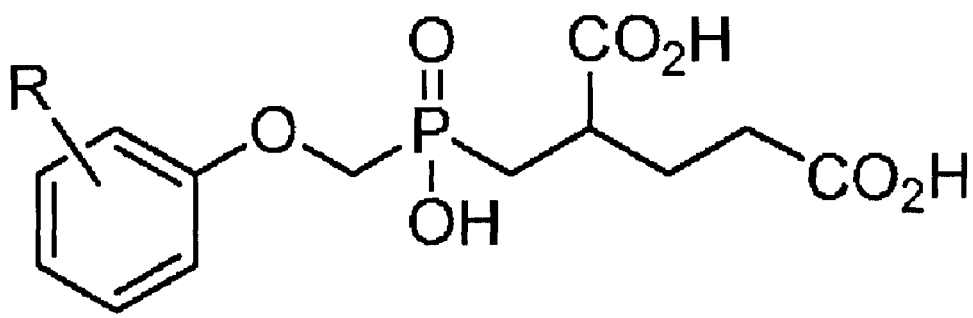--.
Column 34,
Line 10,
"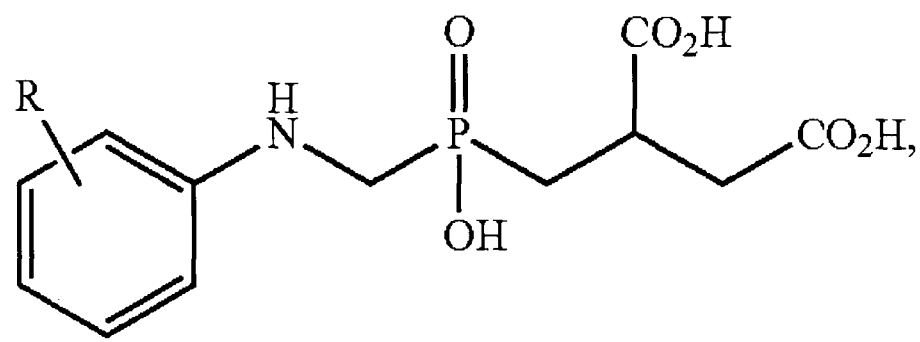"
should read
--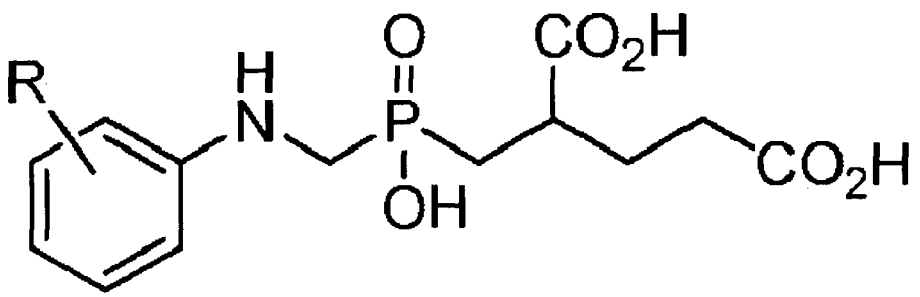--.

CERTIFICATE OF CORRECTION (continued)
U.S. Pat. No. 8,734,846 B2

<u>Column 38,</u>
Line 51, "methylene-10-deazaminopterin" should read
--methylene-10-deazaaminopterin--.

<u>Column 43,</u>
Lines 25-26, "Functionalization with of PEG with" should read
--Functionalization of PEG with--.

<u>Column 45,</u>
Lines 4-5, "washing were" should read --washing was--.
Line 22, "Functionalization with of PEG with" should read
--Functionalization of PEG with--.